(12) United States Patent
Weng et al.

US011919937B2

(10) Patent No.: US 11,919,937 B2
(45) Date of Patent: Mar. 5, 2024

(54) T CELL RECEPTORS FOR IMMUNOTHERAPY

(71) Applicant: Board of Regents, The University of Texas System, Austin, TX (US)

(72) Inventors: Jinsheng Weng, Houston, TX (US); Kelsey Moriarty, Houston, TX (US); Sattva S. Neelapu, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 787 days.

(21) Appl. No.: 16/961,088

(22) PCT Filed: Jan. 9, 2019

(86) PCT No.: PCT/US2019/012880
§ 371 (c)(1),
(2) Date: Jul. 9, 2020

(87) PCT Pub. No.: WO2019/139972
PCT Pub. Date: Jul. 18, 2019

(65) Prior Publication Data
US 2021/0130431 A1      May 6, 2021

Related U.S. Application Data

(60) Provisional application No. 62/615,342, filed on Jan. 9, 2018.

(51) Int. Cl.
| | | |
|---|---|---|
| *C07K 14/725* | (2006.01) | |
| *A61K 35/17* | (2015.01) | |
| *A61K 47/64* | (2017.01) | |
| *A61P 35/00* | (2006.01) | |
| *A61K 38/00* | (2006.01) | |

(52) U.S. Cl.
CPC .......... *C07K 14/7051* (2013.01); *A61K 35/17* (2013.01); *A61K 47/6425* (2017.08); *A61P 35/00* (2018.01); *A61K 38/00* (2013.01)

(58) Field of Classification Search
None
See application file for complete search history.

(56) References Cited

U.S. PATENT DOCUMENTS

| | | |
|---|---|---|
| 5,985,598 A | 11/1999 | Russo et al. |
| 6,410,319 B1 | 6/2002 | Raubitschek et al. |
| 6,451,995 B1 | 9/2002 | Cheung et al. |
| 7,070,995 B2 | 7/2006 | Jensen |
| 7,175,995 B1 | 2/2007 | Russo et al. |
| 7,265,209 B2 | 9/2007 | Jensen |
| 7,354,762 B2 | 4/2008 | Jensen |
| 7,446,179 B2 | 11/2008 | Jensen et al. |
| 7,446,190 B2 | 11/2008 | Sadelain et al. |
| 7,446,191 B2 | 11/2008 | Jensen |
| 7,749,715 B2 | 7/2010 | Russo et al. |
| 7,910,109 B2 | 3/2011 | Carroll et al. |
| 8,324,353 B2 | 12/2012 | Jensen |
| 8,339,645 B2 | 12/2012 | Nakawaki |
| 8,398,282 B2 | 3/2013 | Kuhlman et al. |
| 8,479,118 B2 | 7/2013 | Lyndersay et al. |
| 9,290,541 B2 | 3/2016 | Neelapu et al. |
| 2002/0131960 A1 | 9/2002 | Sadelain et al. |
| 2009/0004142 A1 | 1/2009 | Leturcq et al. |
| 2009/0017000 A1 | 1/2009 | Cai et al. |
| 2013/0149337 A1 | 6/2013 | Cooper et al. |
| 2013/0287748 A1 | 10/2013 | June et al. |
| 2014/0315735 A1 | 10/2014 | Sugiyama |
| 2014/0348902 A1* | 11/2014 | Neelapu ............ A61K 39/0011 435/375 |
| 2015/0010631 A1 | 1/2015 | Getts |
| 2015/0337369 A1 | 11/2015 | Davis et al. |

FOREIGN PATENT DOCUMENTS

| | | |
|---|---|---|
| EP | 2537416 | 12/2012 |
| WO | WO 1996/013514 | 5/1996 |
| WO | WO 2000/014257 | 3/2000 |
| WO | WO 2000/032769 | 6/2000 |
| WO | WO 2000/055169 | 9/2000 |
| WO | WO 2007/103009 | 9/2007 |
| WO | WO 2012/129514 | 9/2012 |
| WO | WO 2013/071154 | 5/2013 |
| WO | WO 2013/075105 | 5/2013 |
| WO | WO 2013/123061 | 8/2013 |
| WO | WO 2013/126726 | 8/2013 |
| WO | WO 2013/166321 | 11/2013 |
| WO | WO 2014/031687 | 2/2014 |
| WO | WO 2014/055668 | 4/2014 |
| WO | WO 2016/070119 | 5/2016 |
| WO | WO 2017/216324 | 12/2017 |

OTHER PUBLICATIONS

Amini et al., Anat Cell Biol. Mar. 2014;47(1):1-11 (Year: 2014).*
"TCL1A overexpression linked to poor outcome in DLCL patients", *Cancer Vaccine Week*, Mar. 21, 2005.
Aggarwal et al., "TCL1A expression delineates biological and clinical variability in B-cell lymphoma", Modern Pathology, 22:206-215, 2009.
Bendandi et al., "Complete molecular remissions induced by patient-specific vaccination plus granulocyte-monocyte colony-stimulating factor against lymphoma", Nat. Med., 5:1171-1177, 1999.
Bertinetti et al., "Phase I trial of a novel intradermal idiotype vaccine in patients with advanced B-cell lymphoma: specific immune responses despite profound immunosuppression", Cancer Res., 66:4496-4502, 2006.
Bichi et al., "Human chronic lymphocytic leukemia modeled in mouse by targeted TCL1 expression," *Proceedings of the National Academy of Sciences of the United States of America*; 99(10):6955-6960, 2002.

(Continued)

*Primary Examiner* — Daniel C Gamett
(74) *Attorney, Agent, or Firm* — Parker Highlander PLLC

(57) ABSTRACT

Provided are T cell receptors (TCR) and TCR variable regions that can selectively bind the T-cell leukemia/lymphoma 1 (TCL1) oncoprotein. The TCR may be utilized in various therapies, such as autologous TCL1-TCR adoptive T cell therapy, to treat a cancer, such as a B-cell malignancy or a solid tumor expressing TCL1. Methods for expanding a population of T cells that target TCL1 are also provided.

19 Claims, 30 Drawing Sheets

Specification includes a Sequence Listing.

(56) References Cited

OTHER PUBLICATIONS

Bijker et al., "CD8+ CTL priming by exact peptide epitopes in incomplete Freund's adjuvant induces a vanishing CTL response, whereas long peptides induce sustained CTL reactivity", J. Immunol., 179:5033-5040, 2007.
Blanchard and Shastri, "Coping with loss of perfection in the MHC class I peptide repertoire", Curr. Opin. Immunol., 20:82-88, 2008.
Brand et al., "Prospect for Anti-HER2 receptor therapy in breast cancer," *Anticancer Research*, 26:463-470, 2006.
Burrows et al., "Have we cut ourselves too short in mapping CTL epitopes?", Trends Immunol., 27:11-16, 2006.
Cameron et al., "Identification of a Titin-Derived HLA-A1-Presented Peptide as a Cross-Reactive Target for Engineered MAGE A3-Directed T Cells," *Science Translational Medicine*; 5(197):197ra103, 2013.
Celluzzi et al., "Peptide-pulsed dendritic cells induce antigen-specific CTL-mediated protective tumor immunity", J. Exp. Med., 183: 283-287, 1996.
Chao, "Treatment challenges in the management of relapsed or refractory non-Hodgkin's lymphoma—novel and emerging therapies," *Cancer Management and Research*; 5:251-69, 2013.
Cheson and Leonard, "Monoclonal antibody therapy for B-cell non-Hodgkin's lymphoma", N. Eng. J. Med., 359:613-626, 2008.
Cohen et al., "Enhanced Antitumor Activity of T Cells Engineered to Express T-Cell Receptors with a Second Disulfide Bond," *Cancer research*; 67(8):3898-903, 2007.
Coiffier et al., "CHOP chemotherapy plus rituximab compared with CHOP alone in elderly patients with diffuse large-B-cell lymphoma", N. Eng. J. Med., 346:235-242, 2002.
Collins et al., "Three-dimensional structure of a peptide extending from one end of a class I MHC binding site", Nature, 371:626-629, 1994.
Davila et al., "CD19 CAR-targeted T cells induce long-term remission and B Cell Aplasia in an immunocompetent mouse model of B cell acute lymphoblastic leukemia," *PLoS ONE*, 8(4): e61338, 2013.
Di Nicola et al., "Vaccination with autologous tumor-loaded dendritic cells induces clinical and immunologic responses in indolent B-cell lymphoma patients with relapsed and measurable disease: a pilot study", Blood, 113:18-27, 2009.
Dudley et al., "Generation of tumor-infiltrating lymphocyte cultures for use in adoptive transfer therapy for melanoma patients", J. Immunol., 26(4):332-342, 2003.
Engelhard, "Structure of peptides associated with MHC class I molecules," *Current Opinion in Immunology*, 6:13-23, 1994.
Fedorov et al., "PD-1- and CTLA-4-based inhibitory chimeric antigen receptors (iCARs) divert off-target immunotherapy responses," *Sci. Transl. Medicine*, 5(215):215ra172, 2013.
Freshney et al., "Culture of Animal Cells, A Manual of Basic Technique," Alan R. Liss, Inc., New York, p. 4, 1983.
Gritti et al., "Transgenic mice for MTCP1 develop T-cell prolymphocytic leukemia", Blood, 92:368-373, 1998.
Guo et al., "Different length peptides bind to HLA-Aw68 similarly at their ends but bulge out in the middle", Nature, 360:364-366, 1992.
Gura, "Systems for identifying new drugs are often faulty," *Science*, 278:1041-1042, 1997.
Hawkins et al., "Development of adoptive cell therapy for cancer: a clinical perspective", Hum. Gene Ther., 21(6):665-72, 2010.
Herling et al., "High TCL1 expression and intact T-cell receptor signaling define a hyperproliferative subset of T-cell prolymphocytic leukemia", Blood, 111(1): 328-337, 2007.
Herling et al., "High TCL1 levels are a marker of B-cell receptor pathway responsiveness and adverse outcome in chronic lymphocytic leukemia", Blood, 114:4675-4686, 2009.
Herling et al., "TCL1 in B-cell tumors retains its normal b-cell pattern of regulation and is a marker of differentiation stage", Am. J. Surg. Pathol., 31:1123-1129, 2007.

Hida et al., "A simple culture protocol to detect peptide-specific cytotoxic T lymphocyte precursors in the circulation", Cancer Immunol. Immunotherapy, 51:219-228, 2002.
Holler et al., "TCRs with high affinity for foreign pMHC show self-reactivity," *Nature immunology*, 4(1):55-62, 2003.
Houot and Levy, "Vaccines for lymphomas: idiotype vaccines and beyond", Blood Rev., 23:137-142, 2009.
Hoyer et al., "Dysregulated TCL1 promotes multiple classes of mature B cell lymphoma", Proc. Natl. Acad. Sci. USA, 99:14392-14397, 2002.
Inogès et al., "Clinical benefit associated with idiotypic vaccination in patients with follicular lymphoma", J. Natl. Cancer Inst., 98:1292-1301, 2006.
Irvine et al., "Direct observation of ligand recognition by T cells", Nature, 419:845-849, 2002.
Jain, "Barriers to drug delivery in solid tumors," *Sci Am.*, 271(1):58-65, 1994.
Johnson et al., "Gene therapy with human and mouse T-cell receptors mediates cancer regression and targets normal tissues expressing cognate antigen," *Blood*; 114(3):535-46. 2009.
Kang et al., "Inhibition of self-binding antibodies (autobodies) by a VH-derived peptide", Science, 240:1034-1036, 1988.
Kochenderfer et al., "Chemotherapy-refractory diffuse large B-cell lymphoma and indolent B-cell malignancies can be effectively treated with autologous T cells expressing an anti-CD19 chimeric antigen receptor," *J Clin Oncol*; 33(6):540-9, 2015.
Kunert et al., "TCR-engineered T cells meet new challenges to treat solid tumors: choice of antigen, T cell fitness and sensitization of tumor milieu," *Frontiers in Immunology*; 4:363, 2013.
Kwak et al., "Induction of immune responses in patients with B-cell lymphoma against the surface-immunoglobulin idiotype expressed by their tumors", N. Eng. J. Med., 327:1209-1215, 1992.
Laine et al., "The protooncogene TCL1 is an Akt kinase coactivator", Molec. Cell, 6:395-407, 2000.
Lee et al., "A novel strategy for rapid and efficient isolation of human tumor-specific CD4(+) and CD8(+) T-cell clones", J. Immunol. Methods, 331:13-26, 2008.
Linette et al., "Cardiovascular toxicity and titin cross-reactivity of affinity-enhanced T cells in myeloma and melanoma," *Blood*; 122(6):863-871, 2013.
Locke et al., "Phase 1 Results of ZUMA-1: A Multicenter Study of KTE-C19 Anti-CD19 CAR T Cell Therapy in Refractory Aggressive Lymphoma," *Mol Ther.*; 25(1):285-295, 2017.
Malyguine et al., "A modified human ELISPOT assay to detect specific responses to primary tumor cell targets", J. Transl. Med., 2(1):9, 2004.
Marcus et al., "CVP chemotherapy plus rituximab compared with CVP as first-line treatment for advanced follicular lymphoma", Blood, 105:1417-1423, 2005.
Maus et al., "Ex vivo expansion of polyclonal and antigen-specific cytotoxic T lymphocytes by artificial APCs expressing ligands for the T-cell receptor, CD28 and 4-1BB", Nat. Biotech., 20:143-148, 2002.
McLaughlin et al., "Rituximab chimeric anti-CD20 monoclonal antibody therapy for relapsed indolent lymphoma: half of patients respond to a four-dose treatment program", J. Clin. Oncol., 16:2825-2833, 1998.
Melief and van der Burg, "Immunotherapy of established (pre)malignant disease by synthetic long peptide vaccines", *Nat. Rev. Cancer*, 8:351-360, 2008.
Morgan R et al., "Cancer regression and neurological toxicity following anti-MAGE-A3 TCR gene therapy," *Journal of immunotherapy*, 36(2):133-151. 2013.
Narducci et al., "Regulation of TCL1 expression in b- and t-cell lymphomas and reactive lymphoid tissues", *Cancer Research*, 60:2095-2100, 2000.
Narducci et al., "TCL1 is overexpressed in patients affected by adult T-cell leukemias", Cancer Res., 57:5452-5456, 1997.
Narducci et al., "TCL1 participates in early embryonic development and is overexpressed in human seminomas", Proc. Natl. Acad. Sci. USA, 99:11712-11717, 2002.
Narducci et al., "The murine Tcl1 oncogene: embryonic and lymphoid cell expression", Oncogene, 15:919-926, 1997a.

(56) References Cited

OTHER PUBLICATIONS

Navarrete et al., "Upfront immunization with autologous recombinant idiotype Fab fragment without prior cytoreduction in indolent B-cell lymphoma", *Blood*, 117:1483-1491, 2011.
Neelapu and Kwak, "Vaccine therapy for b-cell lymphomas: next-generation strategies", *Hematology*, pp. 243-249, 2007.
Neelapu et al., "Axicabtagene ciloleucel CAR T-cell therapy in refractory large B-cell lymphoma," *N Engl J Med.*, Dec. 28, 2017;377(26): 2531-2544.
Neelapu et al., "Vaccine-induced tumor-specific immunity despite severe B-cell depletion in mantle cell lymphoma", *Nat. Med.*, 11:986-991, 2005.
Nestle et al., "Vaccination of melanoma patients with peptide- or tumor lysate-pulsed dendritic cells", *Nat. Med.*, 4:328, 1998.
Park and Neelapu, "Developing idiotype vaccines for lymphoma: from preclinical studies to phase III clinical trials", *Br. J. Haemat.*, 142:179-191, 2008.
PCT International Preliminary Report on Patentability issued in International Application No. PCT/US2012/065866, dated May 30, 2014.
PCT International Preliminary Report on Patentability issued in International Application No. PCT/US2019/012880, dated Jul. 23, 2020.
PCT International Search Report and Written Opinion issued in International Application No. PCT/US2012/065866, dated Mar. 13, 2013.
PCT International Search Report and Written Opinion issued in International Application No. PCT/US2019/012880, dated May 13, 2019.
Pekarsky et al., "Tcl1 functions as a transcriptional regulator and is directly involved in the pathogenesis of CLL", *Proc. Natl. Acad. Sci. USA*, 105:19643-19648, 2008.
Porter et al., "Chimeric antigen receptor-modified T cells in chronic lymphoid leukemia," *The New England journal of medicine*; 365(8):725-733, 2011.
Quintarelli et al., "High-avidity cytotoxic T lymphocytes specific for a new PRAME-derived peptide can target leukemic and leukemic-precursor cells", *Blood*, 117:3353-3362, 2011.
Rammensee et al., "MHC ligands and peptide motifs: first listing," *Immunogenetics*, 41:178-228, 1995.
Ramuz et al., "Identification of TCL1A as an immunohistochemical marker of adverse outcome in diffuse large B-cell lymphomas", *Int. J Oncol.*, 26:151-157, 2005.
Ribas et al., "Determinant spreading and tumor responses after peptide-based cancer immunotherapy", *Trends Immunol.*, 24:58-61, 2003.
Riddell et al., "The use of anti-CD3 and anti-CD28 monoclonal antibodies to clone and expand human antigen-specific T cells", *J. Immunol.*, 128(2):189-201, 1990.
Sadelain et al., "The basic principles of chimeric antigen receptor design," *Cancer Discov.*, 3(4):388-398, 2013.
Said et al., "TCL1 oncogene expression in B cell subsets from lymphoid hyperplasia and distinct classes of B cell lymphoma", *Lab. Invest.* 81:555-564, 2001.
Samino et al., "A long N-terminal-extended nested set of abundant and antigenic major histocompatibility complex class I natural ligands from HIV envelope protein", *J. Biol. Chem.*, 281:6358-6365, 2006.
Schuster et al., "Sustained Remissions Following Chimeric Antigen Receptor Modified T Cells Directed Against CD19 (CTL019) in Patients with Relapsed or Refractory CD19+ Lymphomas," *Blood*; 126(23):183, 2015.
Schuster et al., "Vaccination with patient-specific tumor-derived antigen in first remission improves disease-free survival in follicular lymphoma", *J. Clin. Oncol.*, 29(20):2787-94, 2011.
Shastri et al., "Presentation of endogenous peptide/MHC class I complexes is profoundly influenced by specific C-terminal flanking residues," *J. Immunol.*, 155:4339-4346, 1995.
Skull and Kemp, "Treatment of hypogammaglobulinaemia with intravenous immunoglobulin, 1973-93", *Arch. Dis. Child.*, 74:527-530, 1996.
Sotillo et al., "Convergence of Acquired Mutations and Alternative Splicing of CD19 Enables Resistance to CART-19 Immunotherapy," *Cancer Discov*; 5(12):1282-1295, 2015.
Stone et al., "TCR affinity for p/MHC formed by tumor antigens that are self-proteins: impact on efficacy and toxicity," *Curr Opin Immunol.*; 33:16-22, 2015.
Strome et al., "A mechanistic perspective of monoclonal antibodies in cancer therapy beyond target-related effects," *The Oncologist*, 12:1084-1095, 2007.
Stryhn et al., "Longer peptide can be accommodated in the MHC class I binding site by a protrusion mechanism", *Eur. J. Immunol.*, 30:3089-3099, 2000.
Teitell, "The TCL1 family of oncoproteins: co-activators of transformation", *Nat. Rev. Cancer*, 5:640-648, 2005.
Timmerman et al., "Idiotype-pulsed dendritic cell vaccination for B-cell lymphoma: clinical and immune responses in 35 patients", *Blood*, 99:1517-1526, 2002.
Topp et al., "Phase II trial of the anti-CD19 bispecific T cell-engager blinatumomab shows hematologic and molecular remissions in patients with relapsed or refractory B-precursor acute lymphoblastic leukemia," *J Clin Oncol.*; 32(36):4134-40, 2014.
Turtle et al., "CD19 CAR-T cells are highly effective in ibrutinib-refractory chronic lymphocytic leukemia," *Blood*; 128(22):56, 2016.
Turtle et al., "Engineered T cells for anti-cancer therapy," *Curr. Opin. Immunol.*, 24(5):633-639, 2012.
Turtle et al., "Immunotherapy of non-Hodgkin's lymphoma with a defined ratio of CD8+ and CD4+ CD19-specific chimeric antigen receptor-modified T cells," *Science translational medicine*; 8(355):355ra116, 2016.
van Loenen et al., "Optimization of the HA-1-specific T-cell receptor for gene therapy of hematologic malignancies," *Haematologica*; 96(3):477-481, 2011.
Virgilio et al., "Deregulated expression of TCL1 causes T cell leukemia in mice", *Proc. Natl. Acad. Sci. USA*, 95:3885-3889, 1998.
Weng et al., "Targeting B-cell malignancies through human B-cell receptor specific CD4+ T cells," *Oncoimmunology*; 5(11):e1232220, 2016.
Weng et al., "TCL1: a shared tumor-associated antigen for immunotherapy against B-cell lymphomas", *Blood*, 120(8): 1613-1623, 2012.
Wu et al., "Adoptive T-cell Therapy Using Autologous Tumor-infiltrating Lymphocytes for Metastatic Melanoma: Current Status and Future Outlook," *Cancer J.*, 18(2):160-175, 2012.
Young and Inaba, "Dendritic cells as adjuvants for class I major histocompatibility complex-restricted antitumor immunity", *J. Exp. Med.*, 183(1):7-11, 1996.
Zhong et al., "T-cell receptor affinity and avidity defines antitumor response and autoimmunity in T-cell immunotherapy," *Proc Natl Acad Sci U S A*. 2013;110(17):6973-8.
Zwaveling et al., "Established human papillomavirus type 16-expressing tumors are effectively eradicated following vaccination with long peptides", *J Immunol.*, 169:350-358, 2002.

\* cited by examiner

| TCL1-T clone | TCRα | | | TCRβ | | | |
|---|---|---|---|---|---|---|---|
| | Vα | Jα | Cα | Vβ | Jβ | D | Cβ |
| TC1 | TRAV1-1*02 | TRAJ28*01 | Cα1 | TRBV5-5*01 | TRBJ2-7*01 | TRBD2*01 | Cβ2 |

| TCL1 10mer | TCL1 70-70 peptides sequnces | SEQ ID NO |
|---|---|---|
| A1 | ALLPIMWQLY | 9 |
| A2 | SALPIMWQLY | 10 |
| A3 | SLAPIMWQLY | 11 |
| A4 | SLLAIMWQLY | 12 |
| A5 | SLLPAMWQLY | 13 |
| A6 | SLLPIAWQLY | 14 |
| A7 | SLLPIMAQLY | 15 |
| A8 | SLLPIMWALY | 16 |
| A9 | SLLPIMWQAY | 17 |
| A10 | SLLPIMWQLA | 18 |
| G1 | GLLPIMWQLY | 19 |
| G2 | SGLPIMWQLY | 20 |
| G3 | SLGPIMWQLY | 21 |
| G4 | SLLGIMWQLY | 22 |
| G5 | SLLPGMWQLY | 23 |
| G6 | SLLPIGWQLY | 24 |
| G7 | SLLPIMGQLY | 25 |
| G8 | SLLPIMWGLY | 26 |
| G9 | SLLPIMWQGY | 27 |
| G10 | SLLPIMWQLG | 28 |
| 10mer | SLLPIMWQLY | 29 |
| T2 | | |

FIG. 8A

TCL1-TCR alpha DNA sequence

ATGTGGGGCGCCTTCCTGCTGTACGTGTCCATGAAGATGGGAGGAACCGCAGGACAGTCTCTGGAGCAGCCAAGC
GAGGTGACAGCAGTGGAGGGAGCAATCGTGCAGATCAACTGCACCTACCAGACAAGCGGCTTTTACGGCCTGTCC
TGGTATCAGCAGCACGACGGAGGAGCACCCACCTTCCTGAGCTATAATGGCCTGGATGGCCTGGAGGAGACAGGC
CGGTTCAGCTCCTTTCTGTCTAGAAGCGACTCCTACGGCTATCTGCTGCTGCAGGAGCTGCAGATGAAGGATTCT
GCCAGCTACTTTTGTCTGCTGGGAAGCGGAGCAGGATCCTATCAGCTGACCTTCGGCAAGGGCACAAAGCTGTCC
GTGATCCCTAACATCCAGAACCCCGACCCTGCCGTGTACCAGCTGCGGGACAGCAAGAGCAGCGACAAGAGCGTG
TG
CCTGTTCACCGACTTCGACAGCCAGACCAACGTGTCCCAGAGCAAGGACAGCGACGTGTA
CATCACCGATAAGTGCGTGCTGGACATGCGGAGCATGGACTTCAAGAGCAACAGCGCCGT
GGCCTGGTCCAACAAGAGCGACTTCGCCTGCGCCAACGCCTTCAACAACAGCATCATCCC
CGAGGACACATTCTTCCCAAGCCCCGAGAGCAGCTGCGACGTGAAACTGGTGGAAAAGAG
CTTCGAGACAGACACCAACCTGAACTTCCAGAACCTGAGCGTGATCGGCTTCCGGATCCT
GCTGCTGAAGGTGGCCGGCTTCAACCTGCTGATGACCCTGCGGCTGTGGTCCAGCTGA

TCL1-TCR beta DNA sequence

ATGGGACCAGGCCTGCTGTGCTGGGTGCTGCTGTGCCTGCTGGGAGCAGGACCTGTGGATGCCGGCGTGACCCAG
AGCCCAACACACCTGATCAAGACCAGGGGACAGCACGTGACACTGAGGTGCTCCCCAATCTCTGGCCACAAGTCC
GTGTCTTGGTACCAGCAGGTGCTGGGACAGGGACCACAGTTCATCTTTCAGTACTATGAGAAGGAGGAGCGGGGC
AGAGGCAACTTCCCCGACAGGTTTTCCGCCCGCCAGTTTCCTAATTACTCTAGCGAGCTGAACGTGAATGCCCTG
CTGCTGGGCGACAGCGCCCTGTATCTGTGCGCCTCCTCTTTTACCGATGGCGGCACATACGAGCAGTATTTCGGC
CCTGGCACCAGGCTGACCGTGACAGAGGACCTGAAGAACGTGTTCCCCCCTGAGGTGGCCGTGTTTGAGCCTTCC
GAGGCCGAGATC
TCTCACACCCAGAAGGCCACCCTGGTGTGCCTGGCAACCGGCTTCTACCCAGATCACGTGGAGCTGTCTTGGTGG
GTGAACGGCAAGGAGGTGCACAGCGGCGTGTGCACAGACCCACAGCCCCTGAAGGAGCAGCCCGCCCTGAATGAT
TCCCGGTACTGTCTGAGCTCCAGGCTGCGCGTGTCTGCCACCTTTTGGCAGAACCCTCGGAATACTTCAGATGC
CAGGTGCAGTTTTATGGCCTGTCCGAGAACGATGAGTGGACCCAGGACAGGGCAAAGCCAGTGACACAGATCGTG
TCTGCCGAGGCATGGGAAGAGCAGACTGTGGCTTCACCAGCGAGTCCTATCAGCAGGGCGTGCTGAGCGCCACC
ATCCTGTACGAGATCCTGCTGGGCAAGGCCACACTGTATGCCGTGCTGGTGTCTGCCCTGGTGCTGATGGCCATG
GTGAAGAGGAAGGATAGCCGCGGCTGA

FIG. 11

TCL1-TCR alpha protein sequence

<u>MWGAFLLYVSMKMGGTAGQSLEQPSEVTAVEGAIVQIN</u>
<u>CTYQTSGFYGLSWYQQHDGGAPTFLSYNGLDGLEETGR</u>
<u>FSSFLSRSDSYGYLLLQELQMKDSASYFCLLGSGAGSY</u>
<u>QLTFGKGTKLSVIPN</u>IQNPDPAVYQLRDSKSSDKSVCL
FTDFDSQTNVSQSKDSDVYITDKCVLDMRSMDFKSNSA
VAWSNKSDFACANAFNNSIIPEDTFFPSPESSCDVKLV
EKSFETDTNLNFQNLSVIGFRILLLKVAGFNLLMTRL
WSS

TCL1-TCR beta protein sequence

<u>MGPGLLCWVLLCLLGAGPVDAGVTQSPTHLIKTRGQHV</u>
<u>TLRCSPISGHKSVSWYQQVLGQGPQFIFQYYEKEERGR</u>
<u>GNFPDRFSARQFPNYSSELNVALLLGDSALYLCASSF</u>
<u>TDGGTYEQYFGPGTRLTVTE</u>DLKNVFPPEVAVFEPSEA
EISHTQKATLVCLATGFYPDHVELSWWVNGKEVHSGVC
TDPQPLKEQPALNDSRYCLSSRLRVSATFWQNPRNHFR
CQVQFYGLSENDEWTQDRAKPVTQIVSAEAWGRADCGF
TSESYQQGVLSATILYEILLGKATLYAVLVSALV
LMAMVKRKDSRG

<u>Underlined:</u> Highly variable region sequence of TCL1-TCR alpha and beta chain

FIG. 12

TCL1-TCR alpha DNA sequence

ATGTGGGGCGCCTTCCTGCTGTACGTGTCCATGAAGATGGGAGGAACCGCAGGACAGTCTCTGGAGCAGCCAAGC
GAGGTGACAGCAGTGGAGGGAGCAATCGTGCAGATCAACTGCACCTACCAG<u>ACAAGCGGCTTTTACGGC</u>CTGTCC
TGGTATCAGCAGCACGACGGAGGAGCACCCACCTTCCTGAGCTAT<u>AATGGCCTGGATGGCCTG</u>GAGGAGACAGGC
CGGTTCAGCTCCTTTCTGTCTAGAAGCGACTCCTACGGCTATCTGCTGCTGCAGGAGCTGCAGATGAAGGATTCT
GCCAGCTACTTTTGT<u>CTGCTGGGAAGCGGAGCAGGATCCTATCAGCTGACC</u>TTCGGCAAGGGCACAAAGCTGTCC
GTGATCCCTAACATCCAGAACCCCGACCCTGCCGTGTACCAGCTGCGGGACAGCAAGAGCAGCGACAAGAGCGTG
TG
CCTGTTCACCGACTTCGACAGCCAGACCAACGTGTCCCAGAGCAAGGACAGCGACGTGTA
CATCACCGATAAGTGCGTGCTGGACATGCGGAGCATGGACTTCAAGAGCAACAGCGCCGT
GGCCTGGTCCAACAAGAGCGACTTCGCCTGCGCCAACGCCTTCAACAACAGCATCATCCC
CGAGGACACATTCTTCCCAAGCCCCGAGAGCAGCTGCGACGTGAAACTGGTGGAAAAGAG
CTTCGAGACAGACACCAACCTGAACTTCCAGAACCTGAGCGTGATCGGCTTCCGGATCCT
GCTGCTGAAGGTGGCCGGCTTCAACCTGCTGATGACCCTGCGGCTGTGGTCCAGCTGA     (SEQ ID NO:7)

TCL1-TCR beta DNA sequence

ATGGGACCAGGCCTGCTGTGCTGGGTGCTGCTGTGCCTGCTGGGAGCAGGACCTGTGGATGCCGGCGTGACCCAG
AGCCCAACACACCTGATCAAGACCAGGGGACAGCACGTGACACTGAGGTGCTCCCCAATC<u>TCTGGCCACAAGTCC</u>
GTGTCTTGGTACCAGCAGGTGCTGGGACAGGGACCACAGTTCATCTTTCAG<u>TACTATGAAGGAGGAGC</u>GGGGC
AGAGGCAACTTCCCCGACAGGTTTTCCGCCCGCCAGTTTCCTAATTACTCTAGCGAGCTGAACGTGAATGCCCTG
CTGCTGGGCGACAGCGCCCTGTATCTGTGC<u>GCCTCCTCTTTTACCGATGGCGGCACATACGAGCAGTAT</u>TTCGGC
CCTGGCACCAGGCTGACCGTGACAGAGGACCTGAAGAACGTGTTCCCCCCTGAGGTGGCCGTGTTTGAGCCTTCC
GAGGCCGAGATC
TCTCACACCCAGAAGGCCACCCTGGTGTGCCTGGCAACCGGCTTCTACCCAGATCACGTGGAGCTGTCTTGGTGG
GTGAACGGCAAGGAGGTGCACAGCGGCGTGTGCACAGACCCACAGCCCCTGAAGGAGCAGCCCGCCCTGAATGAT
TCCCGGTACTGTCTGAGCTCCAGGCTGCGCGTGTCTGCCACCTTTTGGCAGAACCCTCGGAATCACTTCAGATGC
CAGGTGCAGTTTTATGGCCTGTCCGAGAACGATGAGTGGACCCAGGACAGGGCAAAGCCAGTGACACAGATCGTG
TCTGCCGAGGCATGGGGAAGAGCAGACTGTGGCTTCACCAGCGAGTCCTATCAGCAGGGCGTGCTGAGCGCCACC
ATCCTGTACGAGATCCTGCTGGGCAAGGCCACACTGTATGCCGTGCTGGTGTCTGCCCTGGTGCTGATGGCCATG
GTGAAGAGGAAGGATAGCCGCGGCTGA     (SEQ ID NO:8)

<u>Underlined:</u> CDR1, CDR2, CDR3 sequence of TCL1-TCR alpha and beta sequence

FIG. 13

TCL1-TCR alpha protein sequence

M W G A F L L Y V S M K M G G T A G Q S L E Q P S E V T A V E G A I V Q I N
C T Y Q <u>T S G F Y G</u> L S W Y Q Q H D G G A P T F L S Y <u>N G L D G L</u> E E T G R
F S S F L S R S D S Y G Y L L L Q E L Q M K D S A S Y F C <u>L L G S G A G S Y</u>
<u>Q L T</u> F G K G T K L S V I P N I Q N P D P A V Y Q L R D S K S S D K S V C L
F T D F D S Q T N V S Q S K D S D V Y I T D K C V L D M R S M D F K S N S A
V A W S N K S D F A C A N A F N N S I I P E D T F F P S P E S S C D V K L V
E K S F E T D T N L N F Q N L S V I G F R I L L L K V A G F N L L M T L R L
W S S (SEQ ID NO:3)

TCL1-TCR beta protein sequence

M G P G L L C W V L L C L L G A G P V D A G V T Q S P T H L I K T R G Q H V
T L R C S P I <u>S G H K S</u> V S W Y Q Q V L G Q G P Q F I F Q <u>Y Y E K E E</u> R G R
G N F P D R F S A R Q F P N Y S S E L N V A L L L G D S A L Y L C <u>A S S F</u>
<u>T D G G T Y E Q Y</u> F G P G T R L T V T E D L K N V F P P E V A V F E P S E A
E I S H T Q K A T L V C L A T G F Y P D H V E L S W W V N G K E V H S G V C
T D P Q P L K E Q P A L N D S R Y C L S S R L R V S A T F W Q N P R N H F R
C Q V Q F Y G L S E N D E W T Q D R A K P V T Q I V S A E A W G R A D C G F
T S E S Y Q Q G V L S A T I L Y E I L L G K A T L Y A V L V S A L V
L M A M V K R K D S R G (SEQ ID NO:4)

<u>Underlined:</u> CDR1, CDR2, CDR3 sequence of TCL1-TCR alpha and beta sequence

FIG. 13 – cont'd

SEQUENCE LISTING

```
<160> NUMBER OF SEQ ID NOS: 59

<210> SEQ ID NO 1
<211> LENGTH: 129
<212> TYPE: PRT
<213> ORGANISM: Artificial sequence
<220> FEATURE:
<223> OTHER INFORMATION: Synthetic peptide

<400> SEQUENCE: 1

Met Trp Gly Ala Phe Leu Leu Tyr Val Ser Met Lys Met Gly Gly Thr
1               5                   10                  15

Ala Gly Gln Ser Leu Glu Gln Pro Ser Glu Val Thr Ala Val Glu Gly
            20                  25                  30

Ala Ile Val Gln Ile Asn Cys Thr Tyr Gln Thr Ser Gly Phe Tyr Gly
        35                  40                  45

Leu Ser Trp Tyr Gln Gln His Asp Gly Gly Ala Pro Thr Phe Leu Ser
    50                  55                  60

Tyr Asn Gly Leu Asp Gly Leu Glu Glu Thr Gly Arg Phe Ser Ser Phe
65                  70                  75                  80

Leu Ser Arg Ser Asp Ser Tyr Gly Tyr Leu Leu Leu Gln Glu Leu Gln
                85                  90                  95

Met Lys Asp Ser Ala Ser Tyr Phe Cys Leu Leu Gly Ser Gly Ala Gly
            100                 105                 110

Ser Tyr Gln Leu Thr Phe Gly Lys Gly Thr Lys Leu Ser Val Ile Pro
        115                 120                 125

Asn

<210> SEQ ID NO 2
<211> LENGTH: 134
<212> TYPE: PRT
<213> ORGANISM: Artificial sequence
<220> FEATURE:
<223> OTHER INFORMATION: Synthetic peptide

<400> SEQUENCE: 2

Met Gly Pro Gly Leu Leu Cys Trp Val Leu Leu Cys Leu Leu Gly Ala
1               5                   10                  15

Gly Pro Val Asp Ala Gly Val Thr Gln Ser Pro Thr His Leu Ile Lys
            20                  25                  30

Thr Arg Gly Gln His Val Thr Leu Arg Cys Ser Pro Ile Ser Gly His
        35                  40                  45

Lys Ser Val Ser Trp Tyr Gln Gln Val Leu Gly Gln Gly Pro Gln Phe
    50                  55                  60

Ile Phe Gln Tyr Tyr Glu Lys Glu Glu Arg Gly Arg Gly Asn Phe Pro
65                  70                  75                  80

Asp Arg Phe Ser Ala Arg Gln Phe Pro Asn Tyr Ser Ser Glu Leu Asn
                85                  90                  95
```

```
Val Asn Ala Leu Leu Leu Gly Asp Ser Ala Leu Tyr Leu Cys Ala Ser
            100                 105                 110

Ser Phe Thr Asp Gly Gly Thr Tyr Glu Gln Tyr Phe Gly Pro Gly Thr
        115                 120                 125

Arg Leu Thr Val Thr Glu
    130
```

<210> SEQ ID NO 3
<211> LENGTH: 269
<212> TYPE: PRT
<213> ORGANISM: Artificial sequence
<220> FEATURE:
<223> OTHER INFORMATION: Synthetic peptide

<400> SEQUENCE: 3

```
Met Trp Gly Ala Phe Leu Leu Tyr Val Ser Met Lys Met Gly Gly Thr
1               5                   10                  15

Ala Gly Gln Ser Leu Glu Gln Pro Ser Glu Val Thr Ala Val Glu Gly
            20                  25                  30

Ala Ile Val Gln Ile Asn Cys Thr Tyr Gln Thr Ser Gly Phe Tyr Gly
        35                  40                  45

Leu Ser Trp Tyr Gln Gln His Asp Gly Gly Ala Pro Thr Phe Leu Ser
    50                  55                  60

Tyr Asn Gly Leu Asp Gly Leu Glu Glu Thr Gly Arg Phe Ser Ser Phe
65                  70                  75                  80

Leu Ser Arg Ser Asp Ser Tyr Gly Tyr Leu Leu Leu Gln Glu Leu Gln
                85                  90                  95

Met Lys Asp Ser Ala Ser Tyr Phe Cys Leu Leu Gly Ser Gly Ala Gly
            100                 105                 110

Ser Tyr Gln Leu Thr Phe Gly Lys Gly Thr Lys Leu Ser Val Ile Pro
        115                 120                 125

Asn Ile Gln Asn Pro Asp Pro Ala Val Tyr Gln Leu Arg Asp Ser Lys
    130                 135                 140

Ser Ser Asp Lys Ser Val Cys Leu Phe Thr Asp Phe Asp Ser Gln Thr
145                 150                 155                 160

Asn Val Ser Gln Ser Lys Asp Ser Asp Val Tyr Ile Thr Asp Lys Cys
                165                 170                 175

Val Leu Asp Met Arg Ser Met Asp Phe Lys Ser Asn Ser Ala Val Ala
            180                 185                 190

Trp Ser Asn Lys Ser Asp Phe Ala Cys Ala Asn Ala Phe Asn Asn Ser
        195                 200                 205

Ile Ile Pro Glu Asp Thr Phe Phe Pro Ser Pro Glu Ser Ser Cys Asp
    210                 215                 220

Val Lys Leu Val Glu Lys Ser Phe Glu Thr Asp Thr Asn Leu Asn Phe
225                 230                 235                 240

Gln Asn Leu Ser Val Ile Gly Phe Arg Ile Leu Leu Leu Lys Val Ala
                245                 250                 255

Gly Phe Asn Leu Leu Met Thr Leu Arg Leu Trp Ser Ser
            260                 265
```

<210> SEQ ID NO 4
<211> LENGTH: 312
<212> TYPE: PRT
<213> ORGANISM: Artificial sequence
<220> FEATURE:
<223> OTHER INFORMATION: Synthetic peptide

<400> SEQUENCE: 4

Met Gly Pro Gly Leu Leu Cys Trp Val Leu Leu Cys Leu Leu Gly Ala
1               5                   10                  15

Gly Pro Val Asp Ala Gly Val Thr Gln Ser Pro Thr His Leu Ile Lys
            20                  25                  30

Thr Arg Gly Gln His Val Thr Leu Arg Cys Ser Pro Ile Ser Gly His
        35                  40                  45

Lys Ser Val Ser Trp Tyr Gln Gln Val Leu Gly Gln Gly Pro Gln Phe
    50                  55                  60

Ile Phe Gln Tyr Tyr Glu Lys Glu Arg Gly Arg Gly Asn Phe Pro
65                  70                  75                  80

Asp Arg Phe Ser Ala Arg Gln Phe Pro Asn Tyr Ser Glu Leu Asn
                85                  90                  95

Val Asn Ala Leu Leu Leu Gly Asp Ser Ala Leu Tyr Leu Cys Ala Ser
            100                 105                 110

Ser Phe Thr Asp Gly Gly Thr Tyr Glu Gln Tyr Phe Gly Pro Gly Thr
        115                 120                 125

Arg Leu Thr Val Thr Glu Asp Leu Lys Asn Val Phe Pro Pro Glu Val
        130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Cys Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Ser Arg Gly
305                 310

<210> SEQ ID NO 5
<211> LENGTH: 387
<212> TYPE: DNA
<213> ORGANISM: Artificial sequence
<220> FEATURE:
<223> OTHER INFORMATION: Synthetic oligonucleotide

<400> SEQUENCE: 5
atgtggggcg ccttcctgct gtacgtgtcc atgaagatgg gaggaaccgc aggacagtct      60
ctggagcagc caagcgaggt gacagcagtg gagggagcaa tcgtgcagat caactgcacc     120
taccagacaa gcggctttta cggcctgtcc tggtatcagc agcacgacgg aggagcaccc     180
accttcctga gctataatgg cctggatggc ctggaggaga caggccggtt cagctccttt     240

```
ctgtctagaa gcgactccta cggctatctg ctgctgcagg agctgcagat gaaggattct    300
gccagctact tttgtctgct gggaagcgga gcaggatcct atcagctgac cttcggcaag    360
ggcacaaagc tgtccgtgat ccctaac                                        387
```

<210> SEQ ID NO 6
<211> LENGTH: 400
<212> TYPE: DNA
<213> ORGANISM: Artificial sequence
<220> FEATURE:
<223> OTHER INFORMATION: Synthetic oligonucleotide

<400> SEQUENCE: 6

```
atgggaccag gcctgctgtg ctgggtgctg ctgtgcctgc tgggagcagg acctgtggat    60
gccggcgtga cccagagccc aacacacctg atcaagacca gggacagca cgtgacactg     120 aggtgctccc caatctctgg ccacaagtcc gtgtcttggt accagcaggt gctgggacag    180
ggaccacagt tcatctttca gtactatgag aaggaggagc ggggcagagg caacttcccc    240
gacaggtttt ccgcccgcca gtttcctaat tactctagcg agctgaacgt gaatgccctg    300
ctgctgggcg acagcgccct gtatctgtgc gcctcctctt ttaccgatgg cggcacatac    360
gagcagtatt tcggccctgg caccaggctg accgtgacag                          400
```

<210> SEQ ID NO 7
<211> LENGTH: 810
<212> TYPE: DNA
<213> ORGANISM: Artificial sequence
<220> FEATURE:
<223> OTHER INFORMATION: Synthetic oligonucleotide

<400> SEQUENCE: 7

```
atgtggggcg ccttcctgct gtacgtgtcc atgaagatgg gaggaaccgc aggacagtct    60
ctggagcagc caagcgaggt gacagcagtg gagggagcaa tcgtgcagat caactgcacc    120
taccagacaa gcggcttttta cggcctgtcc tggtatcagc agcacgacgg aggagcaccc    180
accttcctga gctataatgg cctggatggc ctggaggaga caggccggtt cagctccttt    240
ctgtctagaa gcgactccta cggctatctg ctgctgcagg agctgcagat gaaggattct    300
gccagctact tttgtctgct gggaagcgga gcaggatcct atcagctgac cttcggcaag    360
ggcacaaagc tgtccgtgat ccctaacatc agaaccccg accctgccgt gtaccagctg    420
cgggacagca agagcagcga caagagcgtg tgcctgttca ccgacttcga cagccagacc    480
aacgtgtccc cagagcaagga cagcgacgtg tacatcaccg ataagtgcgt gctggacatg    540
cggagcatgg acttcaagag caacagcgcc gtggcctggt ccaacaagag cgacttcgcc    600
tgcgccaacg ccttcaacaa cagcatcatc cccgaggaca cattcttccc aagccccgag    660
agcagctgcg acgtgaaact ggtggaaaag agcttcgaga cagacaccaa cctgaacttc    720
cagaacctga gcgtgatcgg cttccggatc ctgctgctga aggtggccgg cttcaacctg    780
ctgatgaccc tgcggctgtg gtccagctga                                     810
```

<210> SEQ ID NO 8
<211> LENGTH: 939
<212> TYPE: DNA
<213> ORGANISM: Artificial sequence
<220> FEATURE:
<223> OTHER INFORMATION: Synthetic oligonucleotide

<400> SEQUENCE: 8

-continued

| | | |
|---|---|---|
| atgggaccag gcctgctgtg ctgggtgctg ctgtgcctgc tgggagcagg acctgtggat | 60 |
| gccggcgtga cccagagccc aacacacctg atcaagacca ggggacagca cgtgacactg | 120 |
| aggtgctccc caatctctgg ccacaagtcc gtgtcttggt accagcaggt gctgggacag | 180 |
| ggaccacagt tcatctttca gtactatgag aaggaggagc ggggcagagg caacttcccc | 240 |
| gacaggtttt ccgcccgcca gtttcctaat tactctagcg agctgaacgt gaatgccctg | 300 |
| ctgctgggcg acagcgccct gtatctgtgc gcctcctctt ttaccgatgg cggcacatac | 360 |
| gagcagtatt tcggccctgg caccaggctg accgtgacag aggacctgaa gaacgtgttc | 420 |
| ccccctgagg tggccgtgtt tgagccttcc gaggccgaga tctctcacac ccagaaggcc | 480 |
| accctggtgt gcctggcaac cggcttctac ccagatcacg tggagctgtc ttggtgggtg | 540 |
| aacggcaagg aggtgcacag cggcgtgtgc acagacccac agcccctgaa ggagcagccc | 600 |
| gccctgaatg attcccggta ctgtctgagc tccaggctgc gcgtgtctgc caccttttgg | 660 |
| cagaaccctc ggaatcactt cagatgccag gtgcagtttt atggcctgtc cgagaacgat | 720 |
| gagtggaccc aggacagggc aaagccagtg acacagatcg tgtctgccga ggcatgggga | 780 |
| agagcagact gtggcttcac cagcgagtcc tatcagcagg gcgtgctgag cgccaccatc | 840 |
| ctgtacgaga tcctgctggg caaggccaca ctgtatgccg tgctggtgtc tgccctggtg | 900 |
| ctgatggcca tggtgaagag gaaggatagc cgcggctga | 939 |

<210> SEQ ID NO 9
<211> LENGTH: 10
<212> TYPE: PRT
<213> ORGANISM: Artificial sequence
<220> FEATURE:
<223> OTHER INFORMATION: Synthetic peptide

<400> SEQUENCE: 9

Ala Leu Leu Pro Ile Met Trp Gln Leu Tyr
1               5                   10

<210> SEQ ID NO 10
<211> LENGTH: 10
<212> TYPE: PRT
<213> ORGANISM: Artificial sequence
<220> FEATURE:
<223> OTHER INFORMATION: Synthetic peptide

<400> SEQUENCE: 10

Ser Ala Leu Pro Ile Met Trp Gln Leu Tyr
1               5                   10

<210> SEQ ID NO 11
<211> LENGTH: 10
<212> TYPE: PRT
<213> ORGANISM: Artificial sequence
<220> FEATURE:
<223> OTHER INFORMATION: Synthetic peptide

<400> SEQUENCE: 11

Ser Leu Ala Pro Ile Met Trp Gln Leu Tyr
1               5                   10

<210> SEQ ID NO 12
<211> LENGTH: 10
<212> TYPE: PRT
<213> ORGANISM: Artificial sequence
<220> FEATURE:
<223> OTHER INFORMATION: Synthetic peptide

```
<400> SEQUENCE: 12

Ser Leu Leu Ala Ile Met Trp Gln Leu Tyr
1               5                   10

<210> SEQ ID NO 13
<211> LENGTH: 10
<212> TYPE: PRT
<213> ORGANISM: Artificial sequence
<220> FEATURE:
<223> OTHER INFORMATION: Synthetic peptide

<400> SEQUENCE: 13

Ser Leu Leu Pro Ala Met Trp Gln Leu Tyr
1               5                   10

<210> SEQ ID NO 14
<211> LENGTH: 10
<212> TYPE: PRT
<213> ORGANISM: Artificial sequence
<220> FEATURE:
<223> OTHER INFORMATION: Synthetic peptide

<400> SEQUENCE: 14

Ser Leu Leu Pro Ile Ala Trp Gln Leu Tyr
1               5                   10

<210> SEQ ID NO 15
<211> LENGTH: 10
<212> TYPE: PRT
<213> ORGANISM: Artificial sequence
<220> FEATURE:
<223> OTHER INFORMATION: Synthetic peptide

<400> SEQUENCE: 15

Ser Leu Leu Pro Ile Met Ala Gln Leu Tyr
1               5                   10

<210> SEQ ID NO 16
<211> LENGTH: 10
<212> TYPE: PRT
<213> ORGANISM: Artificial sequence
<220> FEATURE:
<223> OTHER INFORMATION: Synthetic peptide

<400> SEQUENCE: 16

Ser Leu Leu Pro Ile Met Trp Ala Leu Tyr
1               5                   10

<210> SEQ ID NO 17
<211> LENGTH: 10
<212> TYPE: PRT
<213> ORGANISM: Artificial sequence
<220> FEATURE:
<223> OTHER INFORMATION: Synthetic peptide

<400> SEQUENCE: 17

Ser Leu Leu Pro Ile Met Trp Gln Ala Tyr
1               5                   10

<210> SEQ ID NO 18
<211> LENGTH: 10
<212> TYPE: PRT
<213> ORGANISM: Artificial sequence
<220> FEATURE:
<223> OTHER INFORMATION: Synthetic peptide

<400> SEQUENCE: 18
```

Ser Leu Leu Pro Ile Met Trp Gln Leu Ala
1               5                   10

<210> SEQ ID NO 19
<211> LENGTH: 10
<212> TYPE: PRT
<213> ORGANISM: Artificial sequence
<220> FEATURE:
<223> OTHER INFORMATION: Synthetic peptide

<400> SEQUENCE: 19

Gly Leu Leu Pro Ile Met Trp Gln Leu Tyr
1               5                   10

<210> SEQ ID NO 20
<211> LENGTH: 10
<212> TYPE: PRT
<213> ORGANISM: Artificial sequence
<220> FEATURE:
<223> OTHER INFORMATION: Synthetic peptide

<400> SEQUENCE: 20

Ser Gly Leu Pro Ile Met Trp Gln Leu Tyr
1               5                   10

<210> SEQ ID NO 21
<211> LENGTH: 10
<212> TYPE: PRT
<213> ORGANISM: Artificial sequence
<220> FEATURE:
<223> OTHER INFORMATION: Synthetic peptide

<400> SEQUENCE: 21

Ser Leu Gly Pro Ile Met Trp Gln Leu Tyr
1               5                   10

<210> SEQ ID NO 22
<211> LENGTH: 10
<212> TYPE: PRT
<213> ORGANISM: Artificial sequence
<220> FEATURE:
<223> OTHER INFORMATION: Synthetic peptide

<400> SEQUENCE: 22

Ser Leu Leu Gly Ile Met Trp Gln Leu Tyr
1               5                   10

<210> SEQ ID NO 23
<211> LENGTH: 10
<212> TYPE: PRT
<213> ORGANISM: Artificial sequence
<220> FEATURE:
<223> OTHER INFORMATION: Synthetic peptide

<400> SEQUENCE: 23

Ser Leu Leu Pro Gly Met Trp Gln Leu Tyr
1               5                   10

<210> SEQ ID NO 24
<211> LENGTH: 10
<212> TYPE: PRT
<213> ORGANISM: Artificial sequence
<220> FEATURE:
<223> OTHER INFORMATION: Synthetic peptide

<400> SEQUENCE: 24

Ser Leu Leu Pro Ile Gly Trp Gln Leu Tyr
1               5                   10

<210> SEQ ID NO 25
<211> LENGTH: 10
<212> TYPE: PRT
<213> ORGANISM: Artificial sequence
<220> FEATURE:
<223> OTHER INFORMATION: Synthetic peptide

<400> SEQUENCE: 25

Ser Leu Leu Pro Ile Met Gly Gln Leu Tyr
1               5                   10

<210> SEQ ID NO 26
<211> LENGTH: 10
<212> TYPE: PRT
<213> ORGANISM: Artificial sequence
<220> FEATURE:
<223> OTHER INFORMATION: Synthetic peptide

<400> SEQUENCE: 26

Ser Leu Leu Pro Ile Met Trp Gly Leu Tyr
1               5                   10

<210> SEQ ID NO 27
<211> LENGTH: 10
<212> TYPE: PRT
<213> ORGANISM: Artificial sequence
<220> FEATURE:
<223> OTHER INFORMATION: Synthetic peptide

<400> SEQUENCE: 27

Ser Leu Leu Pro Ile Met Trp Gln Gly Tyr
1               5                   10

<210> SEQ ID NO 28
<211> LENGTH: 10
<212> TYPE: PRT
<213> ORGANISM: Artificial sequence
<220> FEATURE:
<223> OTHER INFORMATION: Synthetic peptide

<400> SEQUENCE: 28

Ser Leu Leu Pro Ile Met Trp Gln Leu Gly
1               5                   10

<210> SEQ ID NO 29
<211> LENGTH: 10
<212> TYPE: PRT
<213> ORGANISM: Artificial sequence
<220> FEATURE:
<223> OTHER INFORMATION: Synthetic peptide

<400> SEQUENCE: 29

Ser Leu Leu Pro Ile Met Trp Gln Leu Tyr
1               5                   10

<210> SEQ ID NO 30
<211> LENGTH: 4
<212> TYPE: PRT
<213> ORGANISM: Artificial sequence
<220> FEATURE:
<223> OTHER INFORMATION: Synthetic peptide

<400> SEQUENCE: 30

Arg Ala Lys Arg

```
<210> SEQ ID NO 31
<211> LENGTH: 18
<212> TYPE: PRT
<213> ORGANISM: Artificial sequence
<220> FEATURE:
<223> OTHER INFORMATION: Synthetic peptide

<400> SEQUENCE: 31

Ala Thr Asn Phe Ser Leu Leu Lys Gln Ala Gly Asp Val Glu Glu Asn
1               5                   10                  15

Pro Gly

<210> SEQ ID NO 32
<211> LENGTH: 4
<212> TYPE: PRT
<213> ORGANISM: Artificial sequence
<220> FEATURE:
<223> OTHER INFORMATION: Synthetic peptide

<400> SEQUENCE: 32

Ser Gly Ser Gly
1

<210> SEQ ID NO 33
<211> LENGTH: 8
<212> TYPE: PRT
<213> ORGANISM: Artificial sequence
<220> FEATURE:
<223> OTHER INFORMATION: Synthetic peptide

<400> SEQUENCE: 33

Leu Leu Pro Ile Met Trp Gln Leu
1               5

<210> SEQ ID NO 34
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 34
gagagcaagt acggccctcc ctgcccccct tgccct                          36

<210> SEQ ID NO 35
<211> LENGTH: 60
<212> TYPE: DNA
<213> ORGANISM: Artificial sequence
<220> FEATURE:
<223> OTHER INFORMATION: Synthetic oligonucleotide

<400> SEQUENCE: 35
agccaggaag agatgaccaa gaaccaggtg tccctgacct gcctcgtgaa gggcttctac    60

<210> SEQ ID NO 36
<211> LENGTH: 141
<212> TYPE: DNA
<213> ORGANISM: Artificial sequence
<220> FEATURE:
<223> OTHER INFORMATION: Synthetic oligonucleotide

<400> SEQUENCE: 36
aagcctacca caacccctgc cccagacct cctacacccg ccccctacaat tgccagccag    60
```

```
cctctgtctc tgaggcccga ggcttgtaga cctgctgctg gcggagccgt gcacaccaga    120
ggactggatt tcgcctgcga c                                              141

<210> SEQ ID NO 37
<211> LENGTH: 696
<212> TYPE: DNA
<213> ORGANISM: Artificial sequence
<220> FEATURE:
<223> OTHER INFORMATION: Synthetic oligonucleotide

<400> SEQUENCE: 37
agcgagagca agtacggccc tccctgcccc ccttgccctg ccccgagtt cctgggcgga     60 cccagcgtgt tcctgttccc ccccaagccc aaggacaccc tgatgatcag ccggaccccc   120
gaggtgacct gtgtggtggt ggacgtgtcc caggaggacc ccgaggtcca gttcaactgg   180
tacgtggacg gcgtggaggt gcacaacgcc aagaccaagc ccgggagga gcagttcaat   240 agcacctacc gggtggtgtc cgtgctgacc gtgctgcacc aggactggct gaacggcaag   300
gaatacaagt gtaaggtgtc caacaagggc ctgcccagca gcatcgagaa aaccatcagc   360
aaggccaagg gccagcctcg ggagcccag gtgtacaccc tgcccctag ccaagaggag   420 atgaccaaga atcaggtgtc cctgacctgc ctggtgaagg gcttctaccc cagcgacatc   480
gccgtggagt gggagagcaa cggccagccc gagaacaact acaagaccac ccccctgtg   540 ctggacagcg acggcagctt cttcctgtac agcaggctga ccgtggacaa gagccggtgg   600
caggagggca acgtctttag ctgctccgtg atgcacgagg ccctgcacaa ccactacacc   660
cagaagagcc tgtccctgag cctgggcaag atgttc                              696

<210> SEQ ID NO 38
<211> LENGTH: 58
<212> TYPE: DNA
<213> ORGANISM: Artificial sequence
<220> FEATURE:
<223> OTHER INFORMATION: Synthetic oligonucleotide

<400> SEQUENCE: 38
agccaggaag agatgaccaa gaaccaggtg tccctgacct gcctcgtgaa gggcttct      58

<210> SEQ ID NO 39
<211> LENGTH: 696
<212> TYPE: DNA
<213> ORGANISM: Artificial sequence
<220> FEATURE:
<223> OTHER INFORMATION: Synthetic oligonucleotide

<400> SEQUENCE: 39
agcgagagca agtacggccc tccctgcccc ccttgccctg ccccgagtt cctgggcgga     60 cccagcgtgt tcctgttccc ccccaagccc aaggacaccc tgatgatcag ccggaccccc   120
gaggtgacct gtgtggtggt ggacgtgtcc caggaggacc ccgaggtcca gttcaactgg   180
tacgtggacg gcgtggaggt gcacaacgcc aagaccaagc ccgggagga gcagttccag   240 agcacctacc gggtggtgtc cgtgctgacc gtgctgcacc aggactggct gaacggcaag   300
gaatacaagt gtaaggtgtc caacaagggc ctgcccagca gcatcgagaa aaccatcagc   360
aaggccaagg gccagcctcg ggagcccag gtgtacaccc tgcccctag ccaagaggag   420 atgaccaaga atcaggtgtc cctgacctgc ctggtgaagg gcttctaccc cagcgacatc   480
gccgtggagt gggagagcaa cggccagccc gagaacaact acaagaccac ccccctgtg   540 ctggacagcg acggcagctt cttcctgtac agcaggctga ccgtggacaa gagccggtgg   600
```

```
caggagggca acgtctttag ctgctccgtg atgcacgagg ccctgcacaa ccactacacc      660
cagaagagcc tgtccctgag cctgggcaag atgttc                               696

<210> SEQ ID NO 40
<211> LENGTH: 696
<212> TYPE: DNA
<213> ORGANISM: Artificial sequence
<220> FEATURE:
<223> OTHER INFORMATION: Synthetic oligonucleotide

<400> SEQUENCE: 40
agcgagagca agtacggccc tccctgcccc ccttgccctg ccccgagtt cgaaggcgga       60 cccagcgtgt tcctgttccc ccccaagccc aaggacaccc tgatgatcag ccggaccccc     120
gaggtgacct gtgtggtggt ggacgtgtcc caggaggacc ccgaggtcca gttcaactgg     180
tacgtggacg gcgtggaggt gcacaacgcc aagaccaagc cccgggagga gcagttccag     240
agcacctacc gggtggtgtc cgtgctgacc gtgctgcacc aggactggct gaacggcaag     300
gaatacaagt gtaaggtgtc caacaagggc ctgcccagca gcatcgagaa aaccatcagc     360
aaggccaagg gccagcctcg ggagccccag gtgtacaccc tgcccccctag ccaagaggag    420 atgaccaaga atcaggtgtc cctgacctgc ctggtgaagg gcttctaccc cagcgacatc    480
gccgtggagt gggagagcaa cggccagccc gagaacaact acaagaccac cccccctgtg    540
ctggacagcg acggcagctt cttcctgtac agcaggctga ccgtggacaa gagccggtgg    600
caggagggca acgtctttag ctgctccgtg atgcacgagg ccctgcacaa ccactacacc    660
cagaagagcc tgtccctgag cctgggcaag atgttc                              696

<210> SEQ ID NO 41
<211> LENGTH: 711
<212> TYPE: DNA
<213> ORGANISM: Artificial sequence
<220> FEATURE:
<223> OTHER INFORMATION: Synthetic oligonucleotide

<400> SEQUENCE: 41
atggtgtcca agggcgagga actgatcaaa gaaaacatgc acatgaagct gtacatggaa      60
ggcaccgtga caaccacca cttcaagtgc accagcgagg gagagggcaa gccctacgag     120
ggcacccaga ccatgcggat caaggtggtc gagggcggac tctgcccctt cgccttcgac     180
atcctggcca caagcttcat gtacggcagc aagaccttca tcaaccacac ccagggcatc     240 cccgattttct tcaagcagag cttccccgag ggcttcacct gggagagagt gaccacctac     300
gaggacggcg gcgtgctgac cgccacccag gacaccagcc tgcaggacgg ctgcctgatc     360
tacaacgtga agatccgggg cgtgaacttc cccagcaacg gccccgtgat gcagaagaaa     420
accctgggct gggaggccag caccgagatg ctgtaccctg ccgatggcgg cctggaaggc     480
agagccgaca tggccctgaa actggtcggc ggagggcacc tgatctgcaa cctgaaaacc     540
acctacagaa gcaagaagcc cgccaagaac ctgaagatgc ccggcgtgta ctacgtggac     600
cggcggctgg aaaggatcaa agaggccgac aaagaaacct acgtggagca gcacgaggtg     660
gccgtggccc ggtactgcga cctgcccctcc aagctgggcc acaaactgaa c            711

<210> SEQ ID NO 42
<211> LENGTH: 333
<212> TYPE: DNA
<213> ORGANISM: Artificial sequence
<220> FEATURE:
```

<223> OTHER INFORMATION: Synthetic oligonucleotide

<400> SEQUENCE: 42

| atgatcgaga agtccttcgt gatcaccgac ccccggctgc cgactaccc tatcatcttt | 60 |
| gccagcgacg gcttcctgga actgaccgag tacagccggg aagagatcat gggccggaac | 120 |
| gccagattcc tgcagggccc cgaaaccgat caggccaccg tgcagaagat ccgggacgcc | 180 |
| atcagggacc agcgggaaac cacagtgcag ctgatcaact acaccaagag cggcaagaag | 240 |
| ttctggaacc tgctgcatct gcagcccgtg cgggatagaa agggcggcct gcagtacttc | 300 |
| atcggcgtgc agctcgtggg cagcgaccac gtg | 333 |

<210> SEQ ID NO 43
<211> LENGTH: 675
<212> TYPE: DNA
<213> ORGANISM: Artificial sequence
<220> FEATURE:
<223> OTHER INFORMATION: Synthetic oligonucleotide

<400> SEQUENCE: 43

| atggccagca gcgaggacgt gatcaaagaa ttcatgcggt tcaaagtgcg gatggaaggc | 60 |
| agcgtgaacg gccacgagtt cgagattgag ggcgagggcg aaggcagacc ctacgaggga | 120 |
| acacagaccg ccaagctgaa agtgaccaag ggcggacccc tgcccttcgc ctgggatatc | 180 |
| ctgagccccc agttccagta cggcagcaag gtgtacgtga agcaccccgc cgacatcccc | 240 |
| gactacaaga gctgagcttt ccccgagggc ttcaagtggg agagagtgat gaacttcgag | 300 |
| gacggcggcg tcgtgaccgt gacccaggat agctctctgc aggacggcag cttcatctac | 360 |
| aaagtgaagt ttatcggcgt gaacttcccc agcgacggcc ccgtgatgca gaaaaagacc | 420 |
| atgggctggg aggccagcac cgagagactg taccctagag atggcgtgct gaagggcgag | 480 |
| atccacaagg ccctgaagct gaaggatggc ggccactacc tggtggaatt caagagcatc | 540 |
| tacatggcca agaaacccgt gcagctgccc ggctactact acgtggacag caagctggac | 600 |
| atcaccagcc acaacgagga ctacaccatc gtggaacagt acgagcgggc cgagggccgg | 660 |
| caccatctgt ttctg | 675 |

<210> SEQ ID NO 44
<211> LENGTH: 717
<212> TYPE: DNA
<213> ORGANISM: Artificial sequence
<220> FEATURE:
<223> OTHER INFORMATION: Synthetic oligonucleotide

<400> SEQUENCE: 44

| atggtgtcca agggcgagga actgttcacc ggcgtggtgc ccatcctggt ggaactggat | 60 |
| ggcgacgtga acggccacaa gttcagcgtg tccggcgagg gcgaaggcga cgccacatat | 120 |
| ggcaagctga ccctgaagct gatctgcacc accggcaagc tgcccgtgcc ttggcctacc | 180 |
| ctcgtgacca cactgggcta cggcctgcag tgcttcgcca gataccccga ccatatgaag | 240 |
| cagcacgact tcttcaagag cgccatgccc gagggctacg tgcaggaacg gaccatcttc | 300 |
| tttaaggacg acggcaacta caagaccagg gccgaagtga agttcgaggg cgacaccctc | 360 |
| gtgaaccgga tcgagctgaa gggcatcgac ttcaaagagg acggcaacat cctgggccac | 420 |
| aagctggagt acaactacaa cagccacaac gtgtacatca ccgccgacaa gcagaagaac | 480 |
| ggcatcaagg ccaacttcaa gatccggcac aacatcgagg acggcggcgt gcagctggcc | 540 |
| gatcactacc agcagaacac ccctatcggc gacggccctg tgctgctgcc cgacaatcac | 600 |

-continued

| | | |
|---|---|---|
| tacctgagct accagagcgc cctgagcaag gaccccaacg agaagcggga ccacatggtg | 660 | |
| ctgctggaat tcgtgaccgc cgctggcatc accctgggca tggacgagct gtacaag | 717 | |

<210> SEQ ID NO 45
<211> LENGTH: 717
<212> TYPE: DNA
<213> ORGANISM: Artificial sequence
<220> FEATURE:
<223> OTHER INFORMATION: Synthetic oligonucleotide

<400> SEQUENCE: 45

| | | |
|---|---|---|
| atggtgagca agggcgagga gctgttcacc ggggtggtgc ccatcctggt cgagctggac | 60 | |
| ggcgacgtaa acggccacaa gttcagcgtg tccggcgagg gcgagggcga tgccacctac | 120 | |
| ggcaagctga ccctgaagtt catctgcacc accggcaagc tgcccgtgcc ctggcccacc | 180 | |
| ctcgtgacca ccctgaccta cggcgtgcag tgcttcagcc gctaccccga ccacatgaag | 240 | |
| cagcacgact tcttcaagtc cgccatgccc gaaggctacg tccaggagcg caccatcttc | 300 | |
| ttcaaggacg acggcaacta caagacccgc gccgaggtga agttcgaggg cgacaccctg | 360 | |
| gtgaaccgca tcgagctgaa gggcatcgac ttcaaggagg acggcaacat cctggggcac | 420 | |
| aagctggagt acaactacaa cagccacaac gtctatatca tggccgacaa gcagaagaac | 480 | |
| ggcatcaagg tgaacttcaa gatccgccac aacatcgagg acggcagcgt gcagctcgcc | 540 | |
| gaccactacc agcagaacac ccccatcggc gacggccccg tgctgctgcc cgacaaccac | 600 | |
| tacctgagca cccagtccgc cctgagcaaa gaccccaacg agaagcgcga tcacatggtc | 660 | |
| ctgctggagt tcgtgaccgc cgccgggatc actctcggca tggacgagct gtacaag | 717 | |

<210> SEQ ID NO 46
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 46

| | | |
|---|---|---|
| gccaagggcc agcctcggga gccccaggtg tacaccctgc cccctagcca agaggagatg | 60 | |
| accaagaatc aggtgtccct gacctgcctg gtgaagggct tctacccag cgacatcgcc | 120 | |
| gtggagtggg agagcaacgg ccagcccgag aacaactaca agaccacccc cctgtgctg | 180 | |
| gacagcgacg gcagcttctt cctgtacagc aggctgaccg tggacaagag ccggtggcag | 240 | |
| gagggcaacg tctttagctg ctccgtgatg cacgaggccc tgcacaacca ctacacccag | 300 | |
| aagagcctgt ccctgagcct gggcaagatg ttctacccat cgatgttcc agattacgct | 360 | |
| tac | 363 | |

<210> SEQ ID NO 47
<211> LENGTH: 708
<212> TYPE: DNA
<213> ORGANISM: Artificial sequence
<220> FEATURE:
<223> OTHER INFORMATION: Synthetic oligonucleotide

<400> SEQUENCE: 47

| | | |
|---|---|---|
| atggtgagca agggcgagga gaccacaatg ggcgtaatca agcccgacat gaagatcaag | 60 | |
| ctgaagatgg agggcaacgt gaatggccac gccttcgtga tcgagggcga gggcgagggc | 120 | |
| aagccctacg acggcaccaa caccatcaac ctggaggtga aggagggagc ccccctgccc | 180 | |

```
ttctcctacg acattctgac caccgcgttc gcctacggca acagggcctt caccaagtac      240
cccgacgaca tccccaacta cttcaagcag tccttccccg agggctactc ttgggagcgc      300
accatgacct tcgaggacaa gggcatcgtg aaggtgaagt ccgacatctc catggaggag      360
gactccttca tctacgagat acacctcaag ggcgagaact tccccccca cggccccgtg      420 atgcagaaga agaccaccgg ctgggacgcc tccaccgaga ggatgtacgt gcgcgacggc      480
gtgctgaagg gcgacgtcaa gcacaagctg ctgctggagg cggcggcca ccaccgcgtt      540 gacttcaaga ccatctacag ggccaagaag gcggtgaagc tgcccgacta tcactttgtg      600
gaccaccgca tcgagatcct gaaccacgac aaggactaca acaaggtgac cgtttacgag      660
agcgccgtgg cccgcaactc caccgacggc atggacgagc tgtacaag                  708
```

```
<210> SEQ ID NO 48
<211> LENGTH: 423
<212> TYPE: DNA
<213> ORGANISM: Artificial sequence
<220> FEATURE:
<223> OTHER INFORMATION: Synthetic oligonucleotide

<400> SEQUENCE: 48
aagcctacca caaccctgc ccccagacct cctacacccg ccctacaat tgccagccag        60 cctctgtctc tgaggcccga ggcttgtaga cctgctgctg gcggagccgt gcacaccaga     120
ggactggatt tcgcctgcga caagcctacc acaaccctg ccccagacc tcctacaccc      180 gccctacaa ttgccagcca gcctctgtct ctgaggcccg aggcttgtag acctgctgct     240
ggcggagccg tgcacaccag aggactggat ttcgcctgcg acagcagcgg cggcggcggc     300
agcggcggcg gcggcagcgg cggcggcggc agcgcgcagc tgaaaaaaaa actgcaggcg     360
ctgaaaaaaa aaacgcgcca gctgaaatgg aaactgcagg cgctgaaaaa aaaactggcg     420
cag                                                                  423
```

```
<210> SEQ ID NO 49
<211> LENGTH: 423
<212> TYPE: DNA
<213> ORGANISM: Artificial sequence
<220> FEATURE:
<223> OTHER INFORMATION: Synthetic oligonucleotide

<400> SEQUENCE: 49
aagcctacca caaccctgc ccccagacct cctacacccg ccctacaat tgccagccag        60 cctctgtctc tgaggcccga ggcttgtaga cctgctgctg gcggagccgt gcacaccaga     120
ggactggatt tcgcctgcga caagcctacc acaaccctg ccccagacc tcctacaccc      180 gccctacaa ttgccagcca gcctctgtct ctgaggcccg aggcttgtag acctgctgct     240
ggcggagccg tgcacaccag aggactggat ttcgcctgcg acagcagcgg cggcggcggc     300
agcggcggcg gcggcagcgg cggcggcggc agcgcccagc tggaaaaaga gctgcaggcc     360
ctggaaaaag aaaacgctca gctggaatgg gaactgcagg ctctggaaaa agagctggcc     420
cag                                                                  423
```

```
<210> SEQ ID NO 50
<211> LENGTH: 69
<212> TYPE: DNA
<213> ORGANISM: Artificial sequence
<220> FEATURE:
<223> OTHER INFORMATION: Synthetic oligonucleotide

<400> SEQUENCE: 50
```
tgggtgctgg tcgtggtggg tggcgtgctg gcctgctaca gcctgctggt gacagtggcc    60
ttcatcatc                                                             69

<210> SEQ ID NO 51
<211> LENGTH: 81
<212> TYPE: DNA
<213> ORGANISM: Artificial sequence
<220> FEATURE:
<223> OTHER INFORMATION: Synthetic oligonucleotide

<400> SEQUENCE: 51
attatctcat tcttcctggc cctgacctct accgccctgc tgtttctgct gttctttctg    60
accctgcggt tcagcgtggt g                                               81

<210> SEQ ID NO 52
<211> LENGTH: 84
<212> TYPE: DNA
<213> ORGANISM: Artificial sequence
<220> FEATURE:
<223> OTHER INFORMATION: Synthetic oligonucleotide

<400> SEQUENCE: 52
atctacatct gggcgccctt ggccgggact tgtggggtcc ttctcctgtc actggttatc    60 acccttttact gcaaccacag gaac                                           84

<210> SEQ ID NO 53
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 53
ctctgctacc tgctggatgg aatcctcttc atctatggtg tcattctcac tgccttgttc    60
ctg                                                                   63

<210> SEQ ID NO 54
<211> LENGTH: 6
<212> TYPE: PRT
<213> ORGANISM: Artificial sequence
<220> FEATURE:
<223> OTHER INFORMATION: Synthetic peptide

<400> SEQUENCE: 54

Thr Ser Gly Phe Tyr Gly
1               5

<210> SEQ ID NO 55
<211> LENGTH: 6
<212> TYPE: PRT
<213> ORGANISM: Artificial sequence
<220> FEATURE:
<223> OTHER INFORMATION: Synthetic peptide

<400> SEQUENCE: 55

Asn Gly Leu Asp Gly Leu
1               5

<210> SEQ ID NO 56
<211> LENGTH: 12
<212> TYPE: PRT
<213> ORGANISM: Artificial sequence
<220> FEATURE:

```
<223> OTHER INFORMATION: Synthetic peptide

<400> SEQUENCE: 56

Leu Leu Gly Ser Gly Ala Gly Ser Tyr Gln Leu Thr
1               5                   10

<210> SEQ ID NO 57
<211> LENGTH: 5
<212> TYPE: PRT
<213> ORGANISM: Artificial sequence
<220> FEATURE:
<223> OTHER INFORMATION: Synthetic peptide

<400> SEQUENCE: 57

Ser Gly His Lys Ser
1               5

<210> SEQ ID NO 58
<211> LENGTH: 6
<212> TYPE: PRT
<213> ORGANISM: Artificial sequence
<220> FEATURE:
<223> OTHER INFORMATION: Synthetic peptide

<400> SEQUENCE: 58

Tyr Tyr Glu Lys Glu Glu
1               5

<210> SEQ ID NO 59
<211> LENGTH: 13
<212> TYPE: PRT
<213> ORGANISM: Artificial sequence
<220> FEATURE:
<223> OTHER INFORMATION: Synthetic peptide

<400> SEQUENCE: 59

Ala Ser Ser Phe Thr Asp Gly Gly Thr Tyr Glu Gln Tyr
1               5                   10
```

T CELL RECEPTORS FOR IMMUNOTHERAPY

This application is a national phase application under 35 U.S.C. § 371 of International Application No. PCT/US2019/012880, filed Jan. 9, 2019, which claims the benefit of U.S. Provisional Patent Application No. 62/615,342, filed Jan. 9, 2018, the entirety of each of which is incorporated herein by reference.

BACKGROUND OF THE INVENTION

This application claims the benefit of U.S. Provisional Patent Application No. 62/615,342, filed Jan. 9, 2018, the entirety of which is incorporated herein by reference.

1. Field of the Invention

The present invention relates generally to the field of immunology and medicine. More particularly, it concerns T cell receptors (TCR). In some embodiments the TCR may be used to treat a cancer.

2. Description of Related Art

Although T cell-based therapies have shown significant promise for treating a variety of cancers, relapse after administration of an immunotherapy or chemotherapeutic remains a significant clinical problem. For example, while aggressive B-cell non-Hodgkin lymphomas (NHL) and chronic lymphocytic leukemia (CLL) are often responsive to combinations of chemotherapy and anti-CD20 monoclonal antibodies (Plosker and Figgitt, 2003), relapse remains a serious clinical problem. About two-thirds of patients with aggressive NHL can be cured by chemoimmunotherapy, but a third of patients experience recurrent relapses and eventually die of their disease (Chao M P, 2013). Recent studies with chimeric antigen receptor (CAR)-modified T-cell therapy targeting CD19 demonstrate that CAR T-cell therapy induces high response rates in the majority of patients with refractory B-cell malignancies (Porter et al., 2011; Kochenderfer et al., 2015; Turtle et al., 2016a; Neelapu et al., 2017; Schuster et al., 2015; Turtle et al., 2016b; Locke et al., 2017). A subset of these patients experience long-term remissions suggesting adoptive T-cell therapy could be an effective therapeutic strategy and possibly curative for some of these patients. However, >50% of patients relapse or progress after CD19 CAR T-cell therapy, and a major of cause of failure appears to be due to loss of CD19 expression on the tumor (Sotillo et al., 2015; Topp et al., 2014; Neelapu et al., 2017). Therefore, novel targets for adoptive T-cell therapeutic approaches are needed to further improve clinical outcome in these patients.

TCL1 is an oncoprotein with aberrant expression in >90% of common B-cell malignancies. For example, TCL1 is hyperexpressed in multiple human B-cell lymphomas, including follicular lymphoma, chronic lymphocytic leukemia, mantle cell lymphoma, diffuse large B-cell lymphoma and splenic marginal zone B-cell lymphoma. In addition, it is aberrantly expressed in a variety of solid tumors. In normal tissues, its expression is restricted to normal B cells. Although data suggests that TCL1 may be an important target for these cancers (Weng et al., 2012), specific T-cell receptors (TCR) that selectively bind this target are still needed for use in T-cell immunotherapies.

SUMMARY OF THE INVENTION

In some aspects, the present invention overcomes limitations in the art by providing new T-cell receptors (TCR) that selectively target the T-cell leukemia/lymphoma 1 (TCL1) oncoprotein encoded by the TCL1 gene. In various embodiments, these TCRs that target TCL1 may be included or used in an immunotherapy to treat a cancer such as, e.g., a B-cell malignancy or a solid tumor expressing TCL1. In a preferred embodiment, the TCR has antigenic specificity for a TCL1 peptide comprising, consisting of, or consisting essentially of SLLPIMWQLY (SEQ ID NO:29). As used herein, the phrase "having antigenic specificity" means that the TCR can specifically bind to and immunologically recognize TCL1, such that the binding of the TCR to TCL1 elicits an immune response.

As shown in the below examples, T-cell receptors (TCR) having antigenic specificity for TCL1 were cloned from $CD8^+$ T cells, and immunotherapies using T cells transduced with this TCL1-specific T-cell receptor (TCL1-TCR) were tested. Over ten TCL1-specific T-cell clones were generated from normal donor blood samples. One of the T-cell clones, termed TC1 produced high levels of IFN-γ in response to TCL1-peptide pulsed T2 cells, and was strongly positive by HLA-A2-TCL1 tetramer staining. The TCR from these T cells was cloned by RT-PCR. Sequencing revealed that the TCRs was composed of TCRα (SEQ ID NO:3) and β fragments (SEQ ID NO:4). It was observed that normal donor T cells transduced with TCL1-TCR specifically killed $TCL1_{70-79}$ peptide-pulsed T2 cells but not control T2 cells. Furthermore, these TCL1-TCR-transduced T cells specifically lysed HLA-A2$^+$ TCL1-expressing lymphoma cell lines, primary lymphoma cells, and cell lines from various solid tumors including colon and liver, but not control HLA-A2$^-$ lymphoma tumor cells, indicating that the TCL1 epitope is expressed by cancer cells. Collectively, these data demonstrate that the TCL1-TCR gene provided herein can be used as a specific tool to develop adoptive T-cell therapy strategies against B-cell malignancies as well as solid tumors.

An aspect of the present invention relates to an engineered T cell receptor (TCR) having antigenic specificity for T-cell leukemia/lymphoma 1 (TCL1) or SEQ ID NO:29, wherein the TCR comprises the amino acid sequences of SEQ ID NO: 54, 55, 56, 57, 58, and 59. In some embodiments, the engineered T cell receptor (TCR) comprises: (i) an alpha chain variable region having the amino acid sequence of SEQ ID NO:1 or a sequence having at least 90%, at least 95% or at least 98% sequence identity to SEQ ID NO:1; and/or (ii) a beta chain variable region having the amino acid sequence of SEQ ID NO:2 or a sequence having at least 90%. at least 95% or at least 98% sequence identity to SEQ ID NO:2. The engineered TCR may bind HLA-A2. The engineered TCR may bind HLA-A*0201. In some embodiments, the TCR comprises an alpha chain variable region having at least 95% or at least 98% identity to the amino acid sequence of SEQ ID NO:1 and/or a beta chain variable region having at least 95% or at least 98% identity to the amino acid sequence of SEQ ID NO:2. In some embodiments, the TCR comprises an alpha chain variable region having at least 99% identity to the amino acid sequence of SEQ ID NO:1 and/or a beta chain variable region having at least 95% identity to the amino acid sequence of SEQ ID NO:2. In some embodiments, the TCR comprises an alpha chain variable region having at least 95% identity to the amino acid sequence of SEQ ID NO:1 and/or a beta chain having at least 99% identity to the amino acid sequence of SEQ ID NO:2. In some embodiments, the TCR comprises an alpha chain variable region of SEQ ID NO:1 and/or a beta chain of SEQ ID NO:2. The TCR may comprise an alpha chain having at least 95% identity to the sequence of SEQ ID NO:3 and/or a beta chain having at least 95% identity to the sequence of SEQ ID NO:4. In some embodiments, the TCR comprises an alpha chain comprising the nucleotide sequence of SEQ ID NO:3 and/or a beta chain comprising the nucleotide sequence of SEQ ID NO:4. In some embodiments, the TCR is further defined as a soluble TCR, wherein the soluble TCR does not comprise a transmembrane domain. The TCR may further comprise a detectable label. In some embodiments, the TCR is covalently bound to a therapeutic agent such as, e.g., an immunotoxin or a chemotherapeutic agent.

In some embodiments, the TCR alpha and/or beta chain variable region comprises at least one conservative amino acid substitution compared to SEQ ID NO:1 or SEQ ID NO:2. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc. In some aspects, the TCR alpha and/or beta chain variable regions comprise between 1 and 20, between 1 and 10, between 1 and 5, between 1 and 3, between 2 and 20, between 2 and 10, between 2 and 5, or between 2 and 3 conservative amino acid substitutions compared to SEQ ID NO:1 or SEQ ID NO:2. Alternatively or additionally, the TCR alpha and/or beta chain variable region comprises at least one non-conservative amino acid substitution compared to SEQ ID NO:1 or SEQ ID NO:2. In this case, it is preferable for the non-conservative amino acid substitution to not interfere with or inhibit the biological activity of the TCR. Preferably, the non-conservative amino acid substitution enhances the biological activity of the TCR, such that the biological activity of the TCR is increased as compared to the unmodified TCR. In some aspects, the TCR alpha and/or beta chain variable regions comprise between 1 and 20, between 1 and 10, between 1 and 5, between 1 and 3, between 2 and 20, between 2 and 10, or between 2 and 5 non-conservative amino acid substitutions compared to SEQ ID NO:1 or SEQ ID NO:2.

In other embodiments, an engineered TCR is provided comprising two polypeptide chains, each of which comprises a variable region comprising a complementarity determining region (CDR) 1, a CDR2, and a CDR3 of a TCR, wherein the first polypeptide chain comprises a CDR1 comprising the amino acid sequence TSGFYG (SEQ ID NO: 54; CDR1 of α chain), a CDR2 comprising the amino acid sequence NGLDGL (SEQ ID NO: 55; CDR2 of α chain) and a CDR3 comprising the amino acid sequence LLGSGAGSYQLT (SEQ ID NO: 56; CDR of α chain), and the second polypeptide chain comprises a CDR1 comprising the amino acid sequence SGHKS (SEQ ID NO: 57; CDR1 of β chain), a CDR2 comprising the amino acid sequence YYEKEE (SEQ ID NO: 58; CDR2 of β chain) and a CDR3 comprising the amino acid sequence ASSFTDGGTYEQY (SEQ ID NO: 59; CDR3 of β chain). In this regard, the engineered TCR preferably comprises the amino acid sequence of SEQ ID NOs: 54, 55, 56, 57, 58, and 59.

Another aspect of the present invention relates to a multivalent TCR complex comprising a plurality of TCRs provided herein or as described above. The multivalent TCR may comprise 2, 3, 4 or more TCRs associated with one another. The multivalent TCR may be present in a lipid bilayer, in a liposome, or is attached to a nanoparticle. In some embodiments, the TCRs are associated with one another via a linker molecule. For example, the TCRs may be expressed as single protein comprising a linker peptide linking the α chain and the β chain. The linker peptide may advantageously facilitate the expression of a recombinant TCR in a host cell. Upon expression of the construct, including the linker peptide by a host cell, the linker peptide may be cleaved resulting in separated α and β chains.

Yet another aspect of the present invention relates to a polypeptide encoding a TCR of the present invention or as described above. Another aspect of the present invention relates to a polynucleotide or an isolated nucleic acid comprising a nucleotide sequence encoding a TCR of the present invention or the polypeptide encoding a TCR as described above or herein.

Another aspect of the present invention relates to an expression vector comprising a nucleic acid or nucleotide sequence encoding a TCR, or an alpha and/or beta chain of a TCR, of the present invention or as described above. The sequence encoding the TCR may under the control of or operably linked to an expression control sequence (e.g., a promoter and/or enhancer). In some aspects, the expression control sequence is a tissue specific promoter, preferably a T cell-specific promoter such as a CD4, CD8, TCRα, or TCRβ promoter. In other aspects, the expression control sequence is a constitutive or inducible promoter such as an elongation factor-1α (EF-1α) promoter or a cytomegalovirus (CMV) promoter. In some embodiments, the expression vector is a viral vector (e.g., a retroviral vector or a lentiviral vector). In some embodiments, the vector further encodes a linker domain. The linker domain may be positioned between the alpha chain and beta chain, such that the TCR is expressed as a single protein comprising a linker peptide between the alpha and the beta chain. The linker peptide may advantageously facilitate the expression of a recombinant TCR in a host cell. Upon expression of the construct, including the linker peptide by a host cell, the linker peptide may be cleaved resulting in separated alpha and beta chains. In some embodiments, the linker domain comprises one or more cleavage sites; for example, the cleavage sites may be a furin cleavage site (e.g., RAKR (SEQ ID NO: 30) or ATNFSLLKQAGDVEENPG (SEQ ID NO:31)) and/or a P2A cleavage site. The one or more cleavage sites may be separated by a spacer (e.g., SGSG (SEQ ID NO:32) or GSG).

Yet another aspect of the present invention relates to a host cell engineered to express a TCR of the present invention or as described above. In some embodiments, the cell is a T cell, NK cell, invariant NK cell, NKT cell, mesenchymal stem cell (MSC), or induced pluripotent stem (iPS) cell. The host cell may be an immune cell. The host cell may be isolated from an umbilical cord. In some embodiments, the T cell is a CD8+ T cell, CD4+ T cell, or γδ T cell. In some embodiments, the T cell is a regulatory T cell (Treg). The cell may be autologous or allogeneic. In related aspects, a population of cells is provided comprising at least one host cell engineered to express a TCR as herein described. The population of cells may be a heterogenous population comprising the host cell comprising any of the recombinant expression vectors described herein, in addition to at least one other cell (e.g., a host cell) which does not comprise any of the recombinant expression vectors. Alternatively, the population of cells can be a substantially homogenous population, in which the population comprises mainly host cells comprising the recombinant expression vector. The population can also be a clonal population of cells, in which all cells of the population are clones of a single host cell comprising a recombinant expression vector, such that all cells of the population comprise the recombinant expression vector.

Another aspect of the present invention relates to a method for engineering a host cell to express a TCR as described herein comprising contacting the host (e.g. immune) cell with: (i) a TCR of of the present invention or as described above or (ii) an expression vector encoding a TCRα and/or TCRβ chain as herein described. In some embodiments, the immune cell is a T cell (preferably a CD4+ or CD8+ T cell), or a peripheral blood lymphocyte. In some embodiments, the contacting is further defined as transfecting or transducing. Transfecting may comprise electroporating RNA encoding a TCR of the present invention or as described above into the immune cell. The method may further comprise generating viral supernatant from the expression vector prior to transducing the immune cell. The immune cell may be a stimulated lymphocyte. The stimulated lymphocyte may be a human lymphocyte. In some embodiments, the stimulating comprises contacting the immune cell with or incubating the immune cell in OKT3 and/or IL-2. The method may further comprise sorting the immune cells to isolate TCR engineered T cells, performing T cell cloning by serial dilution, and/or expansion of the T cell clone by the rapid expansion protocol.

Yet another aspect of the present invention relates to a method of treating cancer in a subject comprising administering an effective amount of the TCR-engineered cells of the present invention or as described above to a subject (e.g., a human patient), wherein the cancer expresses TCL1. In some embodiments, the subject is identified to have an HLA-A*0201 allele. In some embodiments, the TCR-engineered cell is a T cell or peripheral blood lymphocyte. The T cell may be a CD8+ T cell, CD4+ T cell, or Treg. The cancer may be a leukemia, a lymphoma, or a B-cell malignancy, or a B-cell lymphoma. In some embodiments, the B-cell malignancy selected from the group consisting of follicular lymphoma (FL), chronic lymphocytic leukemia (CLL), mantle cell lymphoma (MCL), diffuse large B-cell lymphoma (DLBCL), marginal zone lymphoma (MZL), Burkitt lymphoma, hairy cell leukemia, Waldenström macroglobulinemia, lymphoblastic lymphoma, and primary cutaneous B cell lymphoma. The cancer may be a cancer of the brain, colon, liver, pancreas, skin, breast, ovarian, prostate, renal, stomach, bladder, lung, esophagus, cervix, or testis. The cancer may be a solid tumor. The subject may be a human. The TCR engineered cells may be autologous or allogeneic. The method may further comprise lymphodepletion of the subject prior to administration of the TCL1-specific T cells. The lymphodepletion may comprise administration of cyclophosphamide and/or fludarabine. The method may further comprise administering a second anticancer therapy (e.g., a chemotherapy, immunotherapy, surgery, radiotherapy, or biological therapy) to the subject. The second therapy may be an anti-CD19 immunotherapy. The cancer may be a B-cell malignancy or a lymphoma. In some embodiments, the cancer is a solid tumor. The TCR-engineered cells, and/or the at least a second therapeutic agent may be administered intravenously, intraperitoneally, intratracheally, intratumorally, intramuscularly, endoscopically, intralesionally, percutaneously, subcutaneously, regionally, or by direct injection or perfusion. In some embodiments, the subject is determined to have cancer cells which overexpress TCL1.

Another aspect of the present invention relates to a method of treating a cancer in a mammalian subject comprising administering a therapeutically effective amount of a TCL1-targeting immunotherapy to the subject, wherein the cancer is a solid tumor. The solid tumor may be a cancer of the brain, colon, liver, pancreas, skin, breast, ovarian, prostate, renal, stomach, bladder, lung, esophagus, cervix, or testis. The TCL1-targeting immunotherapy may be an anti-TCL1 antibody, or a TCL1-targeting T-cell therapy.

In certain embodiments, the present disclosure provides an engineered T cell receptor (TCR) comprising an alpha chain variable region having at least 90%, such as 91%, 92%, 93%, 94%, 95%, 96%, 97%, 98%, 99%, or 100%, identity to the amino acid sequence of SEQ ID NO: 1 and/or a beta chain variable region having at least 90%, such as 91%, 92%, 93%, 94%, 95%, 96%, 97%, 98%, 99%, or 100%, identity to the amino acid sequence of SEQ ID NO: 2. In these embodiments, the alpha and beta chain preferably includes one or more or all of the CDR regions (e.g., at least CDR3) contained in the SEQ ID NO:1 and SEQ ID NO:2 variable regions. In some aspects, the engineered TCR binds HLA-A2 or HLA-A*0201-TCL1 peptide complexes. In particular aspects, the TCR comprises an alpha chain of SEQ ID NO: 1 and/or a beta chain of SEQ ID NO: 2.

In certain aspects, the TCR comprises an alpha chain having at least 90%, such as 91%, 92%, 93%, 94%, 95%, 96%, 97%, 98%, 99%, or 100%, identity to the amino acid sequence of SEQ ID NO: 3 and/or a beta chain variable region having at least 90%, such as 91%, 92%, 93%, 94%, 95%, 96%, 97%, 98%, 99%, or 100%, identity to the amino acid sequence of SEQ ID NO: 4; wherein the alpha and beta chain would preferably include one or more or all of the CDR regions (e.g., at least CDR3) contained in the SEQ ID NO:1 and SEQ ID NO:2 variable regions. In particular aspects, the TCR may have variation in the sequence of the variable regions of the alpha and/or beta chain while keeping the sequences of the CDR regions constant.

In some aspects, the TCR comprises an alpha chain or alpha chain variable region encoded by a nucleotide sequence having at least 90%, such as 91%, 92%, 93%, 94%, 95%, 96%, 97%, 98%, 99%, or 100%, identity to the nucleotide sequence of SEQ ID NOs: 5 or 7, respectively, and/or a beta chain or beta chain variable region encoded by a nucleotide sequence having at least 90%, such as 91%, 92%, 93%, 94%, 95%, 96%, 97%, 98%, 99%, or 100%, identity to the nucleotide sequence of SEQ ID NO: 6 or 8, respectively. In specific aspects, the TCR comprises an alpha chain or alpha chain variable region encoded by the nucleotide sequence of SEQ ID NO: 5 or 7, respectively, and/or a beta chain or beta chain variable region encoded by the nucleotide sequence of SEQ ID NOs: 6 or 8, respectively.

In certain aspects, the TCR is further defined as a soluble TCR, wherein the soluble TCR does not comprise a transmembrane domain.

In some aspects, the TCR further comprises a detectable label. In certain aspects, the TCR is covalently bound to a therapeutic agent. In specific aspects, the therapeutic agent is an immunotoxin or a chemotherapeutic agent.

Further provided herein is a multivalent TCR complex comprising a plurality of TCRs of the embodiments. In some aspects, the multivalent TCR comprises 2, 3, 4 or more TCRs associated with one another. In particular aspects, the multivalent TCR is present in a lipid bilayer, in a liposome, or is attached to a nanoparticle. In some aspects, the TCRs are associated with one another via a linker molecule.

In another embodiment, there is provided a polypeptide encoding the TCR of the embodiments. Also provided herein is a polynucleotide encoding the polypeptide of the embodiments.

Further embodiments provide an expression vector encoding the TCR of the embodiments. In some aspects, the sequence encoding the TCR is under the control of a promoter. In particular aspects, the expression vector is a viral vector. In one specific aspect, the viral vector is a retroviral vector. In some aspects, the vector further encodes a linker domain. In some aspects, the linker domain is positioned between the alpha chain and beta chain. In certain aspects, the linker domain comprises one or more cleavage sites. In some aspects, the one or more cleavage sites are a Furin cleavage site and/or a P2A cleavage site. In some aspects, the Furin cleavage site is RAKR (SEQ ID NO: 30). In other aspects, the Furin cleavage site is ATNFSLLKQAGDVEENPG (SEQ ID NO: 31). In certain aspects, the one or more cleavage sites are separated by a spacer. In specific aspects, the spacer is SGSG (SEQ ID NO: 32) or GSG.

In another embodiment, there is provided a host cell engineered to express the TCR of the embodiments. In some aspects, the cell is a T cell, NK cell, invariant NK cell, NKT cell, mesenchymal stem cell (MSC), or induced pluripotent stem (iPS) cell. In certain aspects, the host cell is an immune cell. In particular aspects, the host cell is isolated from an umbilical cord. In some aspects, the T cell is a CD8$^+$ T cell, CD4+ T cell, or γδ T cell. In particular aspects, the T cell is a regulatory T cell (Treg). In some aspects, the cell is autologous. In particular aspects, the cell is allogeneic.

A further embodiment provides a method for engineering the host cell of the embodiments comprising contacting said immune cell with the TCR of the embodiments or the expression vector of the embodiments. In some aspects, the immune cell is a T cell or a peripheral blood lymphocyte. In certain aspects, contacting is further defined as transfecting or transducing. In some aspects, transfecting comprises electroporating RNA encoding the TCR of the embodiments into the immune cell.

In additional aspects, the method further comprises generating viral supernatant from the expression vector encoding the TCR of the embodiments prior to transducing the immune cell.

In some aspects, the immune cell is a stimulated lymphocyte. In certain aspects, the stimulated lymphocyte is a human lymphocyte. In certain aspects, stimulating comprises contacting the immune cell with or incubating the immune cell in OKT3 and/or IL-2.

In some aspects, the method further comprises sorting the immune cells to isolate TCR engineered T cells. In certain aspects, the method further comprises performing T cell cloning by serial dilution. In some aspects, the method further comprises expansion of the T cell clone by the rapid expansion protocol.

In another embodiment, there is provided a method of treating cancer in a subject comprising administering an effective amount of the TCR-engineered cells of the embodiments to the subject. In some aspects, the subject is identified to have an HLA-A*0201 allele. In some aspects, the subject is a human.

In certain aspects, the TCR-engineered cell is a T cell or peripheral blood lymphocyte. In specific aspects, the T cell is a CD8$^+$ T cell, CD4$^+$ T cell, or Treg.

In some aspects, the cancer is a melanoma. In particular aspects, the melanoma is a cutaneous melanoma, a uveal melanoma, a mucosal melanoma, or a metastatic melanoma. In certain aspects, the TCR engineered cells are autologous or allogeneic.

In additional aspects, the method further comprises lymphodepletion of the subject prior to administration of the TCL1-specific T cells. In some aspects, lymphodepletion comprises administration of cyclophosphamide and/or fludarabine.

In some aspects, the method further comprises administering a second anticancer therapy. In certain aspects, the therapy is a chemotherapy, immunotherapy, surgery, radiotherapy, or biotherapy. In some aspects, the TCR-engineered cells, and/or the at least a second therapeutic agent are administered intravenously, intraperitoneally, intratracheally, intratumorally, intramuscularly, endoscopically, intralesionally, percutaneously, subcutaneously, regionally, or by direct injection or perfusion. In certain aspects, the subject is determined to have cancer cells which overexpress TCL1.

In related aspects, the method comprises co-administering (sequentially, simultaneously or separately) a second anticancer therapy comprising one or more immune checkpoint inhibitors that bind to and antagonize the activity of an immune checkpoint protein such as, e.g., cytotoxic T-lymphocyte antigen-4 (CTLA4), programmed cell death protein 1 (PD-1) and its ligands PD-L1 and PD-L2, B7-H3, B7-H4, herpesvirus entry mediator (HVEM), T cell membrane protein 3 (TIM3), galectin 9 (GAL9), lymphocyte activation gene 3 (LAG3), V-domain immunoglobulin (Ig)-containing suppressor of T-cell activation (VISTA), Killer-Cell Immunoglobulin-Like Receptor (KIR), B and T lymphocyte attenuator (BTLA), T cell immunoreceptor with Ig and ITIM domains (TIGIT) or a combination thereof. In some preferred embodiments, the immune checkpoint inhibitor is an anti-PD-1, anti-PD-L1, or anti-CLTA4 antibody or antigen-binding fragment thereof or a fusion protein. In some preferred embodiments, the immune checkpoint inhibitor is a monoclonal antibody against CTLA4 such as Ipilimumab (Yervoy®; BMS) or Tremelimumab (AstraZeneca/MedImmune) and/or a monoclonal antibody against PD-1 such as Nivolumab (Opdivo®; Bristol-Myers Squibb; code name BMS-936558), Pembrolizumab (Keytruda®) or Pidilizumab.

In certain embodiments, the present disclosure provides TCR that selectively bind TCL1. In some embodiments, the alpha and beta portions of a TCR sequence provided herein may be included in a chimeric antigen receptor (CAR) that may be used in an adoptive T cell therapy. In some embodiments, the alpha and beta portions of the TCR may be encoded in a DNA that can be used, e.g., to treat a lymphoma. Alternately, the alpha and beta variable regions of the TCR may be included in a protein, such as a TCR or a solubilized protein, and used in an anti-cancer therapy such as an adoptive immunotherapy. In some preferred embodiments, the TCR, CAR, or soluble peptide selectively binds TCL1 at a particular epitope, such as TCL1$_{65-79}$ immunogenic epitopes. It is anticipated that the TCR may result in a reduction in toxicity towards non-cancerous cells and may be particularly useful for the treatment of B-cell malignancies. In some embodiments, the cloned T cell receptors may be included in a chimeric T cell receptor (CAR) and used in an adoptive T cell transfer or immunotherapy.

In some aspects, the present disclosure provides soluble TCRs that can be used to treat HLA-A2 positive cancer patients directly. The soluble bispecific T cell-engaging molecules can be generated by linking the TCL1-TCR to CD3-specific Fab fragments. The T cell-engaging TCR can bind the tumor cell surface by presenting the respective peptide/MHC complex and the Fab fragments then crosslink TCRs on the surface of antigen-experienced CD8+ T cells, resulting in cellular activation and elimination of the target cell. Thus, this soluble bispecific TCR constructs can be used for treating the cancer patients directly.

Finally, the soluble TCR can be used as a probe for diagnostic evaluation of peptide/MHC in tumor cells or to direct therapeutic molecules to the tumor site. This soluble TCR molecule also could be labeled with tracers such as a fluorescent probe or radioactive probe, and then used for diagnostic evaluation of the presentation of peptide/MHC in tumor cells. Furthermore, this soluble TCR molecule could be linked with therapeutic molecules, such as a toxin, so as to direct these therapeutic molecules to the tumor sites for the treatment of cancer patients.

In certain aspects, the TCL1-specific T cells, optionally in combination with a second therapeutic agent, can be administered intravenously, intraperitoneally, intratracheally, intratumorally, intramuscularly, endoscopically, intralesionally, percutaneously, subcutaneously, regionally, or by direct injection or perfusion.

Yet another aspect of the present invention relates to a pharmaceutical composition comprising the peptide of the present invention or as described above and an excipient. The pharmaceutical preparation may be formulated for parenteral administration, intravenous injection, intramuscular injection, inhalation, or subcutaneous injection. In some embodiments, the peptide is comprised in a liposome, lipid-containing nanoparticle, or in a lipid-based carrier.

Another aspect of the present invention relates to particular T cell receptor variable regions (e.g., SEQ ID NO: 1 and 2).

In various aspects an immunotherapy involving a TCL1-TCR as disclosed herein may be used to treat a variety of cancers, including a leukemia, a lymphoma, or a B-cell malignancy, or a B-cell lymphoma. In some embodiments, the cancer is a B-cell malignancy selected from the group consisting of follicular lymphoma (FL), chronic lymphocytic leukemia (CLL), mantle cell lymphoma (MCL), diffuse large B-cell lymphoma (DLBCL), and splenic marginal zone lymphoma (SMZL). As shown in the examples below, TCL1-TCR may be used to treat or specifically target a cancer or solid tumor expressing TCL1, such as a cancer of the brain, colon, liver, pancreas, skin, breast, ovarian, prostate, renal, stomach, bladder, lung, esophagus, cervix, or testis.

Various embodiments of the present invention can be understood by the following numbered sentences:

1. An engineered T cell receptor (TCR) comprising: (i) an alpha chain variable region having the amino acid sequence of SEQ ID NO:1 or a sequence having at least 90% sequence identity to SEQ ID NO:1; and/or (ii) a beta chain variable region having the amino acid sequence of SEQ ID NO:2 or a sequence having at least 90% sequence identity to SEQ ID NO:2.
2. The TCR of sentence 1, wherein the engineered TCR binds HLA-A2.
3. The TCR of sentence 2, wherein the engineered TCR binds HLA-A*0201.
4. The TCR of sentence 4, wherein the TCR comprises an alpha chain variable region having at least 95% identity to the amino acid sequence of SEQ ID NO:1 and/or a beta chain variable region having at least 95% identity to the amino acid sequence of SEQ ID NO:2.
5. The TCR of sentence 4, wherein the TCR comprises an alpha chain variable region having at least 99% identity to the amino acid sequence of SEQ ID NO:1 and/or a beta chain variable region having at least 95% identity to the amino acid sequence of SEQ ID NO:2.
6. The TCR of sentence 4, wherein the TCR comprises an alpha chain variable region having at least 95% identity to the amino acid sequence of SEQ ID NO:1 and/or a beta chain having at least 99% identity to the amino acid sequence of SEQ ID NO:2.
7. The TCR of sentence 1, wherein the TCR comprises an alpha chain variable region of SEQ ID NO:1 and/or a beta chain of SEQ ID NO:2.
8. The TCR of sentence 4, wherein the TCR comprises an alpha chain having at least 95% identity to the sequence of SEQ ID NO:3 and/or a beta chain having at least 95% identity to the sequence of SEQ ID NO:4.
9. The TCR of sentence 4, wherein the TCR comprises an alpha chain comprising the sequence of SEQ ID NO:3 and/or a beta chain comprising the sequence of SEQ ID NO:4.
10. The TCR of sentence 1, wherein the TCR is further defined as a soluble TCR, wherein the soluble TCR does not comprise a transmembrane domain.
11. The TCR of any one of sentences 1-10, further comprising a detectable label.
12. The TCR of any one of sentence 1-10, wherein the TCR is covalently bound to a therapeutic agent.
13. The TCR of sentence 12, wherein the therapeutic agent is an immunotoxin or a chemotherapeutic agent.
14. A multivalent TCR complex comprising a plurality of TCRs according to any one of sentences 1-10.
15. The complex of sentence 14, wherein the multivalent TCR comprises 2, 3, 4 or more TCRs associated with one another.
16. The complex of sentence 15, wherein the multivalent TCR is present in a lipid bilayer, in a liposome, or is attached to a nanoparticle.
17. The complex of sentence 15, wherein the TCRs are associated with one another via a linker molecule.
18. A polypeptide encoding the TCR of any one of sentences 1-17.
19. A polynucleotide encoding the polypeptide of sentence 18.
20. An expression vector encoding the TCR of any one of sentences 1-17.
21. The expression vector of sentence 20, wherein the sequence encoding the TCR is under the control of a promoter.
22. The expression vector of sentence 20, wherein the expression vector is a viral vector.
23. The expression vector of sentence 22, wherein the viral vector is a retroviral vector.
24. The expression vector of sentence 20, wherein the vector further encodes a linker domain.
25. The expression vector of sentence 24, wherein the linker domain is positioned between the alpha chain and beta chain.
26. The expression vector of sentence 24, wherein the linker domain comprises one or more cleavage sites.
27. The expression vector of sentence 26, wherein the one or more cleavage sites are a furin cleavage site and/or a P2A cleavage site.
28. The expression vector of sentence 27, wherein the furin cleavage site is RAKR (SEQ ID NO: 30).

29. The expression vector of sentence 27, wherein the Furin cleavage site is ATNFSLLKQAGDVEENPG (SEQ ID NO:31).
30. The expression vector of sentence 24, wherein the one or more cleavage sites are separated by a spacer.
31. The expression vector of sentence 30, wherein the spacer is SGSG (SEQ ID NO:32) or GSG.
32. A host cell engineered to express the TCR of any one of sentences 1-10.
33. The host cell of sentence 32, wherein the cell is a T cell, NK cell, invariant NK cell, NKT cell, mesenchymal stem cell (MSC), or induced pluripotent stem (iPS) cell.
34. The host cell of sentence 32, wherein the host cell is an immune cell.
35. The host cell of sentence 32, wherein the host cell is isolated from an umbilical cord.
36. The host cell of sentence 33, wherein the T cell is a $CD8^+$ T cell, CD4+ T cell, or γδ T cell.
37. The host cell of sentence 33, wherein the T cell is a regulatory T cell (Treg).
38. The host cell of sentence 32, wherein the cell is autologous.
39. The host cell of sentence 32, wherein the cell is allogeneic.
40. A method for engineering the host cell of sentence 32 comprising contacting said immune cell with the TCR of any one of sentences 1-10 or the expression vector of any one of sentences 20-31.
41. The method of sentence 40, wherein the immune cell is a T cell, or a peripheral blood lymphocyte.
42. The method of sentence 40, wherein the contacting is further defined as transfecting or transducing.
43. The method of any one of sentences 40-42, wherein transfecting comprises electroporating RNA encoding the TCR of any one of sentences 1-10 into the immune cell.
44. The method of any one of sentences 42, further comprising generating viral supernatant from the expression vector of sentence 20 prior to transducing the immune cell.
45. The method of any one of sentences 40-44, wherein the immune cell is a stimulated lymphocyte.
46. The method of sentence 45, wherein the stimulated lymphocyte is a human lymphocyte.
47. The method of sentence 45, wherein the stimulating comprises contacting the immune cell with or incubating the immune cell in OKT3 and/or IL-2.
48. The method of any one of sentences 40-47, further comprising sorting the immune cells to isolate TCR engineered T cells.
49. The method of sentence 48, further comprising performing T cell cloning by serial dilution.
50. The method of sentence 49, further comprising expansion of the T cell clone by the rapid expansion protocol.
51. A method of treating cancer in a subject comprising administering an effective amount of the TCR-engineered cells of any one of sentences 32-38 to a subject, wherein the cancer expresses TCL1.
52. The method of sentence 51, wherein the subject is identified to have an HLA-A*0201 allele.
53. The method of sentence 51, wherein the TCR-engineered cell is a T cell or peripheral blood lymphocyte.
54. The method of sentence 51, wherein the T cell is a $CD8^+$ T cell, CD4+ T cell, or Treg.
55. The method of sentence 51, wherein the cancer is a leukemia, a lymphoma, or a B-cell malignancy, or a B-cell lymphoma.
56. The method of sentence 55, wherein the B-cell malignancy selected from the group consisting of follicular lymphoma (FL), chronic lymphocytic leukemia (CLL), mantle cell lymphoma (MCL), diffuse large B-cell lymphoma (DLBCL), and marginal zone lymphoma (MZL).
57. The method of sentence 51, wherein the cancer is a cancer of the brain, colon, liver, pancreas, skin, breast, ovarian, prostate, renal, stomach, bladder, lung, esophagus, cervix, or testis.
58. The method of sentence 51, wherein the cancer is a solid tumor.
59. The method of sentence 51, wherein the subject is a human.
60. The method of sentence 51, wherein the TCR engineered cells are autologous or allogeneic.
61. The method of sentence 51, further comprising lymphodepletion of the subject prior to administration of the TCL1-specific T cells.
62. The method of sentence 61, wherein the lymphodepletion comprises administration of cyclophosphamide and/or fludarabine.
63. The method of any one of sentences 51-62, further comprising administering a second anticancer therapy to the subject.
64. The method of sentence 63, wherein the second therapy is a chemotherapy, immunotherapy, surgery, radiotherapy, or biological therapy.
65. The method of sentence 64, wherein the second therapy is an anti-CD19 immunotherapy.
66. The method of sentence 65, wherein the cancer is a B-cell malignancy or a lymphoma.
67. The method of sentence 65, wherein the cancer is a solid tumor.
68. The method of any one of sentences 51-63, wherein the TCR-engineered cells, and/or the at least a second therapeutic agent are administered intravenously, intraperitoneally, intratracheally, intratumorally, intramuscularly, endoscopically, intralesionally, percutaneously, subcutaneously, regionally, or by direct injection or perfusion.
69. The method of any one of sentences 51-68, wherein the subject is determined to have cancer cells which overexpress TCL1.
70. A method of treating a cancer in a mammalian subject comprising administering a therapeutically effective amount of a TCL1-targeting immunotherapy to the subject, wherein the cancer is a solid tumor.
71. The method of sentence 70, wherein the solid tumor is a cancer of the brain, colon, liver, pancreas, skin, breast, ovarian, prostate, renal, stomach, bladder, lung, esophagus, cervix, or testis.
72. The method of any one of sentences 70-71, wherein the TCL1-targeting immunotherapy is an anti-TCL1 antibody, or a TCL1-targeting T-cell therapy.

The term "chimeric antigen receptors (CARs)," as used herein, may refer to artificial T cell receptors, chimeric T cell receptors, or chimeric immunoreceptors, for example, and encompass engineered receptors that graft an artificial specificity onto a particular immune effector cell. CARs may be employed to impart the specificity of a monoclonal antibody onto a T cell, thereby allowing a large number of specific T cells to be generated, for example, for use in adoptive cell therapy. In specific embodiments, CARs direct specificity of the cell to a tumor associated antigen, for example. In some embodiments, CARs comprise an intracellular activation domain, a transmembrane domain, and an extracellular domain comprising a tumor associated antigen binding region. In particular aspects, CARs comprise fusions of single-chain variable fragments (scFv) derived from monoclonal antibodies, fused to CD3-zeta a transmembrane domain and endodomain. The specificity of other CAR designs may be derived from ligands of receptors (e.g., peptides) or from pattern-recognition receptors, such as Dectins. In certain cases, the spacing of the antigen-recognition domain can be modified to reduce activation-induced cell death. In certain cases, CARs comprise domains for additional co-stimulatory signaling, such as CD3ζ, FcR, CD27, CD28, CD137, DAP10, and/or OX40. In some cases, molecules can be co-expressed with the CAR, including co-stimulatory molecules, reporter genes for imaging (e.g., for positron emission tomography), gene products that conditionally ablate the T cells upon addition of a pro-drug, homing receptors, chemokines, chemokine receptors, cytokines, and cytokine receptors.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

HLA-A2 refers to the human leukocyte antigen serotype A2 and is also referred to as HLA-A*02. Several serotypes of the gene products of many HLA-A*02 alleles are well known, including HLA-A*0201, *0202, *0203, *0206, *0207, and *0211 gene products.

The terms "inhibiting," "reducing," or "prevention," or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the invention, and vice versa. Furthermore, compositions of the invention can be used to achieve methods of the invention.

Throughout this application, the term "about" is used to indicate that a value includes the inherent variation of error for the device, the method being employed to determine the value, or the variation that exists among the study subjects.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A, IFN-γ ELISA assay of TC1 T clone against TCL1 peptide pulsed T2 cells. FIG. 1B, Tetramer staining of TC1 T clone. FIG. 1C, Information of TC1 TCRαβ chain sequence.

FIG. 2A. Vector design for expression of TCL1-TCR TRB and TRA by lentivirus. FIG. 2B, TRBV antibody and tetramer staining of TCL1-TCR-transduced J76 cells by flow assay. FIG. 2C, IL-2 ELISA assay of TCL1-TCR-transduced or un-transduced J76 cells. FIG. 2D, Avidity assay of TCL1-TCR-transduced J76 cells by IL-2 ELISA.

FIG. 3A, TRBV5-5 and tetramer staining of TCL1-TCR-transduced primary T cells by flow cytometry. FIG. 3B, IL-2 and IFN-γ production by TCL1-TCR-transduced primary T cells against $TCL1_{70-79}$ peptide pulsed T2 cells. FIG. 3C, Cytokine production by TCL1-TCR-transduced CD8 or CD4 T cells against $TCL1_{70-79}$ peptide pulsed T2 cells. FIG. 3D, Avidity assay of TCL1-TCR-transduced primary T cells against different concentration $TCL1_{70-79}$ peptide pulsed T2 cells by IL-2 ELISA.

FIG. 4A, TCL1-TCR-transduced primary T cells against $TCL1_{70-79}$ peptide pulsed T2 cells. FIG. 4B, Cytotoxicity assay of TCL1-TCR-transduced primary T cells against TCL1-expressing, HLA A2+/A2− lymphoma cell lines. FIG. 4C, Cytotoxicity assay of TCL1-TCR-transduced primary T cells against TCL1-expressing, HLA A2+ primary lymphoma cells or normal B cells obtained from the same patients.

FIG. 5A, In vivo luciferase assay of Mino cells in Winn assay. FIG. 5B, TCL1-TCR-transduced T cells significantly extended the survival of experimental mice in Winn assay. FIG. 5C, In vivo luciferase assay of TCL1-TCR-transduced T cells against Mino cells in day 12 adoptive transfer assay. FIG. 5D, TCL1-TCR-transduced T cells significantly extended the survival of experimental mice in adoptive transfer assay.

FIG. 6C, the expression of TCL1 in various tissues and tumors from TCGA database is shown.

FIG. 7C, Cytotoxicity assay of TCL1-TCR-transduced primary T cells against HCT-15, SW480, HepG2 solid tumor cell lines.

FIGS. 8A-C: Safety assay of TCL1-TCR-T. FIG. 8A, Alanine and Glycine replacement of TCL1 70-79 epitope. FIG. 8B, The IL-2 ELISA assay of TCL1-TCR-transduced J76 against T2 cells pulsed with Alanine or Glycine replaced TCL1 70-79 peptide. FIG. 8C, the IL-2 ELISA assay of TCL1-TCR-transduced primary T cells against T2 cell pulsed with Alanine or Glycine replaced TCL1 70-79 peptide.

FIG. 9A, The expression of TCL1 in lymphoma, solid tumor cell lines and normal T cells. Intracellular staining was performed to measure the TCL1 expression in lymphoma, solid tumor cells and normal T cells. C33A, Cervix cancer; A498, renal cancer; KATO-III, stomach cancer; TccSUP, bladder cancer; LnCap, prostate cancer; Mel624, skin cancer; SW480, SW620, colon cancer; U87, U373, brain cancer; MDA-231, breast cancer; WM793, skin cancer; HCT-15, colon cancer; MCF-7, breast cancer; Tera, testis cancer; A498, Kidney cancer; OVCAR3, ovary cancer; Panc-1, pancreas cancer; HepG2, liver cancer; OE33, esophagus cancer; H1650, lung cancer; FB41 T, FB50 T, D403 T, KM19 T, normal donor T cells. Daudi, Jeko-1, Mino, Raji, B-cell lymphoma cells. The relative expression was calculated as: Relative expression=TCL1 MFI–Isotype MFI. FIG. 9B, Overexpression of TCL1 in lymphoma cells. TCL1 protein level was analyzed by intracellular staining assay in lymphoma cell lines (Daudi, Mino, Jeko-1 and Raji). Normal donor-derived T cells (T1 and T2) were used as negative control. Data showed that TCL1 is overexpressed in lymphoma cells but not normal donors' T cells.

FIG. 11: TCL1-TCR alpha and beta DNA sequences are shown. The variable regions in the alpha and beta chains are underlined. (SEQ ID NO: 5=encoding the alpha variable region; SEQ ID NO: 6=encoding the beta variable region; SEQ ID NO: 7=encoding the entire alpha region of TCR; SEQ ID NO: 8=encoding the entire beta region of TCR).

FIG. 12: TCL1-TCR alpha and beta protein sequences are shown. The variable regions in the alpha and beta chains are underlined. (SEQ ID NO: 1=alpha variable region; SEQ ID NO: 2=beta variable region; SEQ ID NO: 3=entire alpha region of TCR; SEQ ID NO: 4=entire beta region of TCR).

FIG. 13: TCL1-TCR alpha and beta sequences are shown. CDR1, CDR2, CDR3 sequences of TCL1-TCR alpha and beta sequence are underlined.

DESCRIPTION OF ILLUSTRATIVE EMBODIMENTS

I. Engineered Antigen Receptors

Figure 1A:
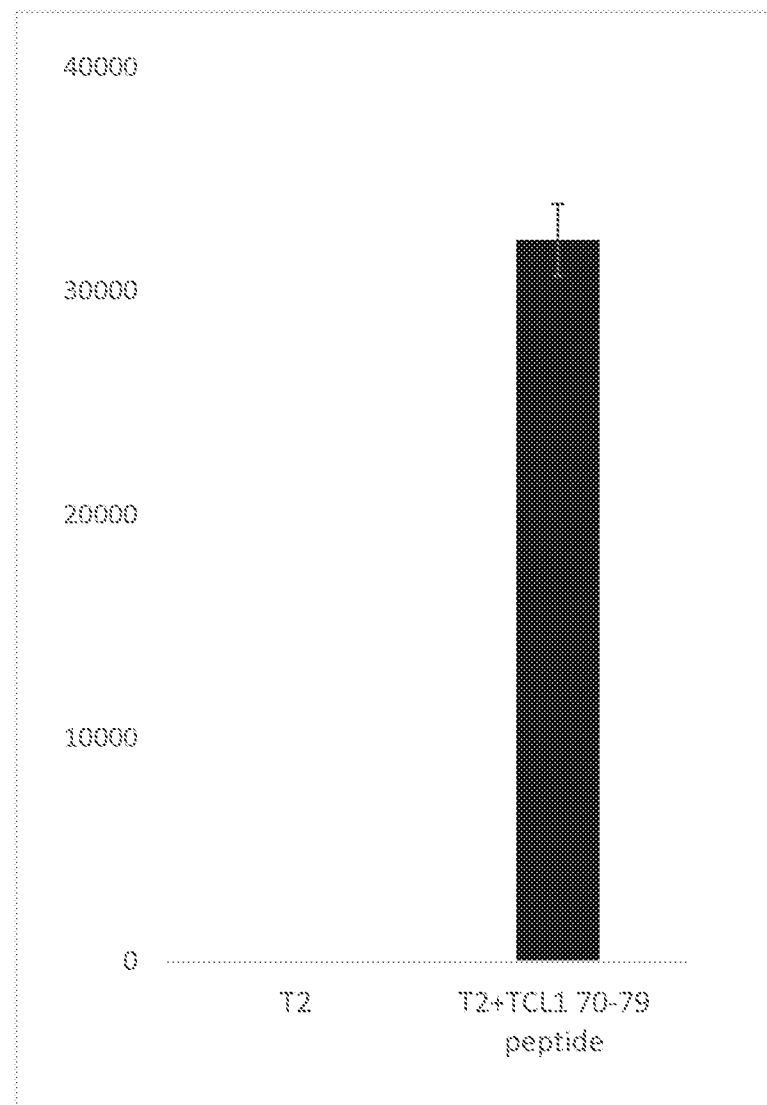
FIGS. 1A-C: Characterization of TCL1-specific T cell clone and cloning of the TC1 TCR α and β genes.

In various aspects, T cell receptors (TCR) are provided that specifically bind TCL1 or a TCL1$_{70-79}$ peptide (SEQ ID NO:29). The antigen binding region of the TCR may be included in a chimeric antigen receptor (CAR) as the extracellular domain comprising an antigen binding region. In some aspects, the TCR is an isolated or purified TCR. The TCR may be transfected into cells (e.g., autologous or allogeneic cells) that may be used in an adoptive cell transfer therapy. In some embodiments, the CAR is humanized to reduce immunogenicity (hCAR).

T-cell leukemia/lymphoma Antigen1 (TCL1) is a B-cell oncoprotein that is overexpressed in multiple forms of B-cell lymphoma. As shown in the below examples, the TCL1-specific TCR gene when transduced into T cells re-directed the T cells to specifically lyse TCL1$_{70-79}$ peptide-pulsed but not control peptide-pulsed T2 cells. The TCR-transduced CD8+ T cells efficiently lysed HLA-0201+, TCL1-expressing human lymphoma cell lines and primary lymphoma cells, but not normal B cells. Adoptive transfer of TCR-transduced T cells into the tumor-engrafted mouse model inhibited the tumor growth and significantly extended the survival of mice. In addition, it was observed that TCL1 is expressed in the human embryonic stem cells and multiple forms of solid tumor cells. The TCR-transduced T cells can successfully lyse the solid tumor cells but not control tumor cells as observed by in vitro assays. Collectively, the data demonstrate that the TCL1-specific TCR-based immunotherapies using the TCR provided herein may be used to treat human B-cell malignancies such as lymphomas and other non-hematological tumors that express TCL1.

The TCL1 oncoprotein exhibits restricted expression in embryonic and normal adult tissues but aberrant expression in >90% of CLL, MCL, follicular lymphoma (FL), DLBCL, and other B-cell lymphomas (Herling et al., 2007; Weng et al., 2012; Aggarwal et al., 2008). It has been shown to promote malignant cell proliferation and survival by co-activating Akt (Teitell, 2005). Moreover, high levels of TCL1 expression were associated with adverse clinical outcome in CLL, MCL, and DLBCL suggesting that TCL1 may be pathogenetically causal in these malignancies (Herling et al., 2007; Aggarwal et al., 2008; Herling et al., 2009; Ramuz et al., 2005). In direct analysis of the consequence of TCL1 overexpression, transgenic (Tg) mice that ectopically express human TCL1 in B cells (Eμ-TCL1$^{Tg}$) develop a lymphoproliferative disease similar to human CLL as well as other forms of B-cell lymphomas which strongly implicates a tumorigenic role for TCL1 (Bichi et at, 2002; Hoyer et al., 2002). To test whether TCL1 can be a target for B-cell lymphoma immunotherapy, an immunogenic HLA-A2-binding T-cell epitope derived from TCL1 that can induce cytotoxic T cells in both HLA-A2$^+$ normal donors and lymphoma patients was identified (Weng et al., 2012). The TCL1$_{65-79}$ peptide-specific CTLs specifically lysed the HLA-A2+, TCL1-expressing B-cell lymphomas but not normal B cells, indicating the epitope can be used as a valid target for the immunotherapy of B-cell lymphomas.

In some embodiments, host cells such as, e.g., T cells (e.g., CD4$^+$ T cells, CD8$^+$ T cells, γδ T cells, and Tregs), NK cells, invariant NK cells, NKT cells, mesenchymal stem cells (MSCs), or induced pluripotent stem (iPS) cells of the present disclosure can be genetically engineered to express antigen receptors such as engineered TCRs and/or chimeric antigen receptors (CARs). For example, the autologous or allogeneic cells (e.g., isolated from an umbilical cord) are modified to express a T cell receptor (TCR) having antigenic specificity for a cancer antigen. In particular embodiments, the antigen receptors have antigenic specificity for TCL1 or a TCL1$_{70-79}$ peptide (SLLPIMWQLY; SEQ ID NO:29). In certain embodiments, the engineered TCR has an alpha chain comprising an amino acid sequence having least 90, 91, 92, 93, 94, 95, 96, 97, 98, 99, or 100% sequence identity to SEQ ID NO:1 and/or a beta chain comprising an amino acid sequence having at least 90, 91, 92, 93, 94, 95, 96, 97, 98, 99, or 100% sequence identity to SEQ ID NO:2. In some embodiments, the TCR has an alpha chain with at least 90, 91, 92, 93, 94, 95, 96, 97, 98, 99, or 100% sequence identity to SEQ ID NO:3 and/or a beta chain with at least 90, 91, 92, 93, 94, 95, 96, 97, 98, 99, or 100% sequence identity to SEQ ID NO 4. Suitable methods of modification are known in the art. See, for instance, Sambrook and Ausubel, supra. For example, the T cells may be transduced to express a T cell receptor (TCR) having antigenic specificity for a cancer antigen using transduction techniques described in Heemskerk et al., 2008 and Johnson et al., 2009.

Electroporation of RNA coding for the full length TCR α and β (or γ and δ) chains can be used as alternative to overcome long-term problems with autoreactivity caused by pairing of retrovirally transduced and endogenous TCR chains. Even if such alternative pairing takes place in the transient transfection strategy, the possibly generated autoreactive T cells will typically lose this autoreactivity after some time, because the introduced TCR α and β chain are only transiently expressed. When the introduced TCR α and β chain expression is diminished, only normal autologous T cells are left. This is not the case when full length TCR chains are introduced by stable retroviral transduction, which do not lose the introduced TCR chains, causing a constantly present autoreactivity in the patient.

Exemplary antigen receptors, including CARs and recombinant TCRs, as well as methods for engineering and introducing the receptors into cells, include those described, for example, in international patent application publication numbers WO2000/14257, WO2013/126726, WO2012/129514, WO2014/031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., 2013; Davila et al., 2013; Turtle et al., 2012; Wu et al., 2012. In some aspects, the genetically engineered antigen receptors include a CAR as described in U.S. Pat. No. 7,446,190, and those described in International Patent Application Publication No.: WO2014/055668 A1.

A. T Cell Receptor (TCR)

In some embodiments, the genetically engineered antigen receptors include recombinant T cell receptors (TCRs) and/or TCRs cloned from naturally occurring T cells. A "T cell receptor" or "TCR" refers to a molecule that contains a variable a and β chains (also known as TCRα and TCRβ, respectively) or a variable γ and δ chains (also known as TCRγ and TCRδ, respectively) and that is capable of specifically binding to an antigen peptide bound to a MHC receptor. In some embodiments, the TCR is in the αβ form. In certain embodiments, the engineered TCR has an alpha chain variable region of SEQ ID NO:1 and/or a beta chain variable region of SEQ ID NO:2. In some embodiments, the TCR has an alpha chain of SEQ ID NO:3 and a beta chain of SEQ ID NO:4, respectively.

Typically, TCRs that exist in αβ and γδ forms are generally structurally similar, but T cells expressing them may have distinct anatomical locations or functions. A TCR can be found, e.g., on the surface of a cell or in soluble form. Generally, a TCR is found on the surface of T cells (or T lymphocytes) where it is generally responsible for recognizing antigens bound to major histocompatibility complex (MHC) molecules. In some embodiments, a TCR also can contain a constant domain, a transmembrane domain and/or a short cytoplasmic tail (see, e.g., Janeway et al, Immunobiology: The Immune System in Health and Disease, 3$^{rd}$ Ed., Current Biology Publications, p. 433, 1997). For example, in some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction. Unless otherwise stated, the term "TCR" should be understood to encompass functional TCR fragments thereof. The term also encompasses intact or full-length TCRs, including TCRs in the αβ form or γδ form.

Thus, for purposes herein, reference to a TCR includes any TCR or functional fragment, such as an antigen-binding portion of a TCR that binds to a specific antigenic peptide bound in an MHC molecule, i.e. MHC-peptide complex. An "antigen-binding portion" or antigen-binding fragment" of a TCR, which can be used interchangeably, refers to a molecule that contains a portion of the structural domains of a TCR, but that binds the antigen (e.g. MHC-peptide complex) to which the full TCR binds. In some cases, an antigen-binding portion contains the variable domains of a TCR, such as variable a chain and variable β chain of a TCR, sufficient to form a binding site for binding to a specific MHC-peptide complex, such as generally where each chain contains three complementarity determining regions.

In some embodiments, the variable domains of the TCR chains associate to form loops, or complementarity determining regions (CDRs) analogous to immunoglobulins, which confer antigen recognition and determine peptide specificity by forming the binding site of the TCR molecule and determine peptide specificity. Typically, like immunoglobulins, the CDRs are separated by framework regions (FRs) (see, e.g., Jores et al., 1990; Chothia et al., 1988; see also Lefranc et al., 2003). In some embodiments, CDR3 is the main CDR responsible for recognizing processed antigen, although CDR1 of the alpha chain has also been shown to interact with the N-terminal part of the antigenic peptide, whereas CDR1 of the beta chain interacts with the C-terminal part of the peptide. CDR2 is thought to recognize the MHC molecule. In some embodiments, the variable region of the β-chain can contain a further hypervariability (HV4) region.

In some embodiments, the TCR chains contain a constant domain. For example, like immunoglobulins, the extracellular portion of TCR chains (e.g., a-chain, β-chain) can contain two immunoglobulin domains, a variable domain (e.g., $V_a$ or Vβ; typically amino acids 1 to 116 based on Kabat numbering Kabat et al., "Sequences of Proteins of Immunological Interest, US Dept. Health and Human Services, Public Health Service National Institutes of Health, 1991, 5$^{th}$ ed.) at the N-terminus, and one constant domain (e.g., a-chain constant domain or $C_a$, typically amino acids 117 to 259 based on Kabat, β-chain constant domain or Cβ, typically amino acids 117 to 295 based on Kabat) adjacent to the cell membrane. For example, in some cases, the extracellular portion of the TCR formed by the two chains contains two membrane-proximal constant domains, and two membrane-distal variable domains containing CDRs. The constant domain of the TCR domain contains short connecting sequences in which a cysteine residue forms a disulfide bond, making a link between the two chains. In some embodiments, a TCR may have an additional cysteine residue in each of the α and β chains such that the TCR contains two disulfide bonds in the constant domains.

In some embodiments, the TCR chains can contain a transmembrane domain. In some embodiments, the transmembrane domain is positively charged. In some cases, the TCR chains contains a cytoplasmic tail. In some cases, the structure allows the TCR to associate with other molecules like CD3. For example, a TCR containing constant domains with a transmembrane region can anchor the protein in the cell membrane and associate with invariant subunits of the CD3 signaling apparatus or complex.

Generally, CD3 is a multi-protein complex that can possess three distinct chains (γ, δ, and ε) in mammals and the ζ-chain. For example, in mammals the complex can contain a CD3γ chain, a CD3δ chain, two CD3ε chains, and a homodimer of CD3ζ chains. The CD3γ, CD3δ, and CD3ε chains are highly related cell surface proteins of the immunoglobulin superfamily containing a single immunoglobulin domain. The transmembrane regions of the CD3γ, CD3δ, and CD3ε chains are negatively charged, which is a characteristic that allows these chains to associate with the positively charged T cell receptor chains. The intracellular tails of the CD3γ, CD3δ, and CD3ε chains each contain a single conserved motif known as an immunoreceptor tyrosine-based activation motif or ITAM, whereas each CD3ζ chain has three. Generally, ITAMs are involved in the signaling capacity of the TCR complex. These accessory molecules have negatively charged transmembrane regions and play a role in propagating the signal from the TCR into the cell. The CD3- and ζ-chains, together with the TCR, form what is known as the T cell receptor complex.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds. In some embodiments, a TCR alpha and a TCR beta chain comprise a disulfide bond between the alpha and beta chains, said disulfide bond being one which has no equivalent in native alpha-beta T cell receptors (i.e., a non-naturally occurring disulfide bond). In some embodiments, a TCR for a target antigen (e.g., a cancer antigen) is identified and introduced into the cells. In some embodiments, a nucleic acid encoding the TCR can be obtained from a variety of sources, such as by polymerase chain reaction (PCR) amplification of a TCR DNA sequences. In some embodiments, the TCR or antigen-binding portion thereof can be synthetically generated from knowledge of the sequence of the TCR.

B. Chimeric T Cell Receptors

In some embodiments, the engineered antigen receptors include chimeric antigen receptors (CARs), including activating or stimulatory CARs, costimulatory CARs (see WO2014/055668), and/or inhibitory CARs (iCARs, see Fedorov et al., 2013). The CARs generally include an extracellular antigen (or ligand) binding domain linked to one or more intracellular signaling components, in some aspects via linkers and/or transmembrane domain(s). Such molecules typically mimic or approximate a signal through a natural antigen receptor, a signal through such a receptor in combination with a costimulatory receptor, and/or a signal through a costimulatory receptor alone. In some embodiments, the CAR includes an antigen-binding portion or portions of an antibody molecule, such as a single-chain antibody fragment (scFv) derived from the variable heavy (VH) and variable light (VL) chains of a monoclonal antibody (mAb).

The arrangement of the antigen-binding domain of a CAR may be multimeric, such as a diabody or multimers. The multimers can be formed by cross pairing of the variable portions of the light and heavy chains into what may be referred to as a diabody. The hinge portion of the CAR may in some embodiments be shortened or excluded (i.e., generating a CAR that only includes an antigen binding domain, a transmembrane region and an intracellular signaling domain). A multiplicity of hinges may be used with the present invention, e.g., as shown in Table 1. In some embodiments, the hinge region may have the first cysteine maintained, or mutated by a proline or a serine substitution, or be truncated up to the first cysteine. The Fc portion may be deleted from scFv used to as an antigen-binding region to generate CARs according to the present invention. In some embodiments, an antigen-binding region may encode just one of the Fc domains, e.g., either the CH2 or CH3 domain from human immunoglobulin. One may also include the hinge, CH2, and CH3 region of a human immunoglobulin that has been modified to improve dimerization and oligermerization. In some embodiments, the hinge portion of may comprise or consist of an 8-14 amino acid peptide (e.g., a 12 AA peptide), a portion of CD8α, or the IgG4 Fc. In some embodiments, the antigen binding domain may be suspended from cell surface using a domain that promotes oligomerization, such as CD8 alpha. In some embodiments, the antigen binding domain may be suspended from cell surface using a domain that is recognized by monoclonal antibody (mAb) clone 2D3 (mAb clone 2D3 described, e.g., in Singh et al., 2008).

The endodomain or intracellular signaling domain of a CAR can generally cause or promote the activation of at least one of the normal effector functions of an immune cell comprising the CAR. For example, the endodomain may promote an effector function of a T cell such as, e.g., cytolytic activity or helper activity including the secretion of cytokines. The effector function in a naive, memory, or memory-type T cell may include antigen-dependent proliferation. The terms "intracellular signaling domain" or "endodomain" refers to the portion of a CAR that can transduce the effector function signal and/or direct the cell to perform a specialized function. While usually the entire intracellular signaling domain may be included in a CAR, in some cases a truncated portion of an endodomain may be included. Generally, endodomains include truncated endodomains, wherein the truncated endodomain retains the ability to transduce an effector function signal in a cell.

In some embodiments, an endodomain comprises the zeta chain of the T cell receptor or any of its homologs (e.g., eta, delta, gamma, or epsilon), MB1 chain, B29, Fc RIII, Fc RI, and combinations of signaling molecules, such as CD3ζ and CD28, CD27, 4-1BB, DAP-10, OX40, and combinations thereof, as well as other similar molecules and fragments. Intracellular signaling portions of other members of the families of activating proteins can be used, such as FcγRIII and FcεRI. Examples of these alternative transmembrane and intracellular domains can be found, e.g., Gross et al., 1992; Stancovski et al., 1993; Moritz et al., 1994; Hwu et al., 1995; Weijtens et al., 1996; and Hekele et al., 1996, which are incorporated herein by reference in their entirety. In some embodiments, an endodomain may comprise the human CD3ζ intracellular domain.

The antigen-specific extracellular domain and the intracellular signaling-domain are preferably linked by a transmembrane domain. Transmembrane domains that may be included in a CAR include, e.g., the human IgG4 Fc hinge and Fc regions, the human CD4 transmembrane domain, the human CD28 transmembrane domain, the transmembrane human CD3ζ domain, or a cysteine mutated human CD3ζ domain, or a transmembrane domain from a human transmembrane signaling protein such as, e.g., the CD16 and CD8 and erythropoietin receptor. Examples of transmembrane domains are provided, e.g., in Table 1.

In some embodiments, the endodomain comprises a sequence encoding a costimulatory receptors, such as e.g., a modified CD28 intracellular signaling domain, or a CD28, CD27, OX-40 (CD134), DAP10, or 4-1BB (CD137) costimulatory receptor. In some embodiments, both a primary signal initiated by CD3ζ, an additional signal provided by a human costimulatory receptor may be included in a CAR to more effectively activate a transformed T cells, which may help improve in vivo persistence and the therapeutic success of the adoptive immunotherapy. As noted in Table 1, the endodomain or intracellular receptor signaling domain may comprise the zeta chain of CD3 alone or in combination with an Fcγ RIII costimulatory signaling domains such as, e.g., CD28, CD27, DAP10, CD137, OX40, CD2, 4-1BB. In some embodiments, the endodomain comprises part or all of one or more of TCR zeta chain, CD28, CD27, OX40/CD134, 4-1BB/CD137, FcεRIγ, ICOS/CD278, IL-2Rbeta/CD122, IL-2Ralpha/CD132, DAP10, DAP12, and CD40. In some embodiments, 1, 2, 3, 4 or more cytoplasmic domains may be included in an endodomain. For example, in some CARs it has been observed that at least two or three signaling domains fused together can result in an additive or synergistic effect.

In some aspects, an isolated nucleic acid segment and expression cassette including DNA sequences that encode a CAR may be generated. A variety of vectors may be used. In some preferred embodiments, the vector may allow for delivery of the DNA encoding a CAR to immune such as T cells. CAR expression may be under the control of regulated eukaryotic promoter such as, e.g., the MNDU3 promoter, CMV promoter, EF1alpha promoter, or Ubiquitin promoter. Also, the vector may contain a selectable marker, if for no other reason, to facilitate their manipulation in vitro. In some embodiments, the CAR can be expressed from mRNA in vitro transcribed from a DNA template.

Chimeric antigen receptor molecules are recombinant and are distinguished by their ability to both bind antigen and transduce activation signals via immunoreceptor activation motifs (ITAM's) present in their cytoplasmic tails. Receptor constructs utilizing an antigen-binding moiety (for example, generated from single chain antibodies (scFv)) afford the additional advantage of being "universal" in that they can bind native antigen on the target cell surface in an HLA-independent fashion. For example, a scFv constructs may be fused to sequences coding for the intracellular portion of the CD3 complex's zeta chain (ζ), the Fc receptor gamma chain, and sky tyrosine kinase (Eshhar et al., 1993; Fitzer-Attas et al., 1998). Re-directed T cell effector mechanisms including tumor recognition and lysis by CTL have been documented in several murine and human antigen-scFv: ζ systems (Eshhar et al., 1997; Altenschmidt et al., 1997; Brocker et al., 1998).

In some embodiments, a TCR is included in a CAR as the antigen binding domain (e.g., as a scFv region) and the CAR further comprises a hinge region, a transmembrane region, and an endodomain. For example, the TCR (e.g., an alpha chain comprising SEQ ID NO: 1 or 3, and a beta chain comprising SEQ ID NO:2 or 4) may be included in a CAR with a hinge region, a transmembrane region, and an endodomain as described in Table 1 below.

TABLE 1

Regions that may be included in an anti-TCL1 targeting CAR

Hinge/Scaffold

12 AA (peptide) (e.g., SEQ ID NO: 34)
t-20 AA (peptide) (e.g., SEQ ID NO: 35)
CD8 α (e.g., SEQ ID NO: 36)
IgG4 Fc (e.g., SEQ ID NO: 37)
2D3 (e.g., SEQ ID NO: 38)
IgG4 Fc Δ EQ (IgG4Fc N40Q) (e.g., SEQ ID NO: 39)
IgG4 Fc Δ Q (IgG4Fc L18E N40Q) (e.g. SEQ ID NO: 40)
t-12AA + t-20AA
mKate (e.g., SEQ ID NO: 41)
phiLov (e.g., SEQ ID NO: 42)
dsRed (e.g., SEQ ID NO: 43)
Venus (e.g., SEQ ID NO: 44)
eGFP (e.g., SEQ ID NO: 45)
CH3 HA (e.g., SEQ ID NO: 46)
mTFP-1 (e.g., SEQ ID NO: 47)
CD8 α + t-20AA
Double t-20 AA
t-20AA + CD8α
CD8α + Leucine Zipper Basep1 (e.g., SEQ ID NO: 48)
CD8α + Leucine Zipper Acid1 (e.g., SEQ ID NO: 49)

Transmembrane domain

CD28 (e.g., SEQ ID NO: 50)
CD137 (4-1BB) (e.g., SEQ ID NO: 51)
CD8α (e.g., SEQ ID NO: 52)
CD3ζ (e.g., SEQ ID NO: 53)

Endo-domain (signaling domain)

CD28 + CD3ζ
CD28 + CD27 + CD3ζ
CD28 + OX40 + CD3ζ
CD28 + 4-1BB + CD3ζ
CD28 + CD27 + OX40 + CD3ζ
CD28 + 4-1BB + CD27 + CD3ζ
CD28 + 4-1BB + OX40 + CD3ζ
4-1BB + CD3ζ
4-1BB + OX40 + CD3ζ
4-1BB + CD27 + CD3ζ
CD27 + CD3ζ
CD27 + OX 40 + CD3ζ
CD28Δ + CD3ζ
CD28Δ + CD27 + CD3ζ
CD28Δ + OX40 + CD3ζ
CD28Δ + 4-1BB + CD3ζ
CD28Δ + 4-1BB + OX40 + CD3ζ
CD28Δ + CD27 + OX40 + CD3ζ
CD28Δ + 4-1BB + CD27 + CD3ζ
4-1BB + ICOS + CD3ζ
CD28 + ICOS + CD3ζ
ICOS + CD3ζ
CD3ζ
CD28 only ζ-zeta; Δ-mutant; Note = 4-1BB is also referred to as CD137; "+" refers to the fusion of the different regions.

II. Soluble TCRs

In some embodiments, the present disclosure provides soluble TCRs, such as a TCL1-TCR provided herein. Soluble TCRs are useful, not only for the purpose of investigating specific TCR-pMHC interactions, but also potentially as a diagnostic tool to detect infection, or to detect autoimmune disease markers. Soluble TCRs also have applications in staining, for example to stain cells for the presence of a particular peptide antigen presented in the context of the MHC. Similarly, soluble TCRs can be used to deliver a therapeutic agent, for example a cytotoxic compound or an immunostimulating compound, to cells presenting a particular antigen. Soluble TCRs may also be used to inhibit T cells, for example, those reacting to an auto-immune peptide antigen.

In the context of this application, "solubility" is defined as the ability of the TCR to be purified as a mono disperse heterodimer in phosphate buffered saline (PBS) (KCL 2.7 mM, KH$_2$PO$_4$ 1.5 mM, NaCl 137 mM and Na$_2$PO4 8 mM, pH 7.1-7.5. Life Technologies, Gibco BRL) at a concentration of 1 mg/ml and for more than 90% of said TCR to remain as a mono disperse heterodimer after incubation at 25° C. for 1 hour.

In some aspects, the present disclosure provides a soluble T cell receptor (sTCR), which comprises (i) all or part of a TCR α chain (e.g., SEQ ID NO:1 or 3), except the transmembrane domain thereof, and (ii) all or part of a TCR β chain (e.g., SEQ ID NO:2 or 4), except the transmembrane domain thereof, wherein (i) and (ii) each comprise a functional variable domain and at least a part of the constant domain of the TCR chain, and are linked by a disulfide bond between constant domain residues which is not present in native TCR.

In some aspects, the soluble TCR comprises a TCR α or γ chain extracellular domain dimerized to a TCR β or δ chain extracellular domain respectively, by means of a pair of C-terminal dimerization peptides, such as leucine zippers (International Patent Publication No. WO 99/60120; U.S. Pat. No. 7,666,604).

A soluble TCR, which may be human or produced in human cells, of the present disclosure may be provided in substantially pure form, or as a purified or isolated preparation. For example, it may be provided in a form which is substantially free of other proteins.

A plurality of soluble TCRs of the present disclosure may be provided in a multivalent complex. Thus, the present disclosure provides, in one aspect, a multivalent T cell receptor (TCR) complex, which comprises a plurality of soluble T cell receptors as described herein. Each of the plurality of soluble TCRs is preferably identical.

A multivalent TCR complex generally comprises a multimer of two or three or four or more T cell receptor molecules associated (e.g. covalently or otherwise linked) with one another, preferably via a linker molecule. Suitable linker molecules include, but are not limited to, multivalent attachment molecules such as avidin, streptavidin, neutravidin and extravidin, each of which has four binding sites for biotin. Thus, biotinylated TCR molecules can be formed into multimers of T cell receptors having a plurality of TCR binding sites. The number of TCR molecules in the multimer will depend upon the quantity of TCR in relation to the quantity of linker molecule used to make the multimers, and also on the presence or absence of any other biotinylated molecules. Preferred multimers are dimeric, trimeric or tetrameric TCR complexes.

Suitable structures for use in the present methods include membrane structures such as liposomes and solid structures which are preferably particles such as beads, for example latex beads. Other structures which may be externally coated with T cell receptor molecules are also suitable. Preferably, the structures are coated with T cell receptor multimers rather than with individual T cell receptor molecules.

In the case of liposomes, the T cell receptor molecules or multimers thereof may be attached to or otherwise associated with the membrane. Techniques for this are well known to those skilled in the art.

A label or another moiety, such as a toxic or therapeutic moiety, may be included in a multivalent TCR complex of the present invention. For example, the label or other moiety may be included in a mixed molecule multimer. An example of such a multimeric molecule is a tetramer containing three TCR molecules and one peroxidase molecule. This may be achieved by mixing the TCR and the enzyme at a molar ratio of about 3:1 to generate tetrameric complexes, and isolating the desired complex from any complexes not containing the correct ratio of molecules. These mixed molecules may contain any combination of molecules, provided that steric hindrance does not compromise or does not significantly compromise the desired function of the molecules. The positioning of the binding sites on the streptavidin molecule is suitable for mixed tetramers since steric hindrance is not likely to occur.

The TCR (or multivalent complex thereof) of the present disclosure may alternatively or additionally be associated with (e.g. covalently or otherwise linked to) a therapeutic agent which may be, for example, a toxic moiety for use in cell killing, or an immunostimulating agent such as an interleukin or a cytokine. A multivalent TCR complex of the present invention may have enhanced binding capability for a TCR ligand compared to a non-multimeric T cell receptor heterodimer. Thus, the multivalent TCR complexes may be used in some embodiments for tracking or targeting cells presenting particular antigens in vitro or in vivo, and are also useful as intermediates for the production of further multivalent TCR complexes having such uses. The TCR or multivalent TCR complex may therefore be provided in a pharmaceutically acceptable formulation for use in vivo.

The present disclosure also provides a method for delivering a therapeutic agent to a target cell, which method comprises contacting potential target cells with a TCR or multivalent TCR complex under conditions to allow attachment of the TCR or multivalent TCR complex to the target cell, said TCR or multivalent TCR complex being specific for the TCR ligand and having the therapeutic agent associated therewith.

In some embodiments, the soluble TCR or multivalent TCR complex can be used to deliver therapeutic agents to the location of cells presenting a particular antigen. This can be useful, e.g., for the treatment of tumors. A therapeutic agent could be delivered such that it would exercise its effect locally and not only on the cell it binds (e.g., a chemotherapeutic, radioactive, or enzymatic agent may result in a local effect near or on a tumor). Thus, one particular strategy envisages anti-tumor molecules linked to T cell receptors or multivalent TCR complexes specific for tumor antigens.

Many therapeutic agents can be employed for this use, for instance radioactive compounds, enzymes (e.g., perforin) or chemotherapeutic agents (e.g., cisplatin). To improve limiting toxic effects in the desired location the toxin may be provided inside a liposome linked to streptavidin so that the compound is released slowly. This may reduce damaging effects during the transport in the body and help to limit toxic effects until after binding of the TCR to the relevant antigen presenting cells.

Other suitable therapeutic agents include:
small molecule cytotoxic agents, i.e. compounds with the ability to kill mammalian cells having a molecular weight of less than 700 daltons. Such compounds could also contain toxic metals capable of having a cytotoxic effect. Furthermore, it is to be understood that these small molecule cytotoxic agents also include pro-drugs, i.e. compounds that decay or are converted under physiological conditions to release cytotoxic agents. Examples of such agents include cis-platin, maytansine derivatives, rachelmycin, calicheamicin, docetaxel, etoposide, gemcitabine, ifosfamide, irinotecan, melphalan, mitoxantrone, sorfimer sodiumphotofrin II, temozolmide, topotecan, trimetreate glucuronate, auristatin E vincristine and doxorubicin;

peptide cytotoxins, i.e. proteins or fragments thereof with the ability to kill mammalian cells. Examples include ricin, diphtheria toxin, *Pseudomonas* bacterial exotoxin A, DNAase and RNAase;

radio-nuclides, i.e. unstable isotopes of elements which decay with the concurrent emission of one or more of α or β particles, or γ rays. Examples include iodine 131, rhenium 186, indium 111, yttrium 90, bismuth 210 and 213, actinium 225 and astatine 213;

prodrugs, such as antibody directed enzyme pro-drugs; and immuno-stimulants, i.e. moieties which stimulate immune response. Examples include cytokines such as IL-2, chemokines such as IL-8, platelet factor 4, melanoma growth stimulatory protein, etc., antibodies or fragments thereof such as anti-CD3 antibodies or fragments thereof, complement activators, xenogeneic protein domains, allogeneic protein domains, viral/bacterial protein domains and viral/bacterial peptides.

The soluble TCRs of the present disclosure may be used to modulate T cell activation by binding to specific TCR ligand and thereby inhibiting T cell activation. Autoimmune diseases involving T cell-mediated inflammation and/or tissue damage would be amenable to this approach, for example type I diabetes. Knowledge of the specific peptide epitope presented by the relevant pMHC is required for this use.

The use of the soluble TCRs and/or multivalent TCR complexes of the present disclosure in the preparation of a composition for the treatment of cancer or autoimmune disease is also envisaged.

Also provided is a method of treatment of cancer (e.g., a leukemia, lymphoma, or B-cell malignancy, or other cancer that expresses TCL1 as described herein) or autoimmune disease comprising administration to a patient in need thereof of an effective amount of the soluble TCRs and/or multivalent TCR complexes of the present invention.

As is common in anti-cancer and autoimmune therapy the TCRs of the present disclosure may be used in combination with other agents for the treatment of cancer and autoimmune disease, and one or more additional therapeutic or therapy may be administered to treat other related condition(s) found in the patient groups.

III. Adoptive Cell Transfer Therapies

Provided herein are methods for treating or delaying progression of cancer in an individual comprising administering to the individual an effective amount an antigen-specific cell (e.g., autologous or allogeneic T cells (e.g., regulatory T cells, CD4+ T cells, CD8+ T cells, or gamma-delta T cells), NK cells, invariant NK cells, NKT cells, mesenchymal stem cell (MSC)s, or induced pluripotent stem (iPS) cells) therapy, such as a TCL1-specific cell therapy. Adoptive T cell therapies with genetically engineered TCR-transduced T cells (e.g., expressing a TCR comprising one or more of SEQ ID NOs:1-4, such as SEQ ID NOs: 1 and 3, or SEQ ID NOs: 2 and 4) are also provided herein. In further embodiments, methods are provided for the treatment of cancer (e.g., melanoma) comprising immunizing a subject with a purified tumor antigen or an immunodominant tumor antigen-specific peptide. In some embodiments, the adoptive cell transfer therapy is provided to a subject (e.g., a human patient) in combination with as second therapy, such as a chemotherapy, a radiotherapy, a surgery, or a second immunotherapy.

Embodiments of the present disclosure concern obtaining and administering TCR-engineered cells to a subject as an immunotherapy to target cancer cells. In particular, the TCR-engineered (e.g., autologous or allogeneic T cells (e.g., regulatory T cells, CD4+ T cells, CD8+ T cells, or gamma-delta T cells), NK cells, invariant NK cells, NKT cells, mesenchymal stem cell (MSC)s, or induced pluripotent stem (iPS) cells) cells are antigen-specific cells (e.g., TCL1-specific cells). Several basic approaches for the derivation, activation and expansion of functional anti-tumor effector cells have been described in the last two decades. These include: autologous cells, such as tumor-infiltrating lymphocytes (TILs); T cells activated ex-vivo using autologous DCs, lymphocytes, artificial antigen-presenting cells (APCs) or beads coated with T cell ligands and activating antibodies, or cells isolated by virtue of capturing target cell membrane; allogeneic cells naturally expressing anti-host tumor T cell receptor (TCR); and non-tumor-specific autologous or allogeneic cells genetically reprogrammed or "redirected" to express tumor-reactive TCR or chimeric TCR molecules displaying antibody-like tumor recognition capacity known as "T-bodies". These approaches have given rise to numerous protocols for T cell preparation and immunization which can be used in the methods described herein.

A. T Cell Preparation and Administration

In some embodiments, T cells are autologous. However, the cells can be allogeneic. In some embodiments, the T cells are isolated from the patient, so that the cells are autologous. If the T cells are allogeneic, the T cells can be pooled from several donors. The cells are administered to the subject of interest in an amount sufficient to control, reduce, or eliminate symptoms and signs of the disease being treated.

In some embodiments, the T cells are derived from the blood, bone marrow, lymph, umbilical cord, or lymphoid organs. In some aspects, the cells are human cells. The cells typically are primary cells, such as those isolated directly from a subject and/or isolated from a subject and frozen. In some embodiments, the cells include one or more subsets of T cells or other cell types, such as whole T cell populations, CD4$^+$ cells, CD8$^+$ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. In some aspects, such as for off-the-shelf technologies, the cells are pluripotent and/or multipotent, such as stem cells, such as induced pluripotent stem cells (iPSCs); for example, the stem cells or iPSC may be differentiated into various T cell populations. In some embodiments, the methods include isolating cells from the subject, preparing, processing, culturing, and/or engineering them, as described herein, and re-introducing them into the same patient, before or after cryopreservation.

Among the sub-types and subpopulations of T cells (e.g., CD4$^+$ and/or CD8$^+$ T cells) are naive T (T$_N$) cells, effector T cells (T$_{EFF}$), memory T cells and sub-types thereof, such as stem cell memory T (TSC$_M$), central memory T (TC$_M$), effector memory T (T$_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, one or more of the T cell populations is enriched for or depleted of cells that are positive for a specific marker, such as surface markers, or that are negative for a specific marker. In some cases, such markers are those that are absent or expressed at relatively low levels on certain populations of T cells (e.g., non-memory cells) but are present or expressed at relatively higher levels on certain other populations of T cells (e.g., memory cells).

In some embodiments, T cells are separated from a PBMC sample by negative selection of markers expressed on non-T cells, such as B cells, monocytes, or other white blood cells, such as CD14. In some aspects, a CD4$^+$ or CD8$^+$ selection step is used to separate CD4$^+$ helper and CD8$^+$ cytotoxic T cells. Such CD4$^+$ and CD8$^+$ populations can be further sorted into sub-populations by positive or negative selection for markers expressed or expressed to a relatively higher degree on one or more naive, memory, and/or effector T cell subpopulations. A variety of methods may be used for separation of cells based on expression of markers, including magnetic activated cell sorting (MACS) and fluorescence activated cell sorting (FACS).

In some embodiments, CD8$^+$ T cells are further enriched for or depleted of naive, central memory, effector memory, and/or central memory stem cells, such as by positive or negative selection based on surface antigens associated with the respective subpopulation. In some embodiments, enrichment for central memory T ($T_{CM}$) cells is carried out to increase efficacy, such as to improve long-term survival, expansion, and/or engraftment following administration, which in some aspects is particularly robust in such sub-populations (e.g., see Terakura et al., 2012; Wang et al., 2012.

In some embodiments, the T cells are autologous T cells. In this method, tumor samples are obtained from patients and a single cell suspension is obtained. The single cell suspension can be obtained in any suitable manner, e.g., mechanically (disaggregating the tumor using, e.g., a gentleMACS™ Dissociator, Miltenyi Biotec, Auburn, Calif.) or enzymatically (e.g., collagenase or DNase). Single-cell suspensions of tumor enzymatic digests are cultured in interleukin-2 (IL-2). The cells are cultured until confluence (e.g., about 2×10$^6$ lymphocytes), e.g., from about 5 to about 21 days, preferably from about 10 to about 14 days. For example, the cells may be cultured from 5 days, 5.5 days, or 5.8 days to 21 days, 21.5 days, or 21.8 days, such as from 10 days, 10.5 days, or 10.8 days to 14 days, 14.5 days, or 14.8 days.

The cultured T cells can be pooled and rapidly expanded. Rapid expansion provides an increase in the number of antigen-specific T cells of at least about 50-fold (e.g., 50-, 60-, 70-, 80-, 90-, or 100-fold, or greater) over a period of about 10 to about 14 days. More preferably, rapid expansion provides an increase of at least about 200-fold (e.g., 200-, 300-, 400-, 500-, 600-, 700-, 800-, 900-, or greater) over a period of about 10 to about 14 days.

Expansion can be accomplished by any of a number of methods as are known in the art. For example, T cells can be rapidly expanded using non-specific T cell receptor stimulation in the presence of feeder lymphocytes and either interleukin-2 (IL-2) or interleukin-15 (IL-15), with IL-2 being preferred. The non-specific T cell receptor stimulus can include around 30 ng/ml of OKT3, a mouse monoclonal anti-CD3 antibody (available from Ortho-McNeil®, Raritan, N.J.). Alternatively, T cells can be rapidly expanded by stimulation of peripheral blood mononuclear cells (PBMC) in vitro with one or more antigens (including antigenic portions thereof, such as epitope(s), or a cell) of the cancer, which can be optionally expressed from a vector, such as an human leukocyte antigen A2 (HLA-A2) binding peptide, in the presence of a T cell growth factor, such as 300 IU/ml IL-2 or IL-15, with IL-2 being preferred. The in vitro-induced T cells are rapidly expanded by re-stimulation with the same antigen(s) of the cancer pulsed onto HLA-A2-expressing antigen-presenting cells. Alternatively, the T cells can be re-stimulated with irradiated, autologous lymphocytes or with irradiated HLA-A2+ allogeneic lymphocytes and IL-2, for example.

The autologous T cells can be modified to express a T cell growth factor that promotes the growth and activation of the autologous T cells. Suitable T cell growth factors include, for example, interleukin (IL)-2, IL-7, IL-15, and IL-12. Suitable methods of modification are known in the art including, e.g., Sambrook et al., 2001; and Ausubel et al., 1994. In some embodiments, modified autologous T cells express the T cell growth factor at high levels. T cell growth factor coding sequences, such as that of IL-12, are readily available in the art, as are promoters, the operable linkage of which to a T cell growth factor coding sequence promote high-level expression.

In certain embodiments, a T cell growth factor that promotes the growth and activation of the autologous T cells is administered to the subject either concomitantly with the autologous T cells or subsequently to the autologous T cells. The T cell growth factor can be any suitable growth factor that promotes the growth and activation of the autologous T cells. Examples of suitable T cell growth factors include interleukin (IL)-2, IL-7, IL-15, and IL-12, which can be used alone or in various combinations, such as IL-2 and IL-7, IL-2 and IL-15, IL-7 and IL-15, IL-2, IL-7 and IL-15, IL-12 and IL-7, IL-12 and IL-15, or IL-12 and IL2. IL-12 is a preferred T cell growth factor.

The T cell may be administered intravenously, intramuscularly, subcutaneously, transdermally, intraperitoneally, intrathecally, parenterally, intrathecally, intracavitary, intraventricularly, intra-arterially, or via the cerebrospinal fluid, or by any implantable or semi-implantable, permanent or degradable device. The appropriate dosage of the T cell therapy may be determined based on the type of disease to be treated, severity and course of the disease, the clinical condition of the individual, the individual's clinical history and response to the treatment, and the discretion of the attending physician.

Intratumoral injection, or injection into the tumor vasculature is specifically contemplated for discrete, solid, accessible tumors. Local, regional or systemic administration also may be appropriate. For tumors of >4 cm, the volume to be administered will be about 4-10 ml (in particular 10 ml), while for tumors of <4 cm, a volume of about 1-3 ml will be used (e.g., 3 ml). Multiple injections delivered as single dose may comprise about 0.1 to about 0.5 ml volumes.

In some embodiments, naked DNA or a suitable vector encoding a CAR can be introduced into a subject's T cells (e.g., T cells obtained from a human patient with cancer or other disease). Methods of stably transfecting T cells by electroporation using naked DNA are known in the art. See, e.g., U.S. Pat. No. 6,410,319. Naked DNA generally refers to the DNA encoding a chimeric receptor of the present invention contained in a plasmid expression vector in proper orientation for expression. In some embodiments, the use of naked DNA may reduce the time required to produce T cells expressing a CAR generated via methods of the present invention.

Alternatively, a viral vector (e.g., a retroviral vector, adenoviral vector, adeno-associated viral vector, or lentiviral vector) can be used to introduce the TCR or chimeric construct into T cells. Generally, a vector encoding a TCR or CAR that is used for transfecting a T cell from a subject should generally be non-replicating in the subject's T cells. A large number of vectors are known that are based on viruses, where the copy number of the virus maintained in the cell is low enough to maintain viability of the cell. Illustrative vectors include the pFB-neo vectors (STRATA-GENE®) as well as vectors based on HIV, SV40, EBV, HSV, or BPV.

Once it is established that the transfected or transduced T cell is capable of expressing a TCR or CAR as a surface membrane protein with the desired regulation and at a desired level, it can be determined whether the TCR or chimeric receptor is functional in the host cell to provide for the desired signal induction. Subsequently, the transduced T cells may be reintroduced or administered to the subject to activate anti-tumor responses in the subject. To facilitate administration, the transduced T cells may be made into a pharmaceutical composition or made into an implant appropriate for administration in vivo, with appropriate carriers or diluents, which are preferably pharmaceutically acceptable. The means of making such a composition or an implant have been described in the art (see, for instance, Remington's Pharmaceutical Sciences, 16th Ed., Mack, ed., 1980). Where appropriate, transduced T cells expressing a TCR or CAR can be formulated into a preparation in semisolid or liquid form, such as a capsule, solution, injection, inhalant, or aerosol, in the usual ways for their respective route of administration. Means known in the art can be utilized to prevent or minimize release and absorption of the composition until it reaches the target tissue or organ, or to ensure timed-release of the composition. Generally, a pharmaceutically acceptable form is preferably employed that does not significantly adversely affect the cells expressing the TCR or chimeric receptor. In some embodiments, the transduced T cells can be made into a pharmaceutical composition containing a balanced salt solution such as Hanks' balanced salt solution, or normal saline.

B. Antigen-Presenting Cells

Antigen-presenting cells, which include macrophages, B lymphocytes, and dendritic cells, are distinguished by their expression of a particular MHC molecule. APCs internalize antigen and re-express a part of that antigen, together with the MHC molecule on their outer cell membrane. The major histocompatibility complex (MHC) is a large genetic complex with multiple loci. The MHC loci encode two major classes of MHC membrane molecules, referred to as class I and class II MHCs. T helper lymphocytes generally recognize antigen associated with MHC class II molecules, and T cytotoxic lymphocytes recognize antigen associated with MHC class I molecules. In humans the MHC is referred to as the HLA complex and in mice the H-2 complex.

In some cases, artificial antigen presenting cells (aAPCs) are useful in preparing TCR or CAR-based therapeutic compositions and cell therapy products. For general guidance regarding the preparation and use of antigen-presenting systems, see, e.g., U.S. Pat. Nos. 6,225,042, 6,355,479, 6,362,001 and 6,790,662; U.S. Patent Application Publication Nos. 2009/0017000 and 2009/0004142; and International Publication No. WO2007/103009).

aAPCs may be used to expand T Cells expressing a TCR or CAR. During encounter with tumor antigen, the signals delivered to T cells by antigen-presenting cells can affect T cell programming and their subsequent therapeutic efficacy. This has stimulated efforts to develop artificial antigen-presenting cells that allow optimal control over the signals provided to T cells (Turtle et al., 2010). In addition to antibody or antigen of interest, the aAPC systems may also comprise at least one exogenous assisting molecule. Any suitable number and combination of assisting molecules may be employed. The assisting molecule may be selected from assisting molecules such as co-stimulatory molecules and adhesion molecules. Exemplary co-stimulatory molecules include CD70 and B7.1 (also called B7 or CD80), which can bind to CD28 and/or CTLA-4 molecules on the surface of T cells, thereby affecting, e.g., T cell expansion, Th1 differentiation, short-term T cell survival, and cytokine secretion such as interleukin (IL)-2 (see Kim et al., 2004). Adhesion molecules may include carbohydrate-binding glycoproteins such as selectins, transmembrane binding glycoproteins such as integrins, calcium-dependent proteins such as cadherins, and single-pass transmembrane immunoglobulin (Ig) superfamily proteins, such as intercellular adhesion molecules (ICAMs) that promote, for example, cell-to-cell or cell-to-matrix contact. Exemplary adhesion molecules include LFA-3 and ICAMs, such as ICAM-1. Techniques, methods, and reagents useful for selection, cloning, preparation, and expression of exemplary assisting molecules, including co-stimulatory molecules and adhesion molecules, are exemplified in, e.g., U.S. Pat. Nos. 6,225,042, 6,355,479, and 6,362,001.

C. Nucleic Acids

In an aspect, the present disclosure provides a nucleic acid encoding an isolated TCR, CAR, or soluble peptide that selectively binds TCL1 (e.g., at the $TCL1_{70-79}$ immunogenic epitopes) and has at least about 90%, 91%, 92%, 93%, 94%, 95%, 96%, 97%, 98%, 99%, or 100% sequence identity to a TCR variable region disclosed herein (e.g., SEQ ID NO:1-4), or the peptide may have 1, 2, 3, or 4 point mutations (e.g., substitution mutations) as compared to SEQ ID NO:1-4. As stated above, peptide may be, e.g., from 8 to 35 amino acids in length, or any range derivable therein. In some embodiments, the tumor antigen-specific peptide corresponds to a portion of the tumor antigen protein such as $TCL1_{70-79}$ of TCL1. The term "nucleic acid" is intended to include DNA and RNA and can be either double stranded or single stranded.

Accordingly, a nucleic acid encoding a TCR, CAR, or soluble peptide that selectively binds TCL1 may be operably linked to an expression vector and the peptide produced in the appropriate expression system using methods well known in the molecular biological arts. A nucleic acid encoding a tumor antigen-specific peptide disclosed herein may be incorporated into any expression vector which ensures good expression of the peptide. Possible expression vectors include but are not limited to cosmids, plasmids, or modified viruses (e.g. replication defective retroviruses, adenoviruses and adeno-associated viruses), so long as the vector is suitable for transformation of a host cell.

A recombinant expression vector being "suitable for transformation of a host cell" means that the expression vector contains a nucleic acid molecule of the invention and regulatory sequences selected on the basis of the host cells to be used for expression, which is operatively linked to the nucleic acid molecule. The terms, "operatively linked" or "operably linked" are used interchangeably, and are intended to mean that the nucleic acid is linked to regulatory sequences in a manner which allows expression of the nucleic acid.

Accordingly, the present invention provides a recombinant expression vector comprising nucleic acid encoding a TCR, CAR, or soluble peptide that selectively binds TCL1, and the necessary regulatory sequences for the transcription and translation of the inserted protein-sequence. Suitable regulatory sequences may be derived from a variety of sources, including bacterial, fungal, or viral genes (e.g., see the regulatory sequences described in Goeddel, 1990).

Selection of appropriate regulatory sequences is generally dependent on the host cell chosen, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native protein and/or its flanking regions.

A recombinant expression vector may also contain a selectable marker gene which facilitates the selection of host cells transformed or transfected with the TCR, CAR, or soluble peptide that selectively binds TCL1 disclosed herein. Examples of selectable marker genes are genes encoding a protein such as G418 and hygromycin which confer resistance to certain drugs, β-galactosidase, chloramphenicol acetyltransferase, or firefly luciferase. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of a recombinant expression vector, and in particular, to determine the effect of a mutation on expression and phenotype. It will be appreciated that selectable markers can be introduced on a separate vector from the nucleic acid of interest Recombinant expression vectors can be introduced into host cells to produce a transformant host cell. The term "transformant host cell" is intended to include prokaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Suitable host cells include a wide variety of prokaryotic and eukaryotic host cells. For example, the proteins of the invention may be expressed in bacterial cells such as *E. coli*, insect cells (using baculovirus), yeast cells or mammalian cells.

A nucleic acid molecule of the invention may also be chemically synthesized using standard techniques. Various methods of chemically synthesizing polydeoxy-nucleotides are known, including solid-phase synthesis which, like peptide synthesis, has been fully automated in commercially available DNA synthesizers (See e.g., U.S. Pat. Nos. 4,598,049; 4,458,066; 4,401,796; and 4,373,071).

II. PHARMACEUTICAL PREPARATIONS

In select embodiments, it is contemplated that a cell expressing a TCR as disclosed herein, a protein containing the variable regions of a TCR, or a DNA encoding the variable regions of a TCR of the present invention may be comprised in a vaccine composition and administered to a subject to induce a therapeutic immune response in the subject towards a cancer, such as a B-cell malignancy or a solid tumor that expresses TCL1. A therapeutic composition for pharmaceutical use in a subject may comprise a TCR composition disclosed herein, such as a soluble TCR (optionally attached to an imaging agent), and a pharmaceutically acceptable carrier.

The phrases "pharmaceutical," "pharmaceutically acceptable," or "pharmacologically acceptable" refers to molecular entities and compositions that do not produce an adverse, allergic or other untoward reaction when administered to an animal, such as, for example, a human, as appropriate. As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington: The Science and Practice of Pharmacy, 21st edition, Pharmaceutical Press, 2011, incorporated herein by reference). Except insofar as any conventional carrier is incompatible with the active ingredient, its use in the vaccine compositions of the present invention is contemplated.

As used herein, a "protective immune response" refers to a response by the immune system of a mammalian host to a cancer. A protective immune response may provide a therapeutic effect for the treatment of a cancer, e.g., decreasing tumor size, increasing survival, etc.

A person having ordinary skill in the medical arts will appreciate that the actual dosage amount of a therapeutic composition administered to an animal or human patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

A therapeutic composition disclosed herein can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctivally, intravesicularlly, mucosally, intrapericardially, intraumbilically, intraocularly, orally, topically, locally, and by inhalation, injection, infusion, continuous infusion, lavage, and localized perfusion. A therapeutic composition may also be administered to a subject via a catheter, in cremes, in lipid compositions, by ballistic particulate delivery, or by other method or any combination of the forgoing as would be known to one of ordinary skill in the art (see, for example, Remington: The Science and Practice of Pharmacy, 21$^{st}$ Ed. Lippincott Williams and Wilkins, 2005, incorporated herein by reference).

While any suitable carrier known to those of ordinary skill in the art may be employed in the pharmaceutical compositions of this invention, the type of carrier will vary depending on the mode of administration. For parenteral administration, such as intravenous, intratumoral or subcutaneous injection, the carrier may comprise water, saline, alcohol, a fat, a wax or a buffer. Biodegradable microspheres (e.g., polylactic galactide) may also be employed as carriers in some embodiments. Suitable biodegradable microspheres are disclosed, for example, in U.S. Pat. Nos. 4,897,268 and 5,075,109.

In some embodiments, the vaccine composition may be administered by microstructured transdermal or ballistic particulate delivery. Microstructures as carriers for vaccine formulation are a desirable configuration for vaccine applications and are widely known in the art (e.g., U.S. Pat. Nos. 5,797,898, 5,770,219 and 5,783,208, and U.S. Patent Application 2005/0065463). Microstructures or ballistic particles that serve as a support substrate for an TCR, such as a soluble TCR, disclosed herein may be comprised of biodegradable material and non-biodegradable material, and such support substrates may be comprised of synthetic polymers, silica, lipids, carbohydrates, proteins, lectins, ionic agents, crosslinkers, and other microstructure components available in the art. Protocols and reagents for the immobilization of a peptide of the invention to a support substrate composed of such materials are widely available commercially and in the art.

In other embodiments, a vaccine composition comprises an immobilized or encapsulated TCR or soluble TCR disclosed herein and a support substrate. In these embodiments, a support substrate can include, but is not limited to, a lipid microsphere, a lipid nanoparticle, an ethosome, a liposome, a niosome, a phospholipid, a sphingosome, a surfactant, a transferosome, an emulsion, or a combination thereof. The formation and use of liposomes and other lipid nano- and microcarrier formulations is generally known to those of ordinary skill in the art, and the use of liposomes, microparticles, nanocapsules and the like have gained widespread use in delivery of therapeutics (e.g., U.S. Pat. No. 5,741,516, specifically incorporated herein in its entirety by reference). Numerous methods of liposome and liposome-like preparations as potential drug carriers, including encapsulation of peptides are known and may be used in various embodiments (e.g., U.S. Pat. Nos. 5,567,434, 5,552,157, 5,565,213, 5,738,868, and 5,795,587).

A soluble TCR may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids such as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

A. Combination Therapies

In certain embodiments, the compositions and methods of the present embodiments involve an antigen-specific cell (e.g., autologous or allogeneic T cells (e.g., regulatory T cells, CD4+ T cells, CD8+ T cells, or gamma-delta T cells), NK cells, invariant NK cells, NKT cells, mesenchymal stem cell (MSC)s, or induced pluripotent stem (iPS) cells) population in combination with at least one additional therapy. The additional therapy may be radiation therapy, surgery (e.g., lumpectomy and a mastectomy), chemotherapy, a conditioning chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy.

In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is a chemotherapy such as, e.g., dacarbazine, or temozolomide. The additional therapy may be one or more of the chemotherapeutic agents known in the art.

A T cell therapy may be administered before, during, after, or in various combinations relative to an additional cancer therapy, such as immune checkpoint therapy or conditioning chemotherapy. The administrations may be in intervals ranging from concurrently to minutes to days to weeks. In embodiments where the T cell therapy is provided to a patient separately from an additional therapeutic agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

Various combinations may be employed. For the example below an antigen-specific T cell therapy, peptide, or TCR is "A" and an anti-cancer therapy is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

III. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Patient Samples

The Institutional Review Board of The University of Texas M. D. Anderson Cancer Center approved the study. An informed consent was obtained in accordance with the Declaration of Helsinki prior to collection of patient samples. Peripheral blood mononuclear cells (PBMC) were isolated from blood samples by density gradient separation. Tissue samples were processed into single-cell suspension and cryopreserved in aliquots.

Cell Lines

MCL cell lines, Mino and Jeko-1; Burkitt's lymphoma cell line, Daudi; non-hematological tumor cell line, HCT-15, SW480, SW620, and T2 hybridoma cells were cultured in RPMI 1640 medium supplemented with 10% fetal bovine serum, 10 mM HEPES, 1× Glutamax, 50 µM β-mercaptoethanol, 1 mM sodium pyruvate, 100 U/mL penicillin+100 µg/mL streptomycin, and 10 µg/mL gentamicin (all from Invitrogen, Carlsbad, CA) at 37° C. and 5% $CO_2$ in air.

Tumor and Immune Cell Subset Isolation

Primary lymphoma cells, normal peripheral blood B and T cells were isolated by magnetic cell separation (MACS, Miltenyi Biotec, Auburn, CA) and the purity confirmed by flow cytometry as previously described (Weng et al., 2016a). The procedure yielded >90% purity of lymphoma cells, normal B and T cells.

Reagents

Mouse anti-human antibodies against CD3, CD4, CD8, CD20, IFN-γ and CD19 were obtained from BD Biosciences, San Jose, CA Enzyme-linked immunosorbent assay (ELISA) kits for IFN-γ were obtained from R&D Systems, Minneapolis, MN All peptides were synthesized by Sigma-Aldrich, St Louis, MO to greater than 70% purity and dissolved in dimethyl sulfoxide (Sigma-Aldrich). APC-conjugated tetramers were synthesized by MHC Tetramer Lab, Protein Chemistry Core of Baylor College of Medicine, Houston, TX APC-conjugated anti-TCL1 and isotype antibodies were obtained from Cell Signaling Technology, Beverly, MA Real-Time PCR Total RNA was extracted from purified solid tumor cell lines, or peripheral blood B and T cells using Trizol (Invitrogen). About 3 µg of total RNA from each source was reverse transcribed into cDNA with Superscript III kit (Invitrogen). Quantitative PCR was performed with Taqman real-time PCR kit (Applied Biosystems), and TCL1 (Applied Biosystems, Cat #Hs00951350_m1) and β-actin primers (Applied Biosystems, Cat #Hs99999903_m1) using the following conditions: 50° C. for 2 min, 94° C. for 10 min, followed by 94° C. for 15 sec, 60° C. for 60 sec for 40 cycles on Applied Biosystems StepOne™/StepOnePlus™ Real-Time PCR System. The expression of TCL1 mRNA relative to the β-actin mRNA was calculated in each sample.

Flow Cytometry

For intracellular staining, cells were fixed and permeabilized using BD Biosciences Cytofix/Cytoperm™ Plus Fixation/Permeabilization kit as per manufacturer's instructions. Cells were then stained with mouse anti-human-TCL1 antibody (eBioscience) or Alexa Fluor® 647 Mouse IgG2b isotype control antibody (eBiosciences) for 30 min at 4° C. After two washes, samples were acquired on a FACS Calibur (BD Biosciences) and analyzed using Cell Quest Pro (BD Biosciences) or FlowJo (Tree Star, Inc., Ashland, OR) software. Intracellular cytokine staining was performed as previously described (Weng et al., 2016b). For tetramer staining, APC-conjugated $TCL1_{71-78}$ tetramer or HIV $Gag_{77-85}$ tetramer and FITC-conjugated mouse anti-human CD8 antibody were mixed with the cells in 50 µl volume for 30 minutes at room temperature, washed twice, and analyzed by a flow cytometry.

Cloning by Limiting Dilution

TCL1-specific T cell lines were cultured at one cell/well in 96-well round bottom plate, supplied with 30 ng/ml anti-CD3, 180 IU/ml IL-2 and $1 \times 10^5$ feeder cells. The T clones were grown for 2 weeks and analyzed for antigen-specificity by IFN-γ ELISA. T cell clones that were tested positive were further expanded by rapid expansion protocol (REP).

Generation of TCL1-Specific TCR-T Cells by Lentivirus

Total RNA purified from T cell clone was analyzed by nano-string for TCR α and β subfamilies. The full TCRαβ sequences of TC1 T cell clone was obtained by RT-PCR and codon-optimized. The constant regions of α and β chains were cystein-mutated and the TCRαβ chains were ligated with P2A and cloned into a lentivirus producing vector. TCR-containing lentivirus were produced in 293T cells, filtered, concentrated and stored at −80° C. HLA A2+ normal donors' T cells were activated by OKT3 antibody for 72 hours and the transduction with lentivirus were carried out at 1000 g centrifuge at 32° C. for 2 hour followed by overnight incubation. The expression of antigen specific TCR was analyzed by TCR Vb specific antibody and tetramer 48 hour later. The tetramer positive T cells were sorted by flow and further expanded by REP for additional functional assays as previously described (Lee et al., 2008).

Cytotoxicity Assay

T2 cells were cultured overnight with 40 µg/ml peptide in the presence of 3 µg/ml β$_2$-microglobulin, washed twice, and used as targets in non-radioactive cytotoxicity assay (Promega). Primary tumor cells were isolated from PBMC or biopsy samples of lymphoma patients by MACS (Miltenyi). Primary lymphoma cells, lymphoma cell lines and non-hematological tumor cell line ($1 \times 10^4$ cells/well) were incubated with the effector T cells at the indicated ratios in 96-well round-bottom plates at 37° C. for 4-16 hours, and target cell lysis was determined by non-radioactive cytotoxicity assay or by flow cytometry (Weng et al., 2016a). All assays were performed in triplicate wells and repeated at least two times.

In Vivo Assay of TCL1-Specific TCR-T Cells Against Xenograft Tumors

For the Winn assay, $0.5 \times 10^6$ Mino-Luc cells and $5 \times 10^6$ TCL1-specific TCR gene-transduced or non-gene-modified T cells were suspended in 300 µL PBS and injected intravenously into the NSG mice (Non-Obese Diabetic/Severe Combined Immuno-Deficiency/IL-2 receptor γ-chain allelic mutation; NOD/Shi-scid/IL-2R γnull) aged 6-7 weeks (Central Institute for Experimental Animals). The growth of tumor was measured every 7 days until the mice died or were euthanized because of tumor progression. For adoptive transfer experiments, NSG mice aged 7 weeks were similarly inoculated with $0.5 \times 10^6$ of Mino-luc cells on day 0. Twelve days later, $10 \times 10^6$ TCL1-specific TCR gene-transduced or non-gene-modified T cells were intravenously administrated. The growth of tumor was measured as in Winn assay.

Statistical Analysis

The Student t test was used to compare various experimental groups. P values<0.05 were considered statistically significant. Unless otherwise indicated, mean and standard deviations are shown.

Example 2

TCL1-Specific T-Cell Receptor Redirects T Cells Against B Cell Lymphoma and Non-Hematological Tumor Cells To further explore the potential of TCL1 T-cell epitope as a therapeutic target for clinical immunotherapy, the above TCR was transduced into the HLA A2+ normal donors' PBMCs by lentivirus. It was observed that the TCR-transduced T cells specifically recognized TCL1 peptide-pulsed T2 cells at high avidity (1-10 nM) and lyse the HLA-A2+, TCL1-expressing B-cell lymphoma cell lines and primary lymphoma cells, but not normal B cells. Adoptive transfer of TCR-transduced T cells inhibited the growth of lymphoma cells in vivo and significantly extended the survival of mice. In addition, it was observed that TCL1 is expressed in the human embryonic stem cells and multiple types of solid tumor cells. TCL1-specific TCR-transduced T cells can recognize these solid tumor cells but not control tumor cells. These results suggest that TCL1-derived peptides are expressed in the context of HLA-A2 molecules on tumor cells and TCL1-TCR transduced T cells can be used for immunotherapy of B-cell malignancies as well as non-hematological tumors.

Figure 1B:
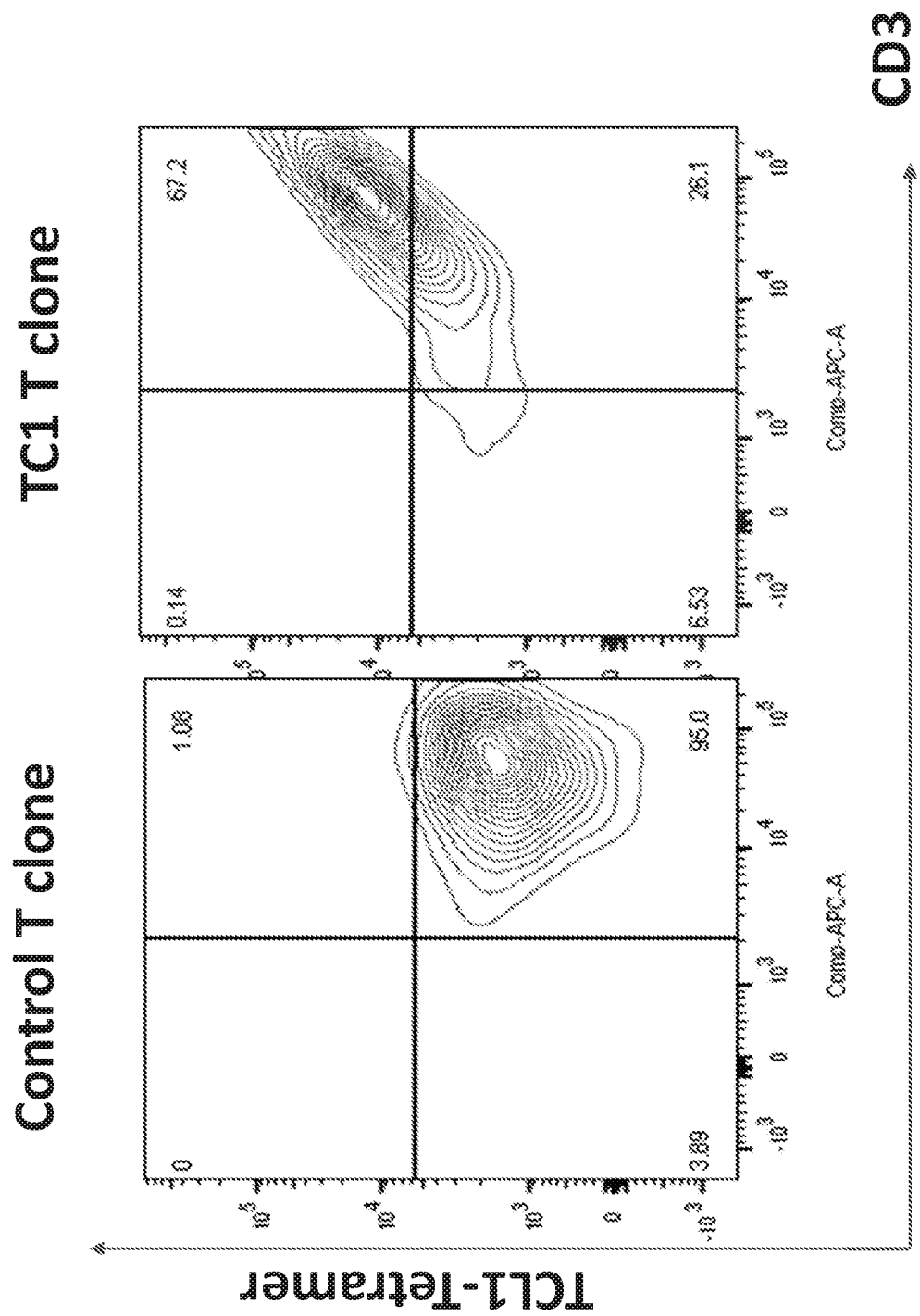

Characterization of HLA-A2-Restricted TCL1-Specific T Cell Clone and Cloning of the TCR α and β Genes In order to obtain the TCL1-specific T cell receptor gene, several TCL1-specific T clones were first generated by limiting dilution. One of the clones, termed TC1 showed high reactivity to the TCL1 peptide pulsed T2 cells by IFN-γ ELISA assay (FIG. 1A). TCL1$_{70-79}$ peptide-specific tetramer staining revealed the TC1 T clone is tetramer-positive (FIG. 1B). The RNA was then extracted from T clone and nanostring analysis of TCR α and β subfamilies was performed. It revealed the TC1 TCRs (hereafter referred to as TCL1-TCR) were composed of TRAV1-1, TRAJ57*01 F (b), TRAC and TRBV5-5, TRBJ2-7*01 F, TRBD2*01 F, TRBC2 subfamily sequences (FIG. 1C).

The Expression and Function of TCL1-TCR in the TCRαβ (−) J76 Cells

Figures 1C, 2A:
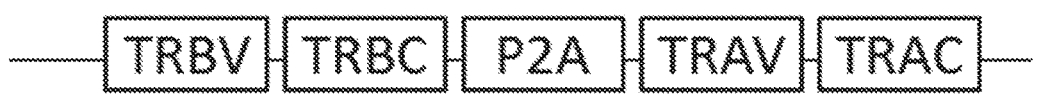
FIGS. 2A-D: Characterization of TCL1-TCR in Jurkat 76 cells.
Figure 2B:
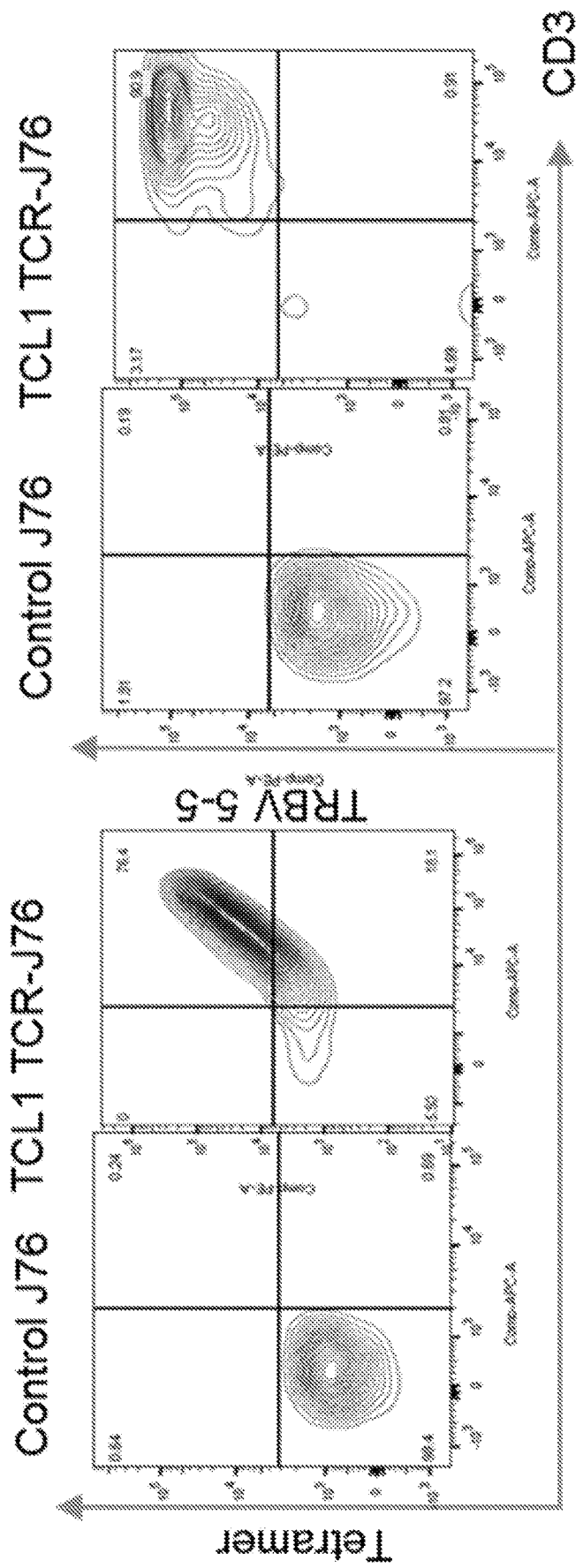
Figure 2C:
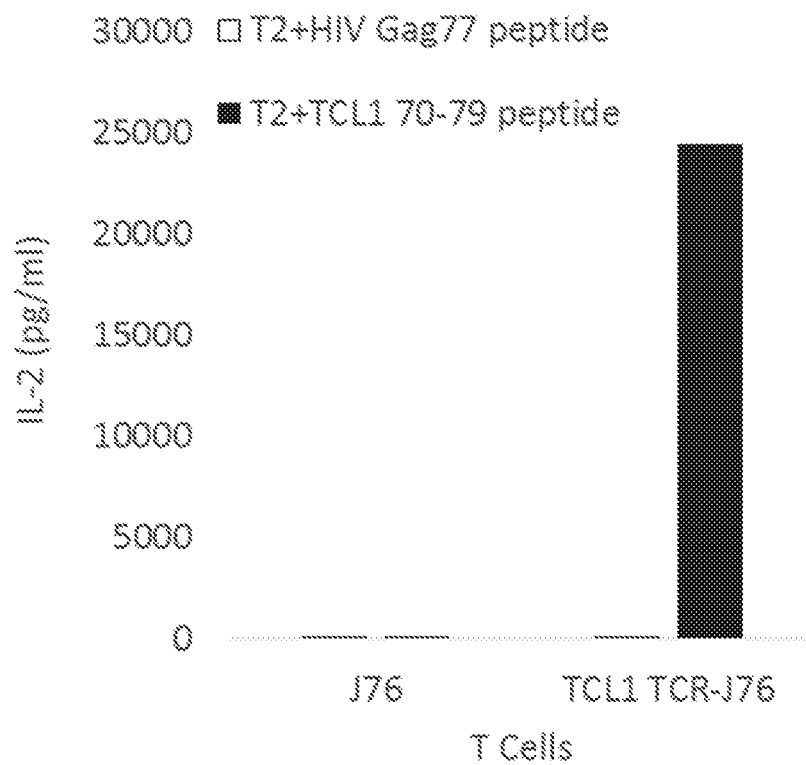
Figure 2D:
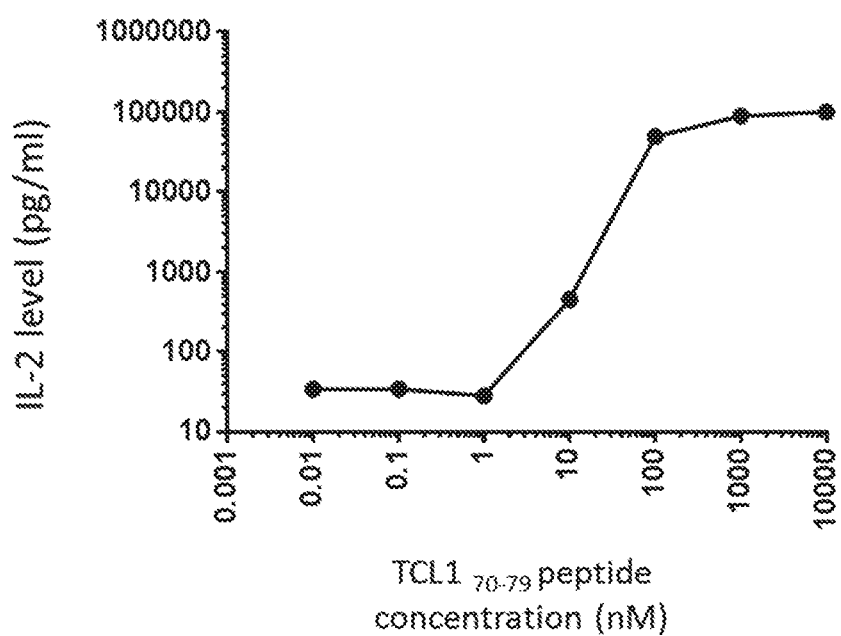
Figure 10:
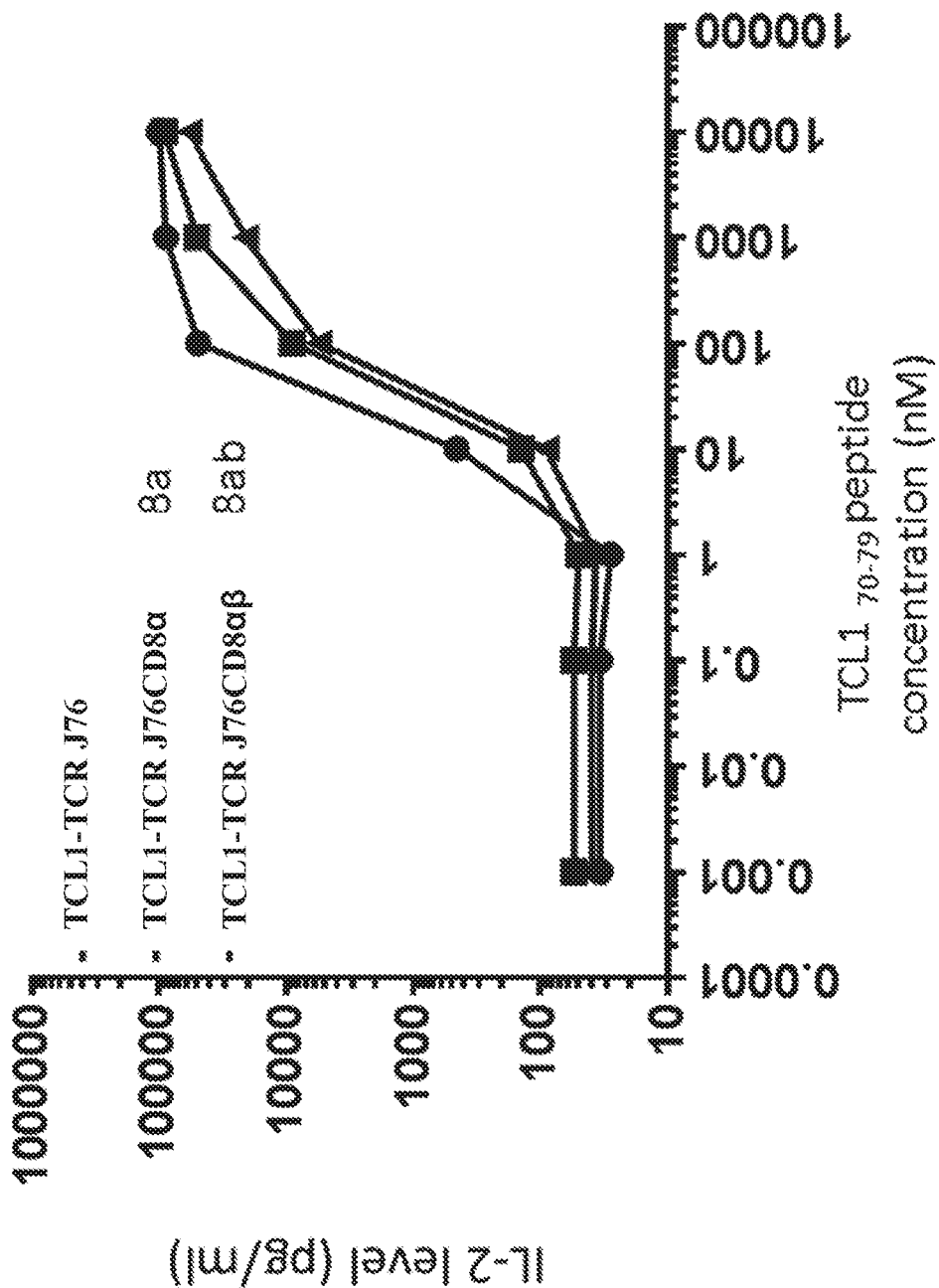
FIG. 10: Avidity assay of TCL1-TCR-transduced J76, J76CD8α, J76CD8αβ. TCL1-TCR-transduced J76, J76CD8α, J76CD8αβ cells were incubated with T2 cells pulsed with different concentration of TCL1 70-79 peptide overnight, and the level of IL-2 was measured by ELISA assay.

In order to determine the expression of TCL1-specific TCR, a P2A vector was generated that expressed TCRα and β in the same vector (FIG. 2A). The TCL1-TCR was transfected into the TCR αβ(−) J76 cells using a lentivirus. 48 hours after the transfection, the expression of TCL1-TCR was measured by flow cytometry. The inventors found the TCL1-TCR can be detected in TCR αβ(−) J76 cells by TC1-specific TRBV antibody and tetramer staining (FIG. 2B). In order to determine if the TCL1-TCR transfected J76 can specifically recognize the TCL1$_{70-79}$ peptide, the TCL1-TCR-transduced J76 cells were incubated with T2 cell pulsed with TCL1$_{70-79}$ peptide. The TCL1-TCR-transduced J76 cells but not untransduced J76 cells were observed to specifically secrete a large amount of IL-2 after incubation with TCL1$_{70-79}$ peptide-pulsed T2 cells, indicating the TCL1-TCR is functional (FIG. 2C). In order to determine the avidity of TCR, the TCL1-TCR-transduced J76 cells were incubated with T2 cell pulsed with different concentration of TCL1$_{70-79}$ peptide, it was found that the TCL1-TCR-transduced J76 can recognize the peptide at concentration of 1-10 nM, indicating that TCL1-TCR has moderate to high avidity (FIG. 2D)(23). Moreover, the inventors found that the TCL1-TCR is CD8-independent and the addition of CD8αα and CD8 αβ did not further increase the TCR avidity (FIG. 10).

The Expression and Function of TCL1-TCR in HLA A2+ Normal Donor T Cells

Figure 3A:
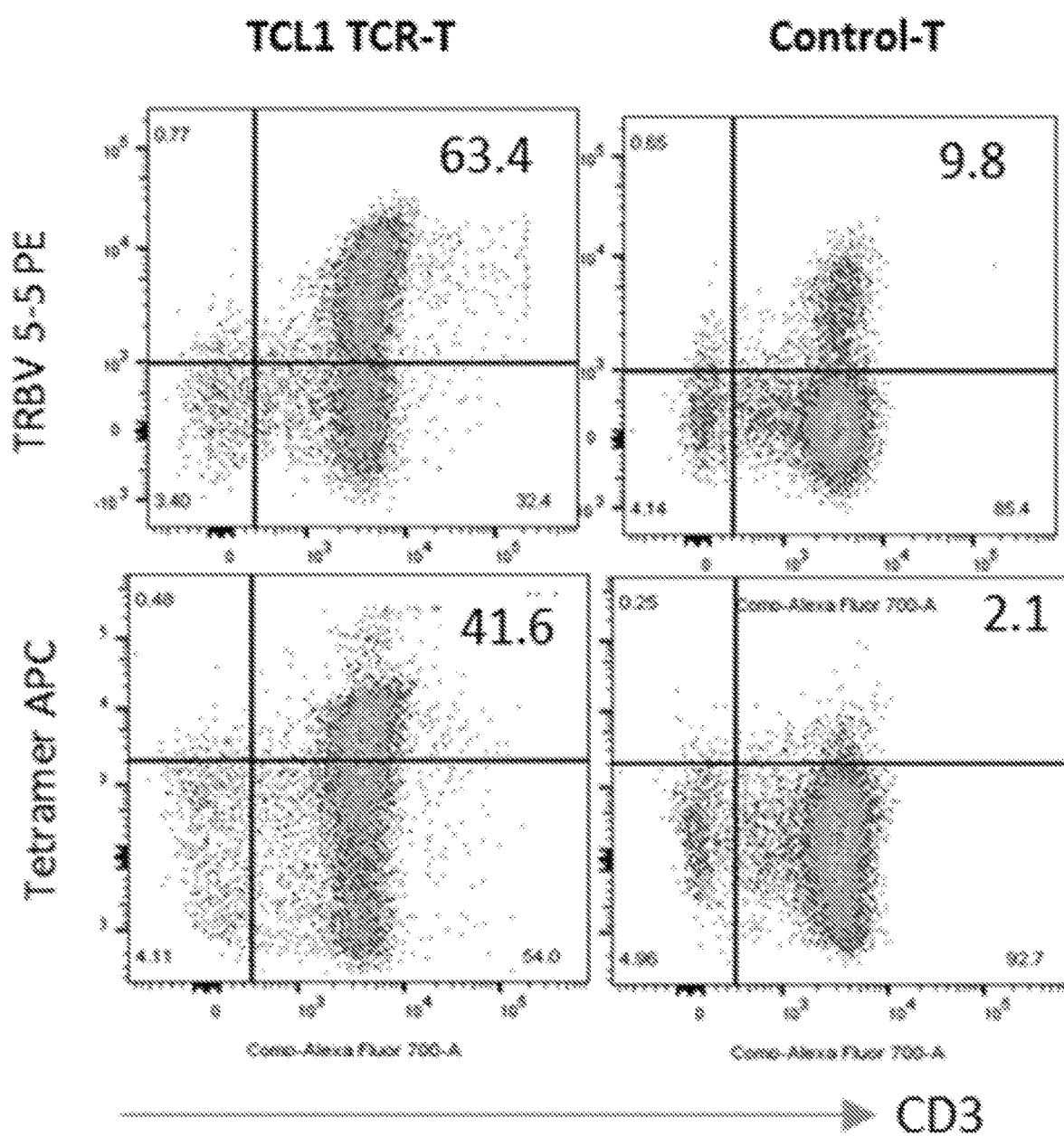
FIGS. 3A-D: Characterization of TCL1-TCR-transduced primary T cells.
Figure 3B:
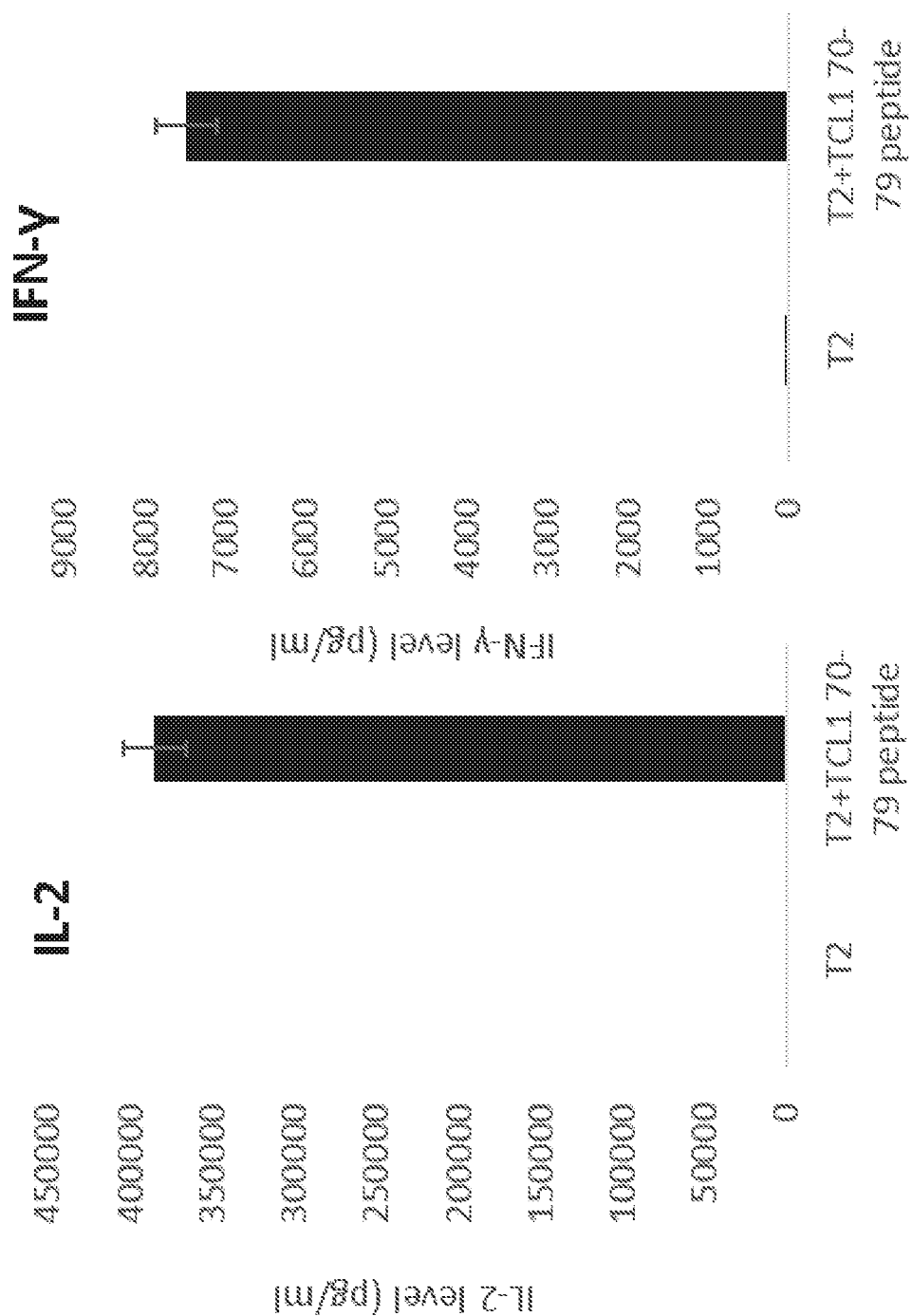
Figure 3C:
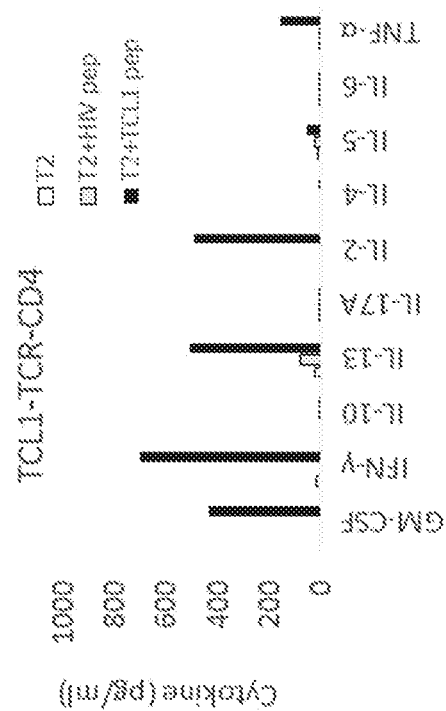
Figure 3C:
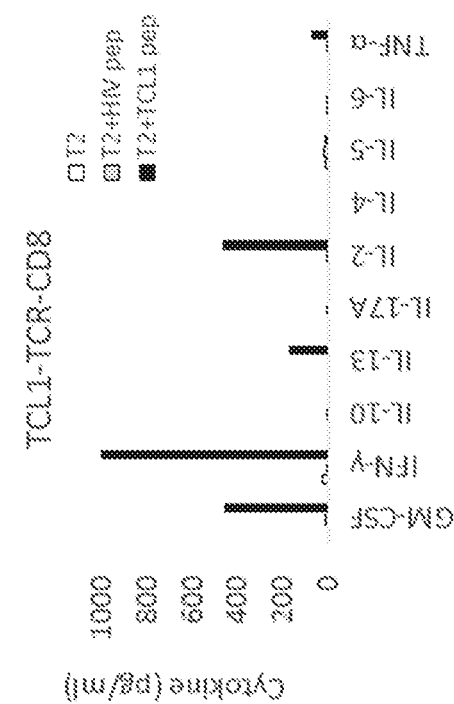
Figure 3D:
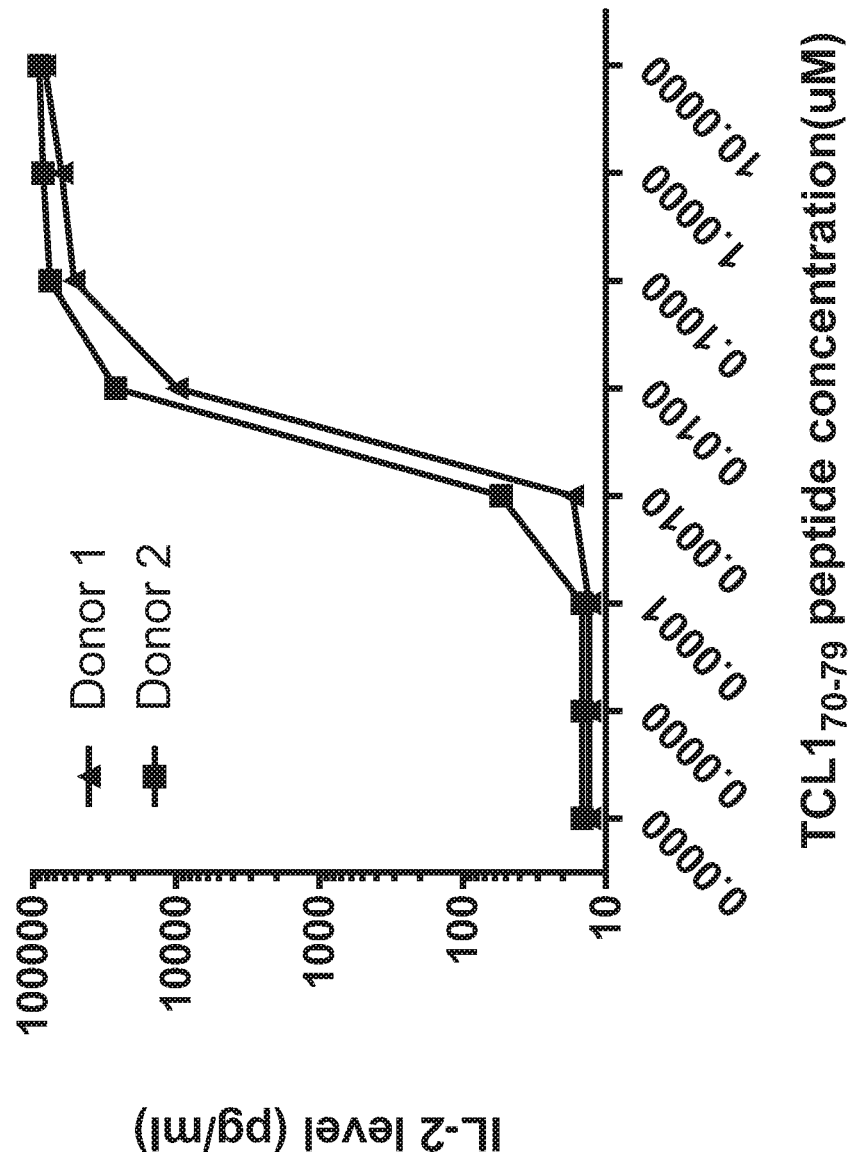

In order to determine if the TCL1-TCR can be expressed and function in primary T cells, the TCL1-TCR was transduced by lentivirus into OKT3-activated primary T cells, and it was observed that about 40-50% of T cells can express the TCL1-TCR by tetramer and TRBV antibody staining (FIG. 3A). In order to determine if TCL1-TCR is functional in the primary T cells, the TCL1-TCR-transduced T cells were incubated with T2 cells pulsed with TCL1$_{70-79}$ peptide. The TCL1-TCR-transduced T cells were observed to specifically secrete IFN-γ and IL-2 against peptide-pulsed T2 cells (FIG. 3B). Interestingly, both CD4 and CD8 T cells acquired the specific function with the TCL1-TCR, confirming that the TCR is CD8αβ-independent (FIG. 3C). The TCL1-TCR-transduced CD8 or CD4 T cells specifically secreted Th1/Tc1-type cytokines but not Th2/Tc2-type cytokines. Avidity assay revealed that the TCL1-TCR-transduced primary T cells recognized the peptide at 1-10 nM concentration, confirming that the TCR avidity is moderate to high (FIG. 3D).

Figure 4A:
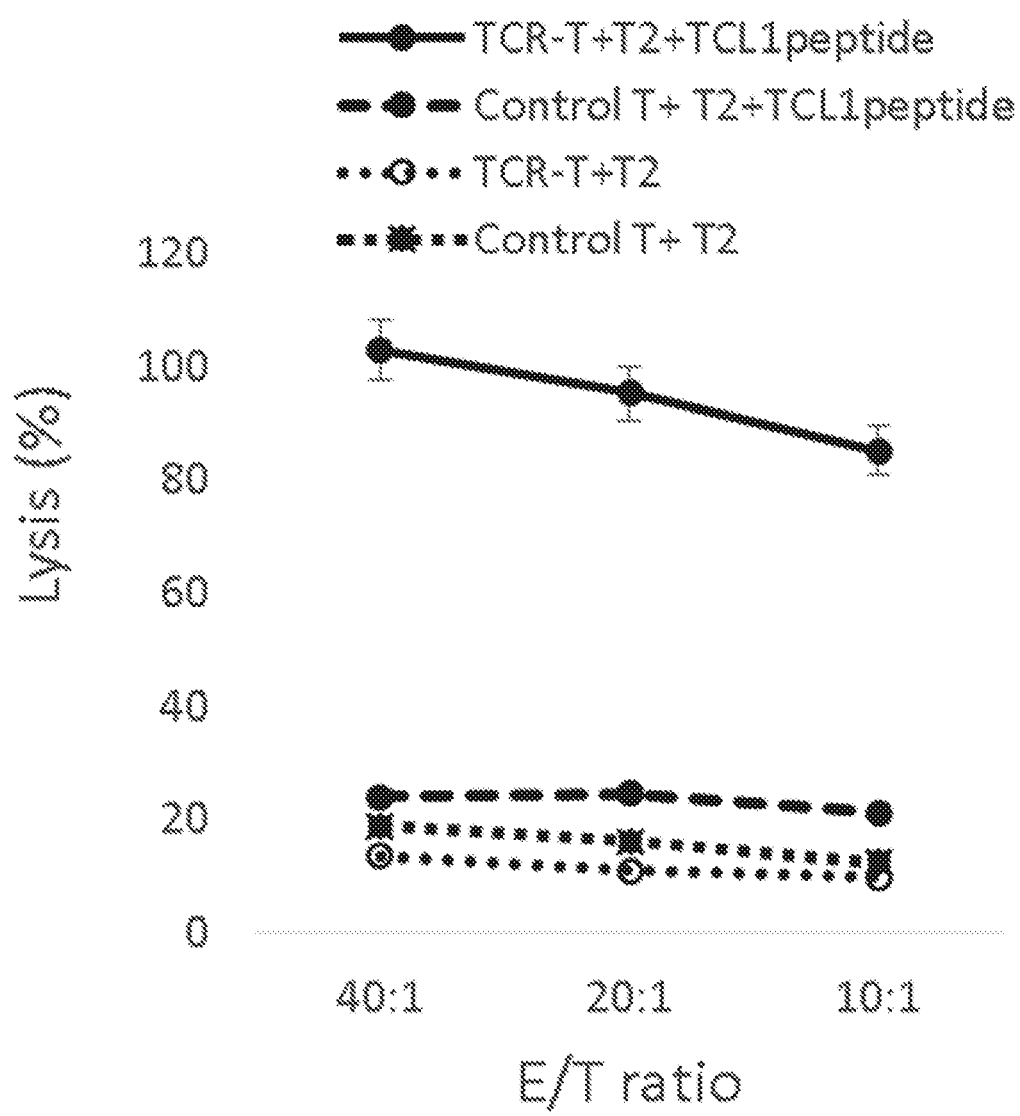
FIGS. 4A-C: Cytotoxicity assay of TCL1-TCR-transduced primary T cells.

The Recognition of Lymphoma Cell Lines and Primary Lymphoma Cells by TCL1-TCR-Transduced T Cells In order to determine if the TCL1-TCR-transduced primary T cells have cytotoxic function, the TCL1-TCR-transduced T cells were incubated with T2 cells pulsed with TCL1$_{70-79}$ peptide. The TCL1-TCR-transduced T cells were observed to specifically kill the TCL1$_{70-79}$ peptide-pulsed T2 cells but not control HIV peptide-pulsed T2 cells, indicating that the TCL1-TCR-transduced T cells have cytotoxic activity (FIG. 4A). The control untransduced T cells did not exhibit this function.

Figure 4B:
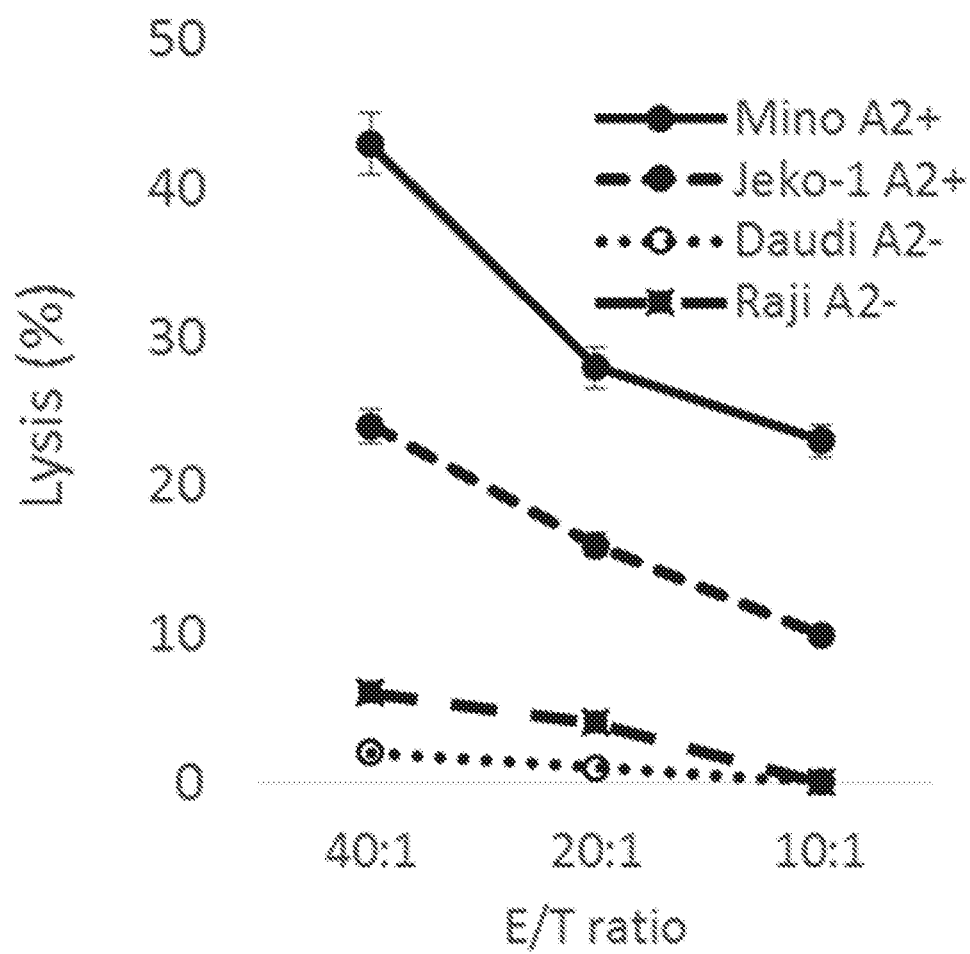
Figure 4C:
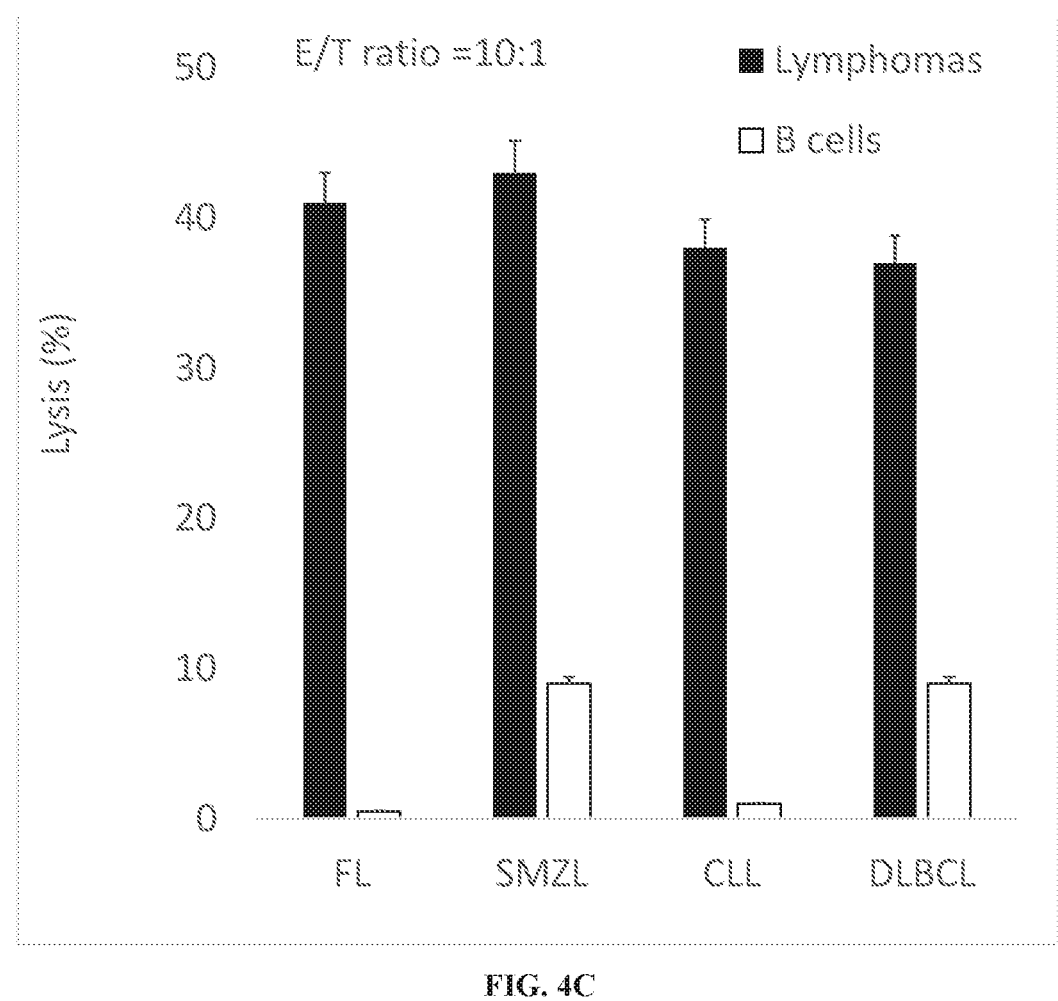

In order to determine if the TCL1-TCR-transduced T cells can specifically lyse lymphoma cells, the TCL1-TCR-transduced T cells were incubated with HLA A2+, TCL1-expressing lymphoma cell lines or primary lymphoma tumor cells derived from patients with CLL, MCL, FL, DLBCL and SMZL The inventors found the TCL1-TCR-transduced T cells can specifically lysed the lymphoma cell lines and primary lymphoma cells, but not HLA A2− lymphoma cell lines, or normal B cell derived from the same patient, indicating that the TCL1-TCR-transduced T cells can specifically target B-cell lymphoma tumor cells (FIGS. 4B-C).

TCL1-TCR-Transduced T Cell Exhibit Anti-Lymphoma Activity In Vivo

Figure 5A:
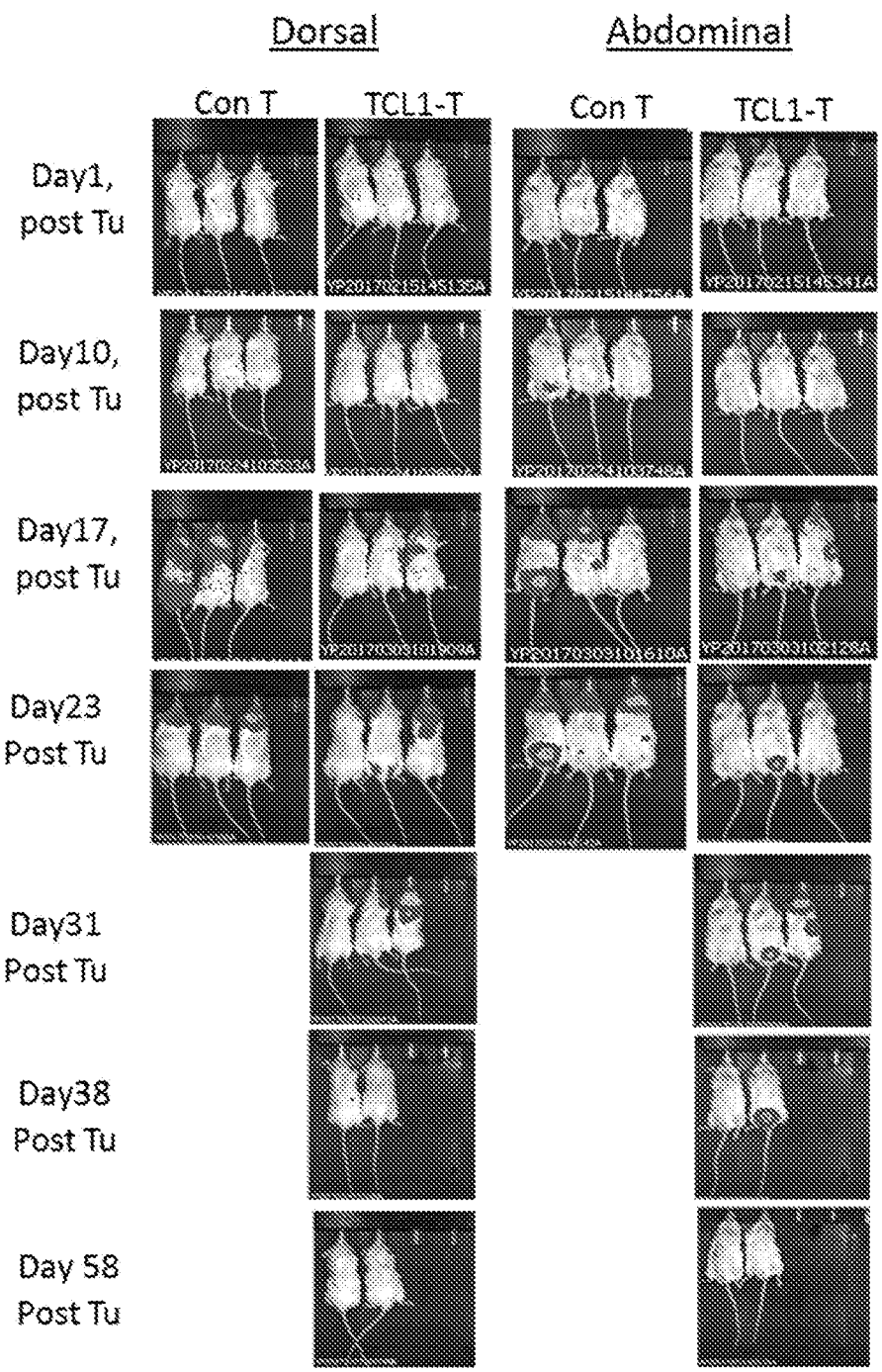
FIGS. 5A-D: In vivo assay of TCL1-TCR-transduced T cells against lymphoma cells.
Figure 5B:
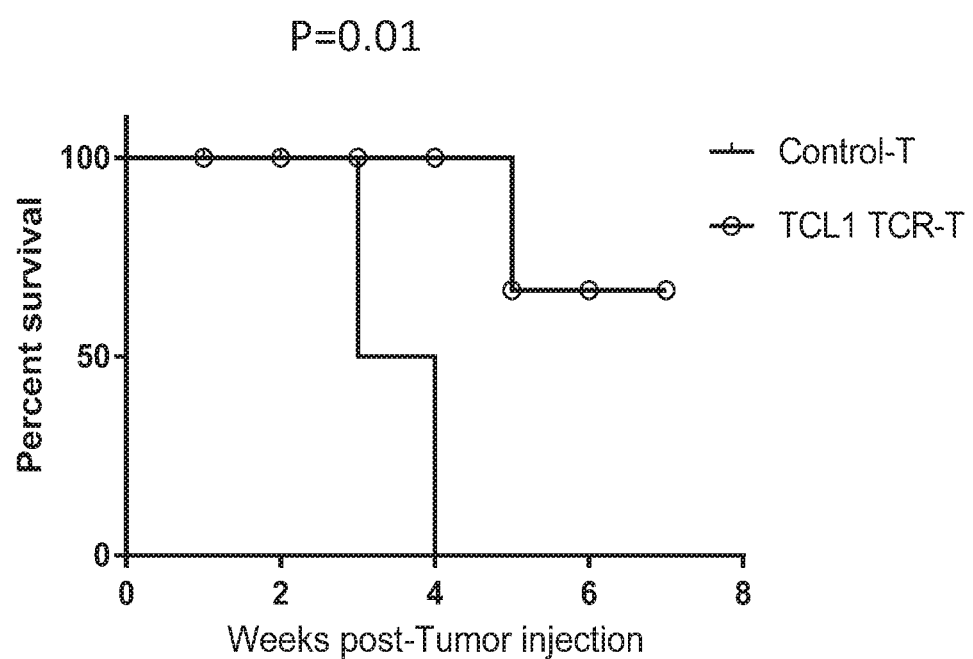
Figure 5C:
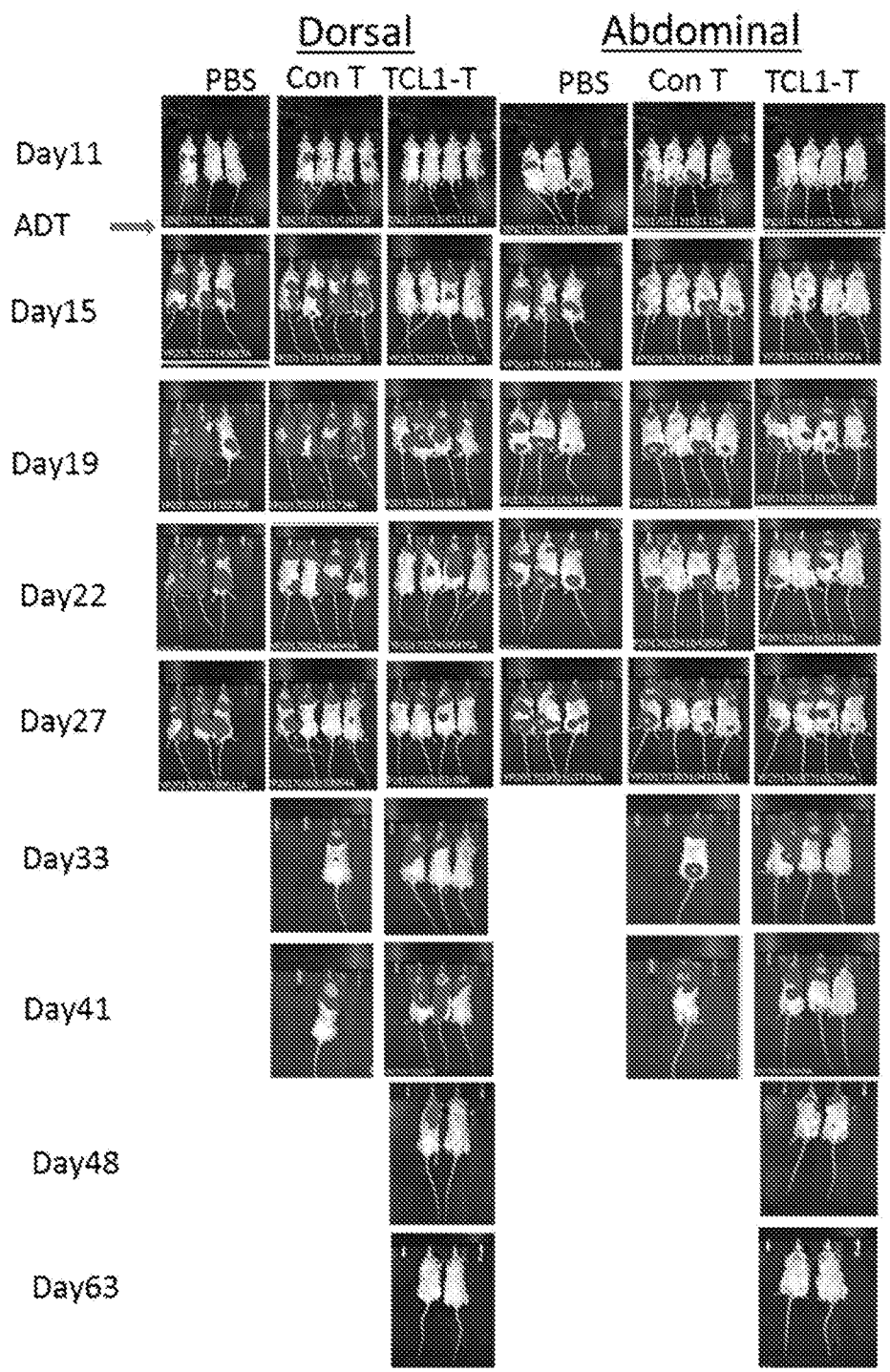
Figure 5D:
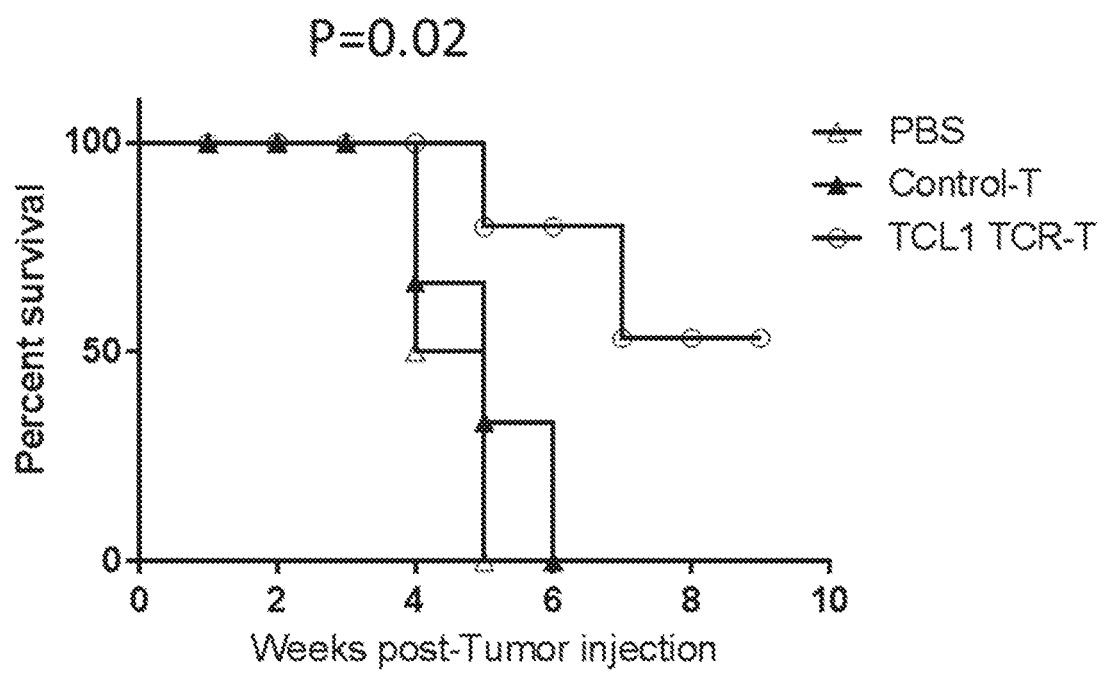

In order to determine if the TCL1-TCR-transduced T cell can inhibit tumor growth in vivo, the effect of TCL1-TCR-transduced T cells against luciferase-transduced Mino cells was tested in two experiments. In one setting (Winn assay), 5×10$^6$ TCL1-TCR-transduced T cells were co-injected with 0.5×10$^6$ luciferase-transduced Mino cells into immune-deficient mice, and it was observed that the TCL1-TCR-transduced T cells significantly inhibited tumor growth in vivo (FIG. 5A). In the second setting, 0.5×10$^6$ luciferase-transduced Mino cells were injected into immune deficient mice to establish tumor. After 12 days, mice were treated with 10×10$^6$ TCL1-TCR-transduced T cell. The inventors found TCL1-TCR transduced T cells but not control T cells significantly inhibited tumor growth and extended survival of mice (FIG. 5B).

The Expression of TCL1 in Embryonic Cells and Non-Hematological Tumor Cells

Figure 6A:
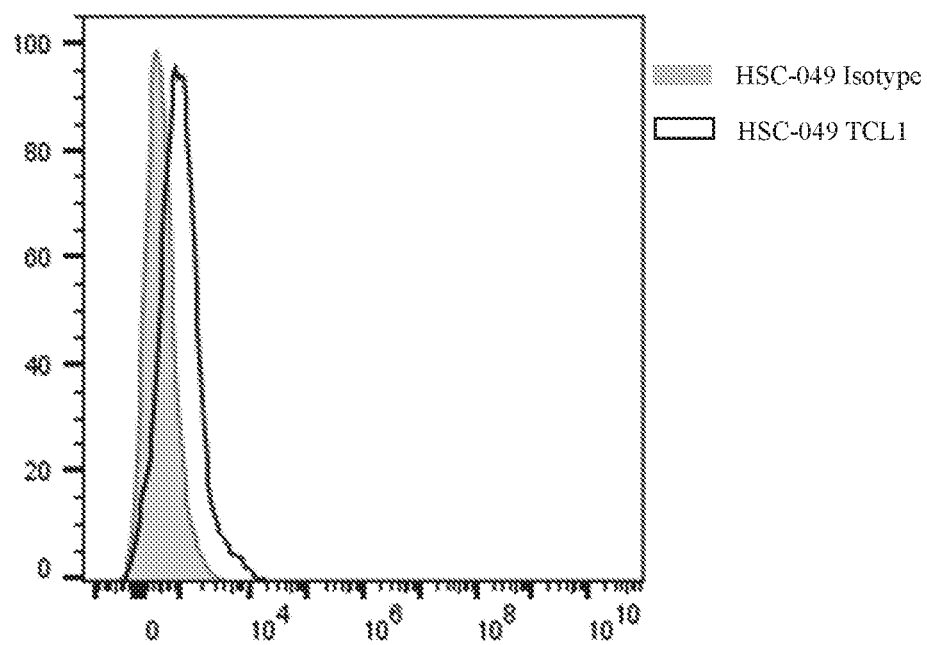
FIGS. 6A-C: The expression of TCL1 in embryonic cell line, hematological, and non-hematological tumor cells. The expression of TCL1 protein in embryonic cell line by intracellular staining (FIG. 6A) and real time PCR (FIG. 6B) are shown.
Figure 6B:
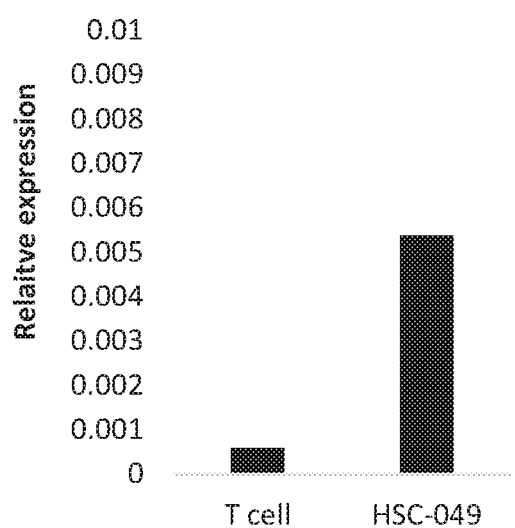
Figure 6C:
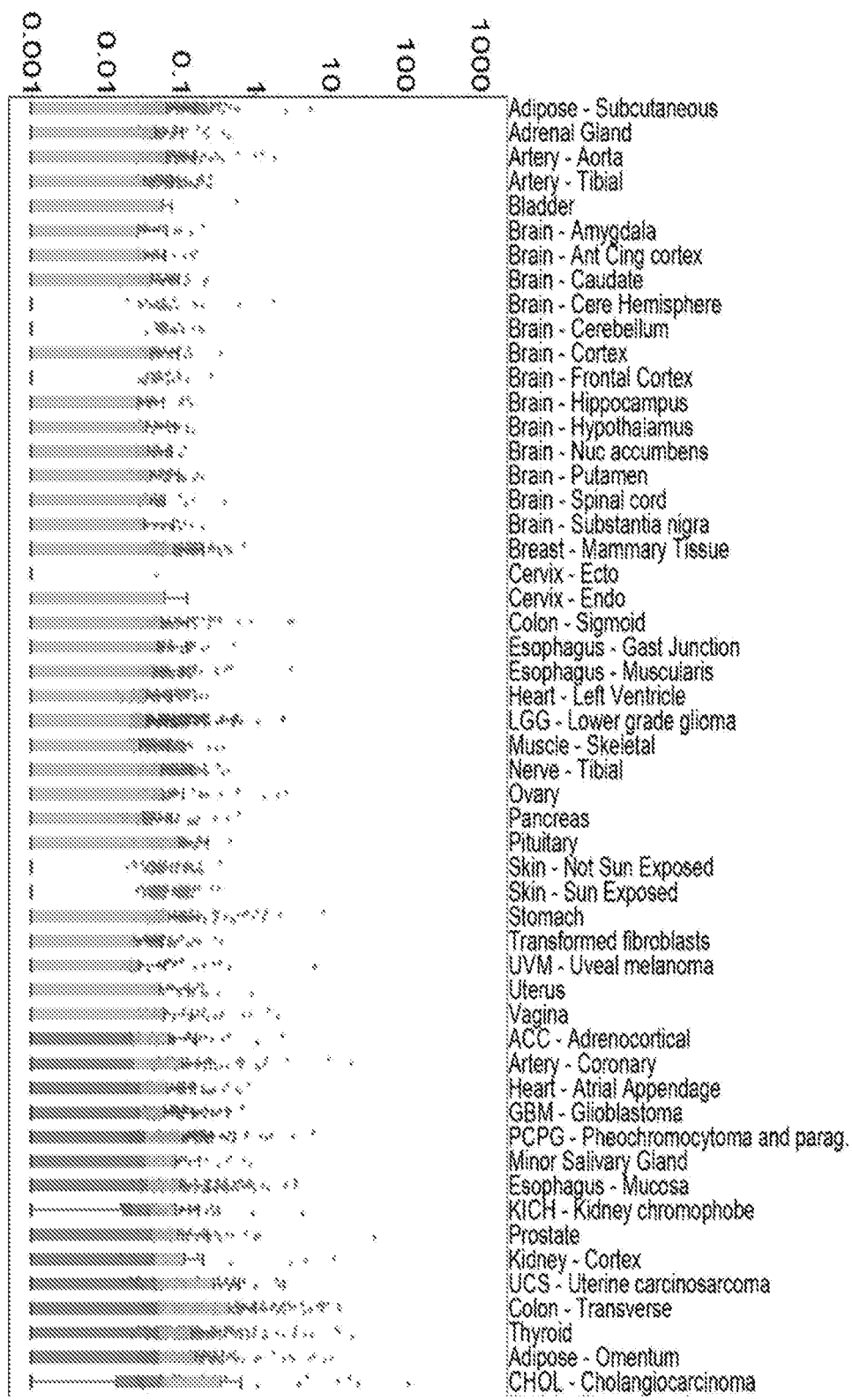
Figure 6C:
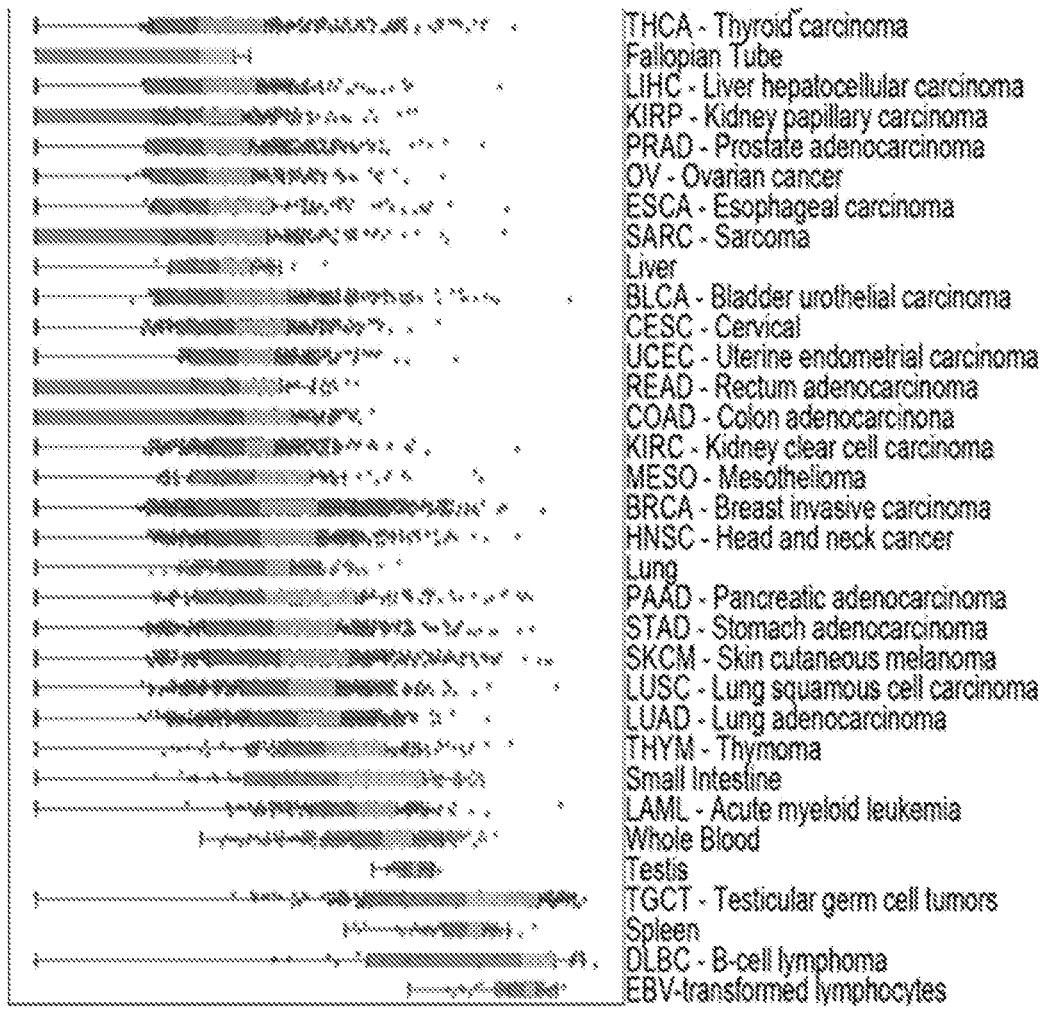

Previous studies have found that TCL1 is expressed in embryonic cells but not in adult tissues except B cells (Narducci et al., 2002). Consistent with this, we observed TCL1 expression in embryonic cell lines (ESI-049, SKU: ES-702; www.esibio.com/index.php/products/product-category/cell-lines/esi-049-human-embryonic-stem-cell-line-46-xy/, from ESI BIO) by intracellular staining and real-time PCR assay (FIGS. 6A-B). Moreover, analysis of TCGA database showed that TCL1 is overexpressed in multiple non-hematological tumors but not in the normal tissues except B-cell-rich organs like lymph node, tonsil, and spleen, which is consistent with previous reports (FIG. 6C).

Figure 7A:
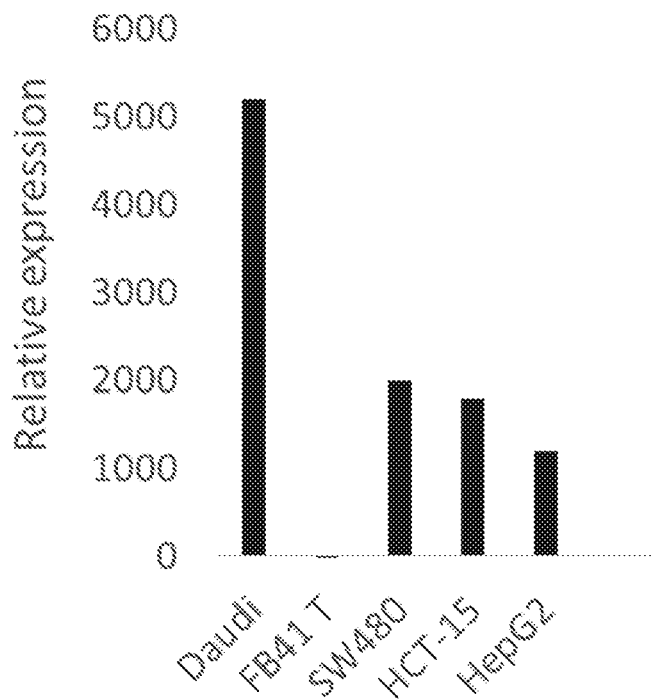
FIGS. 7A-C: The cytotoxicity of TCL1-TCR-T against solid tumors. The expression of TCL1 in solid tumor cell line HCT-15, SW480, HepG2 by intracellular staining (FIG. 7A) and real time PCR (FIG. 7B) are shown.
Figure 7B:
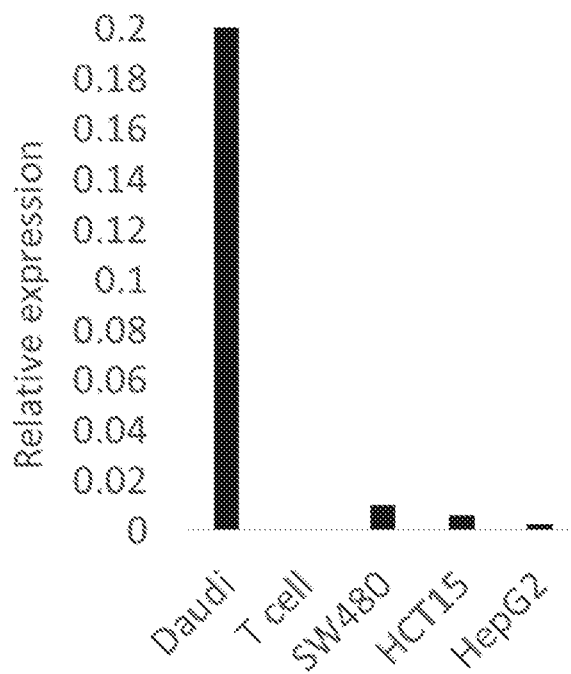
Figure 7C:
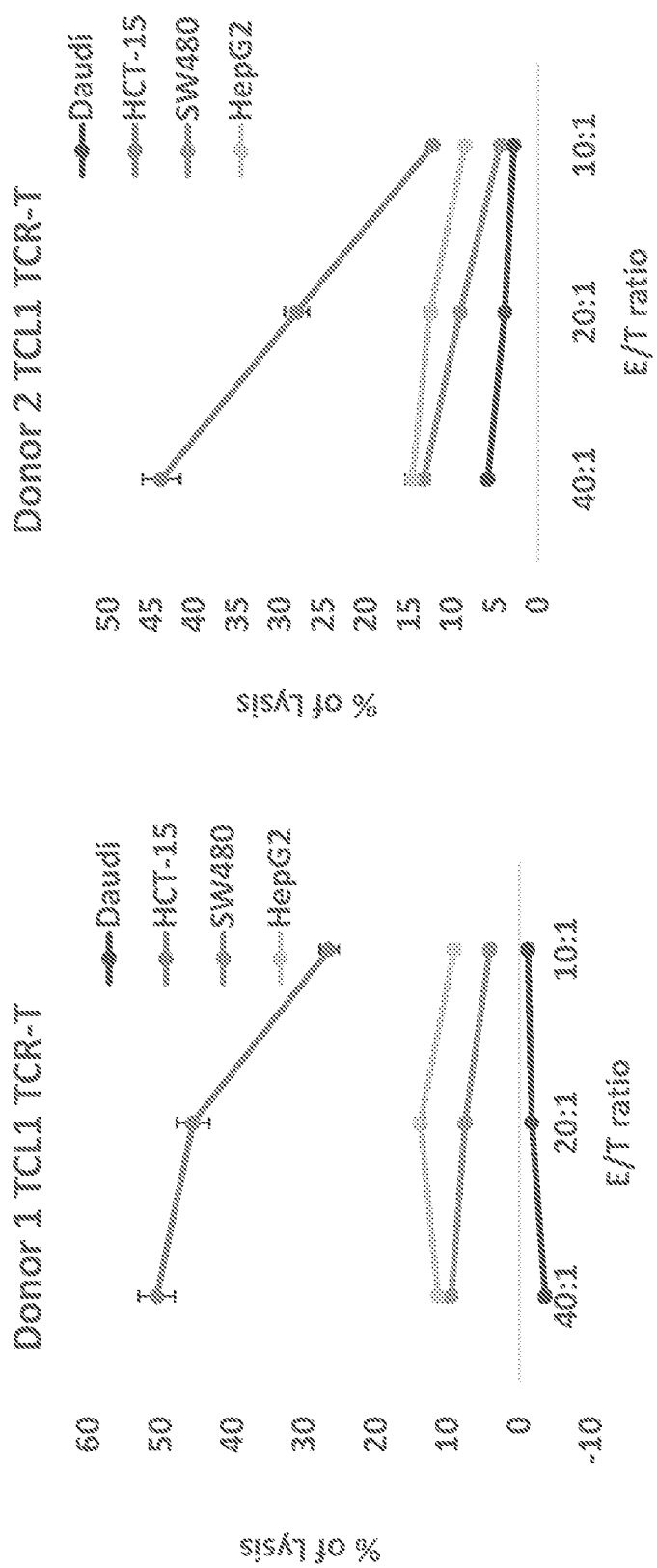

Cytotoxic Activity of TCL1-TCR-Transduced T Cells Against Non-Hematological Tumor Cell Lines In order to determine if TCL1-TCR-transduced T cells can target TCL1-expressing solid tumor cancer cells, 3 HLA A2+, human solid tumor cell lines (SW480, HCT-15, HepG2) were collected. TCL1 was expressed in all of these solid tumor cell lines by intracellular staining and real-time PCR assay (FIGS. 7A-B). In co-culture assays, TCL1-TCR-transduced T cells specifically lysed these tumor cells in vitro, but not HLA A2− control tumor cells (FIGS. 7C-D).

Safety of TCL1-TCR-Transduced T Cells.

Figure 8B:
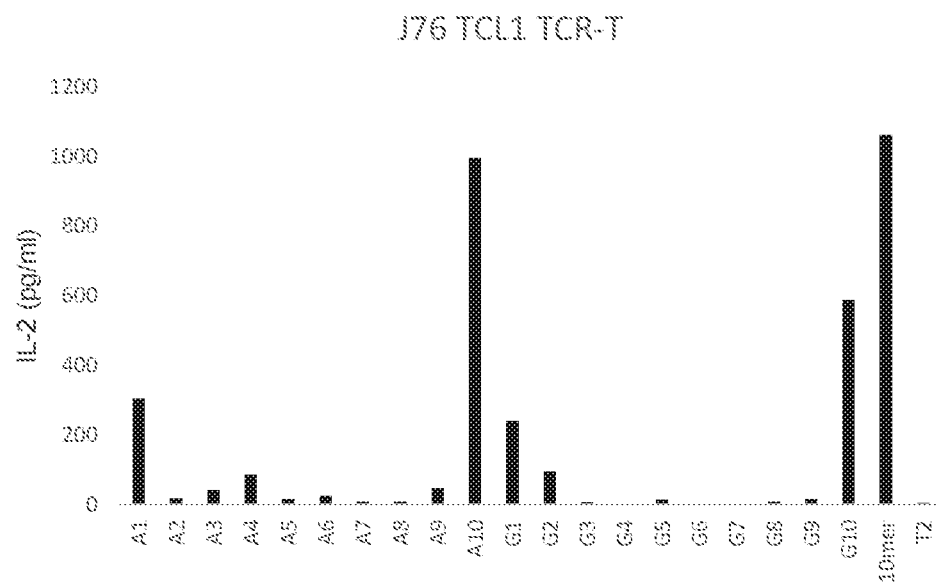
Figure 8C:
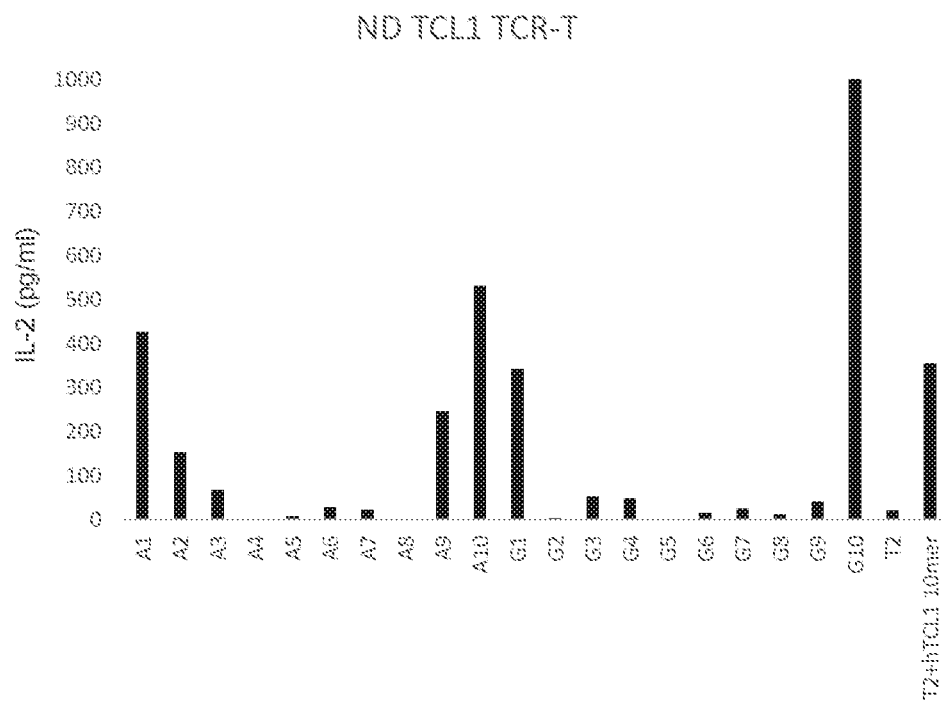
Figure 9A:
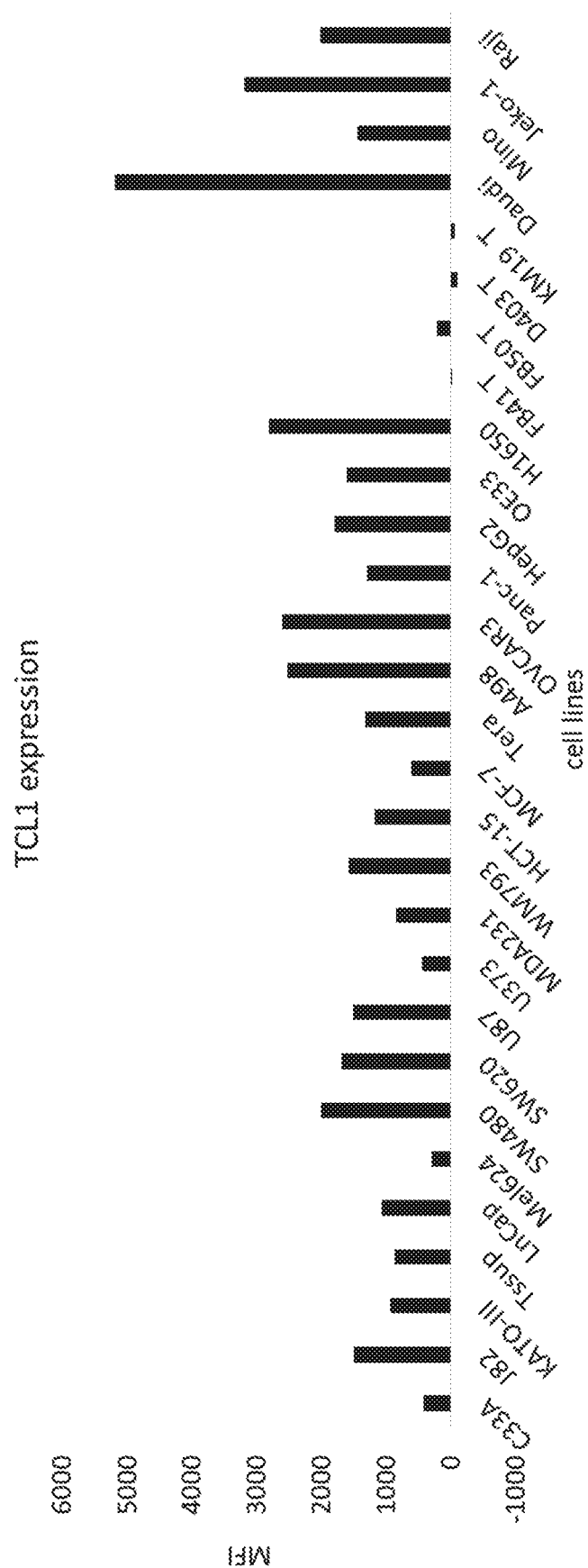
FIGS. 9A-B.
Figure 9B:
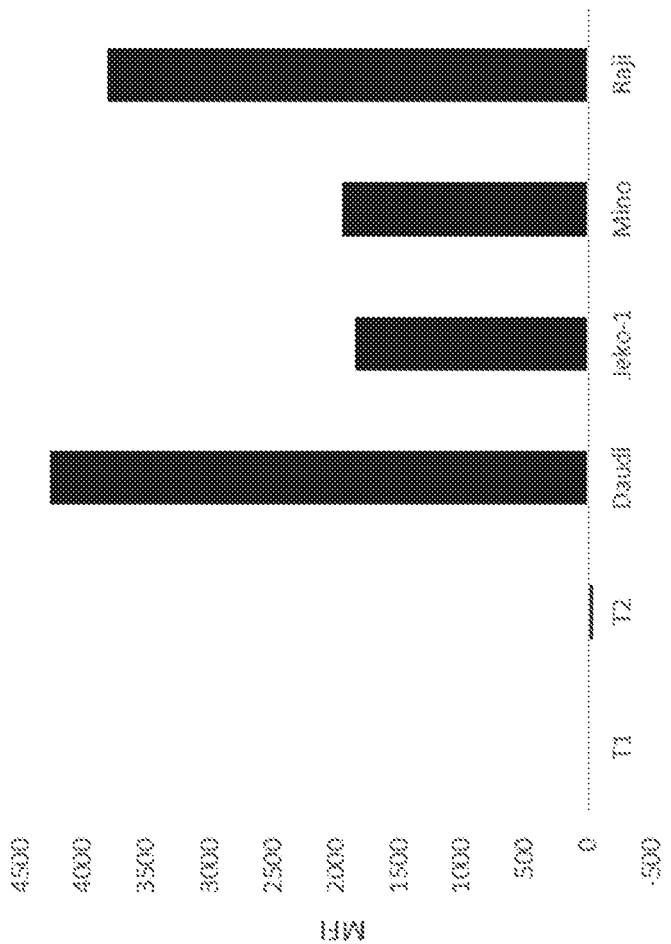

Alanine and glycine replacement assays of the TCL1$_{70-79}$ peptide (FIG. 8A) demonstrated that the middle 8 amino acids "LLPIMWQL" (SEQ ID NO: 33) of TCL1$_{70-79}$ epitope (SLLPIMWQLY; SEQ ID NO: 29) were critical residues for recognition by TCL1-TCR-transduced T cells as replacement of any of these 8 amino acids abrogated their reactivity. The first (S) and last (Y) amino acids of the epitope were found to be not critical for recognition by TCL1-TCR-transduced J76 or primary (ND, normal donor) T cells (FIGS. 8B-C). Blast search of LLPIMWQL (SEQ ID NO: 33) sequence against known proteins in the reference database did not reveal any homology with proteins other than TCL1, indicating that TCL1-TCR-transduced T cells are unlikely to have on-target off-tumor effect and could be safe for adoptive T cell therapy.

Adoptive T cell transfer with CD19 CAR T cells have shown promising clinical responses in lymphoma patients, however, relapse is common. Most of the relapsed lymphomas are CD19 negative suggesting antigen loss as a mechanism of immune escape (Sotillo et al., 2015; Topp et al., 2014; Neelapu et al., 2017). Therefore, novel T cell therapy strategies targeting other tumor antigens are needed to further improve outcomes in patients with B-cell malignancies. In the above experiments, TCL1-TCR-transduced T cells targeting B-cell oncoprotein TCL1 were shown to be effective against multiple types of B-cell malignancies. In addition, they were effective against TCL1-expressing solid tumor cells, but did not target normal B cells or control tumor cells that lack TCL1 or HLA-A2. Collectively, these results indicate that TCL1-TCR-transduced T cells can be used as an immunotherapy strategy to treat TCL1-expressing cancers such as B-cell malignancies and non-hematological tumors.

Genetic modification of normal T cells with T cell receptor has been an effective way to redirect the specificity of T cells against tumors (Fesnak et al., 2016). Compared to the popular CAR T therapy, there are some limitations that hindered the success of TCR-T immunotherapy. For example, the avidity of TCRs is generally lower than CARs, there is potential for mismatched pairing of α and β chains of transduced TCRs with endogenous TCRs, and there may be cross-recognition of degenerate peptides derived from other proteins that may result in toxicity (Kunert et al., 2013). We used several strategies to minimize these limitations. To minimize mismatch pairing, we introduced cysteine mutations into the constant regions of TRAC and TRBC (Cohen et al., 2007) and also codon optimized the TCL1-TCR (van Loenen et al., 2011). High avidity TCRs have been reported to be associated with better tumor killing ability than low avidity TCRs (Stone et al., 2015; Johnson et al., 2009). However, very high avidity TCRs may be associated with cross-reactivity and off-target toxicity (Linette et al., 2013; Morgan R et al., 2013; Holler et al., 2003). TCRs of 10 µM avidity are capable of mediating killing of tumor cells without inducing GVHD (Zhong et al., 2013). The inventors have isolated a TCL1-TCR of 1-10 nM avidity, which is considered to be moderate to high (Kunert et al., 2013). In the above experiments, the inventors found that the TCL1-TCR of this avidity can mediate significant tumor lysis without causing auto-reactivity, indicating that this TCR is likely to be effective against tumor. Furthermore, the absence of homology of the critical amino acid sequence, LLPIMWQL (SEQ ID NO: 33), to other human proteins supports the idea that this TCL1-TCR is likely to be safe in clinic (Cameron et al., 2013).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,373,071
U.S. Pat. No. 4,458,066
U.S. Pat. No. 4,598,049
U.S. Pat. No. 4,897,268
U.S. Pat. No. 5,075,109
U.S. Pat. No. 5,552,157
U.S. Pat. No. 5,565,213
U.S. Pat. No. 5,567,434
U.S. Pat. No. 5,738,868
U.S. Pat. No. 5,741,516
U.S. Pat. No. 5,770,219
U.S. Pat. No. 5,783,208
U.S. Pat. No. 5,795,587
U.S. Pat. No. 5,797,898
U.S. Pat. No. 6,225,042
U.S. Pat. No. 6,355,479
U.S. Pat. No. 6,362,001
U.S. Pat. No. 6,451,995

U.S. Pat. No. 6,790,662
U.S. Pat. No. 7,446,190
U.S. Pat. No. 8,252,592
U.S. Pat. No. 8,339,645
U.S. Pat. No. 8,398,282
U.S. Pat. No. 7,446,179
U.S. Pat. No. 6,410,319
U.S. Pat. No. 7,070,995
U.S. Pat. No. 7,265,209
U.S. Pat. No. 7,354,762
U.S. Pat. No. 7,446,190
U.S. Pat. No. 7,446,191
U.S. Pat. No. 7,666,604
U.S. Pat. No. 8,324,353
U.S. Pat. No. 8,479,118
U.S. Patent Appl. No. 2005/0065463
U.S. Patent Appl. No. 2002/131960
U.S. Patent Appl. No. 2013/287748
U.S. Patent Appl. No. 2013/0149337
U.S. Patent Appl. No. 2009/0017000
U.S. Patent Appl. No. 2009/0004142
U.S. Patent Appl. No. 2005/0065463
EP 2537416
WO 2000/14257
WO 2007/103009
WO 2012/129514
WO 2013/071154
WO 2013/123061
WO 2013/126726
WO 2013/166321
WO 2014/031687
WO 2014/055668
WO 99/60120
Aggarwal et al., TCL1A expression delineates biological and clinical variability in B-cell lymphoma. Mod Pathol.; 22(2):206-15, 2008.
Altenschmidt et al., Adoptive transfer of in vitro-targeted, activated T lymphocytes results in total tumor regression, J Immunol. 1997 Dec. 1; 159(11):5509-15.
Amini et al., The expressions of stem cell markers: Oct4, Nanog, Sox2, nucleostemin, Bmi, Zfx, Tcl1, Tbx3, Dppa4, and Esrrb in bladder, colon, and prostate cancer, and certain cancer cell lines. Anatomy & cell biology; 47(1):1-11, 2014.
Ausubel et al., Current Protocols in Molecular Biology, Greene Publishing Associates and John Wiley & Sons, NY, 1994.
Beck and Blanpain, Unravelling cancer stem cell potential. Nat Rev Cancer; 13(10):727-38, 2013.
Bichi et al., Human chronic lymphocytic leukemia modeled in mouse by targeted TCL1 expression. Proceedings of the National Academy of Sciences of the United States of America; 99(10):6955-60, 2002.
Brocker et al., *Adv. Immunol.,* 68:257, 1998.
Cameron et al., Identification of a Titin-Derived HLA-A1-Presented Peptide as a Cross-Reactive Target for Engineered MAGE A3-Directed T Cells. Science Translational Medicine; 5(197):197ra03-ra03, 2013.
Chao M P, Treatment challenges in the management of relapsed or refractory non-Hodgkin's lymphoma—novel and emerging therapies. Cancer Management and Research; 5:251-69, 2013.
Chothia et al., EMBO J. 7:3745, 1988.
Cohen et al., Enhanced Antitumor Activity of T Cells Engineered to Express T-Cell Receptors with a Second Disulfide Bond. Cancer research; 67(8):3898-903, 2007.
Davila et al., PLoS ONE 8(4): e61338, 2013.
Eshhar et al., Specific activation and targeting of cytotoxic lymphocytes through chimeric single chains consisting of antibody-binding domains and the gamma or zeta subunits of the immunoglobulin and T-cell receptors. Proc Natl Acad Sci USA.; 90(2):720-4, 1993.
Eshhar, Tumor-specific T-bodies: towards clinical application. Cancer Immunol Immunother. 1997 November-December; 45(3-4):131-6. 1997
Fedorov et al., Sci. Transl. Medicine, 5(215), December, 2013.
Fesnak et al., Engineered T cells: the promise and challenges of cancer immunotherapy. Nat Rev Cancer; 16(9):566-81, 2016.
Fitzer-Attas et al., *J Immunol.* 160(1):145-54, 1998.
Goeddel, *Methods Enzymol.,* 185:3-7, 1990.
Gross et al. (1992) Endowing T cells with antibody specificity using chimeric T cell receptors. FASEB J. 1992 December; 6(15):3370-8.
Harris and Kranz, Adoptive T Cell Therapies: A Comparison of T Cell Receptors and Chimeric Antigen Receptors. Trends in Pharmacological Sciences; 37(3):220-30, 2016.
Heemskerk et al. Hum Gene Ther. 19:496-510, 2008.
Hekele et al. Growth retardation of tumors by adoptive transfer of cytotoxic T lymphocytes reprogrammed by CD44v6-specific scFv:zeta-chimera. Int J Cancer. 1996 Oct. 9; 68(2):232-8, 1996.
Herling et al., High TCL1 levels are a marker of B-cell receptor pathway responsiveness and adverse outcome in chronic lymphocytic leukemia. Blood, 2009.
Herling et al., TCL1 in B-cell tumors retains its normal b-cell pattern of regulation and is a marker of differentiation stage. Am J Surg Pathol.; 31(7):1123-9, 2007.
Holler et al., TCRs with high affinity for foreign pMHC show self-reactivity. Nature immunology; 4(1):55-62, 2003.
Hoyer et al., Dysregulated TCL1 promotes multiple classes of mature B cell lymphoma. Proceedings of the National Academy of Sciences; 99(22):14392-7, 2002.
Hwang and Palin, TCR ITAM multiplicity is required for the generation of follicular helper T-cells; 6:6982, 2015.
Hwu et al. (1995) In vivo antitumor activity of T cells redirected with chimeric antibody/T-cell receptor genes. Cancer Res. 1995 Aug. 1; 55(15):3369-73.
Irvine et al., Direct observation of ligand recognition by T cells. Nature; 419(6909):845-9, 2002.
Jackson et al., Driving CAR T-cells forward. Nat Rev Clin Oncol.; 13(6):370-83, 2016.
Jensen and Riddell, Designing chimeric antigen receptors to effectively and safely target tumors. Current Opinion in Immunology; 33(Supplement C):9-15, 2015.
Johnson and June, Driving gene-engineered T cell immunotherapy of cancer. Cell Res.; 27(1):38-58, 2017.
Johnson et al., Gene therapy with human and mouse T-cell receptors mediates cancer regression and targets normal tissues expressing cognate antigen. Blood; 114(3):535-46. 2009.
Jores et al., PNAS U.S.A. 87:9138, 1990.
Kabat et al., "Sequences of Proteins of Immunological Interest, US Dept. Health and Human Services, Public Health Service National Institutes of Health, 5th ed, 1991.
Kim et al., *Nature,* 22(4):403-410, 2004.
Kochenderfer et al., Chemotherapy-refractory diffuse large B-cell lymphoma and indolent B-cell malignancies can be effectively treated with autologous T cells expressing an anti-CD19 chimeric antigen receptor. J Clin Oncol; 33(6): 540-9, 2015.

Kuball et al., Increasing functional avidity of TCR-redirected T cells by removing defined N-glycosylation sites in the TCR constant domain. The Journal of Experimental Medicine; 206(2):463-75, 2009.

Kunert et al., TCR-engineered T cells meet new challenges to treat solid tumors: choice of antigen, T cell fitness and sensitisation of tumor milieu (review). Frontiers in Immunology; 4. 2013.

Lee et al., A novel strategy for rapid and efficient isolation of human tumor-specific CD4+ and CD8+ T-cell clones. Journal of Immunological Methods; 331(1-2):13-26, 2008.

Lefranc et al., Dev. Comp. Immunol. 27:55, 2003.

Linette et al., Cardiovascular toxicity and titin cross-reactivity of affinity-enhanced T cells in myeloma and melanoma. Blood; 122(6):863-71, 2013.

Locke et al., Phase 1 Results of ZUMA-1: A Multicenter Study of KTE-C19 Anti-CD19 CAR T Cell Therapy in Refractory Aggressive Lymphoma. Mol Ther.; 25(1):285-95, 2017.

Malissen et al., Altered T cell development in mice with a targeted mutation of the CD3-epsilon gene. The EMBO Journal; 14(19):4641-53, 1995.

Morgan R et al., Cancer regression and neurological toxicity following anti-MAGE-A3 TCR gene therapy. Journal of immunotherapy (Hagerstown, Md.: 1997); 36(2):133-51. 2013.

Moritz et al. (1994) Cytotoxic T lymphocytes with a grafted recognition specificity for ERBB2-expressing tumor cells. Proc Natl Acad Sci USA. 1994 May 10; 91(10): 4318-22.

Narducci et al., TCL1 participates in early embryonic development and is overexpressed in human seminomas. Proceedings of the National Academy of Sciences; 99(18): 11712-7, 2002.

Neelapu et al., Axicabtagene ciloleucel CAR T-cell therapy in refractory large B-cell lymphoma. N Engl J Med. 2017 Dec. 28; 377(26):2531-2544.

Newick et al., Chimeric antigen receptor T-cell therapy for solid tumors. Molecular Therapy Oncolytics; 3:16006, 2016.

Nguyen et al., Cancer stem cells: an evolving concept. Nat Rev Cancer; 12(2):133-43, 2012.

Nishimura et al., A Role for KLF4 in Promoting the Metabolic Shift via TCL1 during Induced Pluripotent Stem Cell Generation. Stem Cell Reports; 8(3):787-801, 2017.

Novellino et al., A listing of human tumor antigens recognized by T cells: March 2004 update. Cancer Immunology, Immunotherapy; 54(3):187-207, 2005.

Peitzsch et al., Cancer stem cells: The root of tumor recurrence and metastases. Seminars in cancer biology; 44:10-24, 2017.

Plosker and Figgitt, Rituximab: a review of its use in non-Hodgkin's lymphoma and chronic lymphocytic leukaemia. Drugs; 63(8):803-43, 2003.

Porter et al., Chimeric antigen receptor-modified T cells in chronic lymphoid leukemia. The New England journal of medicine; 365(8):725-33, 2011.

Purbhoo et al., T cell killing does not require the formation of a stable mature immunological synapse. Nature immunology; 5(5):524-30, 2004.

Ramuz et al., Identification of TCL1A as an immunohistochemical marker of adverse outcome in diffuse large B-cell lymphomas. Int J Oncol.; 26(1):151-7, 2005.

Remington: The Science and Practice of Pharmacy, 21st Ed. Lippincott Williams and Wilkins, 2005.

Remington's Pharmaceutical Sciences, 16th Ed., Mack, ed., 1980.

Reya et al., Stem cells, cancer, and cancer stem cells. Nature; 414(6859):105-11, 2001.

Sadelain et al., Cancer Discov., April; 3(4): 388-398, 2013.

Sambrook et al., Molecular Cloning: A Laboratory Manual, 3rd ed., Cold Spring Harbor Press, Cold Spring Harbor, N.Y., 2001.

Schuster et al., Sustained Remissions Following Chimeric Antigen Receptor Modified T Cells Directed Against CD19 (CTL019) in Patients with Relapsed or Refractory CD19+ Lymphomas. Blood; 126(23):183-, 2015.

Schuster et al., Vaccination with patient-specific tumor-derived antigen in first remission improves disease-free survival in follicular lymphoma. Journal of clinical oncology: official journal of the American Society of Clinical Oncology; 29(20):2787-94, 2011.

Singh et al., Redirecting specificity of T-cell populations for CD19 using the Sleeping Beauty system. *Cancer Res.*, 68:2961-2971, 2008.

Smith et al., A basal stem cell signature identifies aggressive prostate cancer phenotypes. Proceedings of the National Academy of Sciences; 112(47):E6544-E52, 2015.

Sotillo et al., Convergence of Acquired Mutations and Alternative Splicing of CD19 Enables Resistance to CART-19 Immunotherapy. Cancer Discov; 5(12):1282-95, 2015.

Stancovski et al., *J. Immunol.*, 151:6577, 1993.

Stone et al., A sensitivity scale for targeting T cells with chimeric antigen receptors (CARs) and bispecific T-cell Engagers (BiTEs). Oncoimmunology; 1(6):863-73, 2012.

Stone et al., TCR affinity for p/MHC formed by tumor antigens that are self-proteins: impact on efficacy and toxicity. Curr Opin Immunol.; 33:16-22, 2015.

Sykulev et al., Evidence that a single peptide-MHC complex on a target cell can elicit a cytolytic T cell response. Immunity; 4(6):565-71, 1996.

Teitell M A. The TCL1 family of oncoproteins: co-activators of transformation. Nat Rev Cancer; 5(8):640-8, 2005.

Terakura et al., Blood. 1:72-82, 2012.

Topp et al., Phase II trial of the anti-CD19 bispecific T cell-engager blinatumomab shows hematologic and molecular remissions in patients with relapsed or refractory B-precursor acute lymphoblastic leukemia. J Clin Oncol.; 32(36):4134-40, 2014.

Turtle et al., "Artificial antigen-presenting cells for use in adoptive immunotherapy" Cancer J. 2010 July-August; 16(4) 374-81.

Turtle et al., CD19 CAR-T cells are highly effective in ibrutinib-refractory chronic lymphocytic leukemia. Blood.; 128(56), 2016b.

Turtle et al., Curr. Opin. Immunol., October; 24(5): 633-39, 2012.

Turtle et al., Immunotherapy of non-Hodgkin's lymphoma with a defined ratio of CD8+ and CD4+ CD19-specific chimeric antigen receptor-modified T cells. Science translational medicine; 8(355) 355ra116, 2016a.

van Loenen et al., Optimization of the HA-1-specific T-cell receptor for gene therapy of hematologic malignancies. Haematologica; 96(3):477-81, 2011.

Walseng et al., A TCR-based Chimeric Antigen Receptor. Scientific Reports; 7(1):10713, 2017.

Wang et al., J Immunother. 35(9):689-701, 2012.

Wang et al., Octamer 4 (Oct4) mediates chemotherapeutic drug resistance in liver cancer cells through a potential Oct4-AKT-ATP-binding cassette G2 pathway. Hepatology (Baltimore, Md.); 52(2):528-39, 2010.

Watanabe et al., Target antigen density governs the efficacy of anti-CD20-CD28-CD3 zeta chimeric antigen receptor-modified effector CD8+ T cells. Journal of immunology (Baltimore, Md.: 1950); 194(3):911-20, 2015.

Weijtens et al. (1996) Single chain Ig/gamma gene-redirected human T lymphocytes produce cytokines, specifically lyse tumor cells, and recycle lytic capacity. J Immunol. 1996 Jul. 15; 157(2):836-43.

Weng et al., IL-15 enhances the antitumor effect of human antigen-specific CD8+ T cells by cellular senescence delay. Oncoimmunology; 5(12):e1237327, 2016b.

Weng et al., Targeting B-cell malignancies through human B-cell receptor specific CD4+ T cells. Oncoimmunology; 5(11):e1232220, 2016a.

Weng et al., TCL1: a shared tumor-associated antigen for immunotherapy against B-cell lymphomas. Blood; 120 (8):1613-23, 2012.

Wu et al., Cancer, March 18(2): 160-75, 2012.

Zhong et al., T-cell receptor affinity and avidity defines antitumor response and autoimmunity in T-cell immunotherapy. Proc Natl Acad Sci USA. 2013; 110(17):6973-8.

What is claimed is:

1. An engineered T cell receptor (TCR) having antigenic specificity for T-cell leukemia/lymphoma 1 (TCL1) or SEQ ID NO:29, wherein the TCR comprises the amino acid sequences of SEQ ID NO: 54, 55, 56, 57, 58, and 59.

2. The TCR of claim 1, wherein the engineered TCR comprises:
   (i) an alpha chain variable region having the amino acid sequence of SEQ ID NO:1 or a sequence having at least 90% sequence identity to SEQ ID NO:1; and/or
   (ii) a beta chain variable region having the amino acid sequence of SEQ ID NO:2 or a sequence having at least 90% sequence identity to SEQ ID NO:2.

3. The TCR of claim 2, wherein the engineered TCR binds HLA-A2 or HLA-A*0201, or has antigenic specificity for TCL1 in the context of HLA-A2 or HLA-A*0201.

4. The TCR of claim 1, wherein the TCR comprises an alpha chain variable region having at least 95% identity to the amino acid sequence of SEQ ID NO:1 and/or a beta chain variable region having at least 95% identity to the amino acid sequence of SEQ ID NO:2.

5. The TCR of claim 4, wherein the TCR comprises an alpha chain variable region having at least 99% identity to the amino acid sequence of SEQ ID NO:1 and/or a beta chain variable region having at least 95% identity to the amino acid sequence of SEQ ID NO:2.

6. The TCR of claim 4, wherein the TCR comprises an alpha chain variable region having at least 95% identity to the amino acid sequence of SEQ ID NO:1 and/or a beta chain having at least 99% identity to the amino acid sequence of SEQ ID NO:2.

7. The TCR of claim 4, wherein the TCR comprises an alpha chain having at least 95% identity to the amino acid sequence of SEQ ID NO:3 and/or a beta chain having at least 95% identity to the amino acid sequence of SEQ ID NO:4.

8. The TCR of claim 4, wherein the TCR comprises an alpha chain comprising the amino acid sequence of SEQ ID NO:3 and/or a beta chain comprising the amino acid sequence of SEQ ID NO:4.

9. The TCR of claim 1, wherein the TCR comprises an alpha chain variable region of SEQ ID NO:1 and/or a beta chain of SEQ ID NO:2.

10. The TCR of claim 1, wherein the TCR is further defined as a soluble TCR, wherein the soluble TCR does not comprise a transmembrane domain.

11. The TCR of claim 1, further comprising a detectable label.

12. The TCR of claim 1, wherein the TCR is covalently bound to a therapeutic agent.

13. The TCR of claim 12, wherein the therapeutic agent is an immunotoxin or a chemotherapeutic agent.

14. A multivalent TCR complex comprising a plurality of TCRs according to claim 1.

15. A nucleic acid comprising or consisting of a nucleotide sequence encoding the TCR of claim 1.

16. An expression vector comprising the nucleic acid according to claim 15.

17. A method for engineering a host cell comprising contacting said host cell with the expression vector of claim 16.

18. A host cell engineered to express the TCR of claim 1.

19. A method of treating cancer in a subject comprising administering an effective amount of the cells of claim 18 to a subject, wherein the cancer expresses TCL1.

\* \* \* \* \*

UNITED STATES PATENT AND TRADEMARK OFFICE
CERTIFICATE OF CORRECTION

| | | |
|---|---|---|
| PATENT NO. | : 11,919,937 B2 | Page 1 of 1 |
| APPLICATION NO. | : 16/961088 | |
| DATED | : March 5, 2024 | |
| INVENTOR(S) | : Weng et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 877 days.

Signed and Sealed this
Eighth Day of October, 2024

Katherine Kelly Vidal
*Director of the United States Patent and Trademark Office*